US009610337B2

(12) United States Patent
Triccas et al.

(10) Patent No.: US 9,610,337 B2
(45) Date of Patent: Apr. 4, 2017

(54) PREVENTION AND TREATMENT OF MYCOBACTERIUM INFECTION

(71) Applicants: The University of Sydney, Sydney, NSW (AU); CENTENARY INSTITUTE OF CANCER MEDICINE AND CELL BIOLOGY, Camperdown, NSW (AU)

(72) Inventors: James Anthony Triccas, Sydney (AU); Rachel Pinto-Nadanachandran, Sydney (AU); Warwick John Britton, Sydney (AU)

(73) Assignee: The University of Sydney Centenary Institute of Cancer Medicine and Cell Biology, New South Wales (AU)

( * ) Notice: Subject to any disclaimer, the term of this patent is extended or adjusted under 35 U.S.C. 154(b) by 0 days.

(21) Appl. No.: 14/367,854

(22) PCT Filed: Dec. 20, 2012

(86) PCT No.: PCT/AU2012/001569
§ 371 (c)(1),
(2) Date: Jun. 20, 2014

(87) PCT Pub. No.: WO2013/091004
PCT Pub. Date: Jun. 27, 2013

(65) Prior Publication Data
US 2016/0022795 A1    Jan. 28, 2016

Related U.S. Application Data

(60) Provisional application No. 61/579,166, filed on Dec. 22, 2011.

(51) Int. Cl.
| | | |
|---|---|---|
| A61K 39/04 | (2006.01) | |
| C07K 14/35 | (2006.01) | |
| C12N 9/12 | (2006.01) | |
| A61K 38/00 | (2006.01) | |
| A61K 39/00 | (2006.01) | |

(52) U.S. Cl.
CPC ........... *A61K 39/04* (2013.01); *C07K 14/35* (2013.01); *C12N 9/1241* (2013.01); *A61K 38/00* (2013.01); *A61K 2039/523* (2013.01); *A61K 2039/55511* (2013.01); *A61K 2039/55572* (2013.01); *A61K 2039/57* (2013.01); *C07K 2319/00* (2013.01); *C07K 2319/40* (2013.01); *C12Y 207/07004* (2013.01)

(58) Field of Classification Search
None
See application file for complete search history.

(56) References Cited

U.S. PATENT DOCUMENTS

| | | | | |
|---|---|---|---|---|
| 2007/0042383 A1* | 2/2007 | Kapur | ............ | C12Q 1/689 435/6.15 |
| 2011/0287087 A1* | 11/2011 | Christensen | ............ | A61K 9/127 424/450 |

FOREIGN PATENT DOCUMENTS

| | | | |
|---|---|---|---|
| WO | WO9637219 | * | 11/1996 |
| WO | WO0204018 | * | 1/2002 |
| WO | 02086067 | | 10/2002 |
| WO | WO 02/086067 | * | 10/2002 |

OTHER PUBLICATIONS

Principi et al. Tuberculosis 95 (2015) 6-13.*
Plotkin, S.A. et al. (eds). Vaccines. Chapter 29. W. B. Saunders company (Philadelphia) in 1988.*
Cole et al. Nature 393,537-544, 1998.*
Pinto et al. Microbiology, 2004, vol. 150, pp. 1681-1686.*
Olsen et al. Infection and Immunity vol. 69 No. 5, May 2001, p. 2773-2778.*
Accession No. A70772 from Cole et al. Nature 393,537-544, 1998.*
Pinto et al., "The Mycobacterium tuberculosis cysD and cysNC genes form a stress-induced operon that encodes a tri-functional sulfate-activating complex," Microbiology 150:1681-1686 (2004).
Senaratne et al., "Vaccine efficacy of an attenuated but persistent Mycobacterium tuberculosis cysH mutant," Journal of Medical Microbiology 56:454-458 (2007).
Sun et al., "The trifunctional sulfate-activating complex (SAC) of Mycobacterium tuberculosis," The Journal of Biological Chemistry 280(9):7861-7866 (2005).
Pinto et al., "Host-cell-induced components of the sulfate assimilation pathway are major protective antigens of Mycobacterium tuberculosis," The Journal of Infectious Diseases 207:778-785 (2012).

* cited by examiner

*Primary Examiner* — Oluwatosin Ogunbiyi
(74) *Attorney, Agent, or Firm* — Edward J. Baba; Khin K. Chin; Bozicevic, Field & Francis LLP

(57) ABSTRACT

The invention relates to the identification of antigens, including *Mycobacterium* sulphate assimilation pathway components such as CysD, for preventing and treating *Mycobacterium* infection, especially but not exclusively *Mycobacterium tuberculosis* infection; to expression systems including live *Mycobacterium* for expression of said antigens for prevention and treatment of said infection; and to use of said antigens and expression systems for prevention and treatment of said infection.

8 Claims, 16 Drawing Sheets

PREVENTION AND TREATMENT OF MYCOBACTERIUM INFECTION

FIELD OF THE INVENTION

The invention relates to the identification of antigens for preventing and treating *Mycobacterium* infection, especially but not exclusively *Mycobacterium tuberculosis* infection, to expression systems including live *Mycobacterium* for expression of said antigens for prevention and treatment of said infection, and to use of said antigens and expression systems for prevention and treatment of said infection.

BACKGROUND OF THE INVENTION

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

*Mycobacterium tuberculosis*, the causative agent of *tuberculosis* (TB) claims almost 2 million lives annually ((Dye, 2010) and globally is the leading cause of death due to a single bacterial agent. The situation has become more critical in the past decade due to co-infection with HIV and the inefficiency of the current vaccine, *Bacillus* Calmette-Guérin (BCG), to protect adults against TB ((Dye, 2010).

The identification of novel and protective antigens recognised by infected individuals would represent a major advance in the control of TB and may form the basis of new therapeutics to limit disease spread.

Current TB vaccines in clinical trials include viral-vectored or adjuvant-based subunit vaccines, as well as whole mycobacterial vaccines, that express one or more immunogenic *M. tuberculosis* antigens ((Kaufmann, 2011). Most of these strategies are based on secreted antigens of *M. tuberculosis* that are presumably more readily 'seen' by the host immune response (reviewed in ((Kaufmann, 2011)). The protective efficacy in humans of these new candidate vaccines yet to be determined.

There remains a need for further candidate antigens and vaccines for prevention and/or treatment of *Mycobacterium* infection, especially *M. tuberculosis* infection.

Further to identification of antigens, the targeted modulation of antigen expression in antigen presenting cells by recombinant vaccine vehicles such as Bacille Calmette Guerin (BCG) would significantly aid development of effective immunotherapeutic strategies.

There remains a need for candidate expression systems, especially those capable of an immediate and sustained expression of protective antigen, thereby enabling improved antigen specific immune responses to *Mycobacterium*, especially *M. tuberculosis*.

SUMMARY OF THE INVENTION

The invention seeks to address one or more of the above mentioned needs and/or provide improvements in the prevention and/or treatment of *Mycobacterium* infection and in one embodiment provides a method for minimising the likelihood of development of a *Mycobacterium* infection in an individual including:
  forming an immune response to a component of a *Mycobacterium* sulphate assimilation pathway (SAP) in an individual;
  thereby minimising the likelihood of development of a *Mycobacterium* infection in the individual.

In another embodiment there is provided a method for providing an individual with immunity to *Mycobacterium* infection including:
  forming an immune response to a component of a *Mycobacterium* SAP in an individual;
  thereby providing the individual with immunity to *Mycobacterium* infection.

In another embodiment there is provided a method for preventing a *Mycobacterium* infection from developing in an individual including:
  providing a component of a *Mycobacterium* SAP in an individual requiring said prevention in conditions for enabling formation of an immune response to said component in said individual;
  thereby preventing the infection from developing in the individual.

In another embodiment there is provided a method for treating an individual having a *Mycobacterium* infection to at least minimise the progression of the infection or a condition associated with the infection including:
  providing a component of a *Mycobacterium* SAP in an individual requiring said treatment in conditions for enabling formation of an immune response to said component in said individual;
  thereby treating the individual.

In another embodiment there is provided a use of a component of a *Mycobacterium* SAP in the manufacture of a medicament for minimising the likelihood of development of a *Mycobacterium* infection in an individual.

In another embodiment there is provided a use of a component of a *Mycobacterium* SAP for minimising the likelihood of development of a *Mycobacterium* infection in an individual.

In another embodiment there is provided a method for determining whether an individual is immune to a *Mycobacterium* including:
  providing a component of a *Mycobacterium* SAP in an individual in conditions for enabling formation of an immune response to said component in said individual;
  determining whether the individual develops a protective immune response to said component;
  wherein development of a protective immune response determines that the individual is immune to a *Mycobacterium*;
  thereby determining whether the individual is immune to a *Mycobacterium*.

The *Mycobacterium* CsyD gene or gene product is a preferred component for use in the above described methods.

In another embodiment there is provided a vaccine or immune stimulating composition for providing an immune response to *Mycobacterium* in an individual including:
  a component of a *Mycobacterium* SAP;
  a compound for potentiating an immune response to the component of the *Mycobacterium* SAP.

In another embodiment there is provided a vaccine or immune stimulating composition for providing an immune response to *Mycobacterium* in an individual including:
  a *Mycobacterium* cell including a recombinant CysD gene or protein.

In another embodiment there is provided a recombinant protein suitable for use in the above described composition, said protein including a first region having a sequence encoded by a *Mycobacterium* CysD gene and one or more further regions having a sequence of a *Mycobacterium* antigen. Also provided is a nucleic acid encoding the recombinant protein, and an expression vector including said nucleic acid.

In another embodiment there is provided a protein suitable for use in the above described composition including a first region having a sequence encoded by a *Mycobacterium* CysD gene and a further region having a sequence encoded by a *Mycobacterium* Agb85 gene. Also provided is a nucleic acid encoding the protein and an expression vector including said nucleic acid.

In another embodiment there is provided an expression vector including a nucleic acid encoding a *Mycobacterium* CysD protein and a promoter, wherein said promoter is operably linked to the nucleic acid for expression of the nucleic acid when a *Mycobacterium* strain including the vector is introduced into an APC, said promoter having a sequence of a *Mycobacterium* promoter that causes expression of a *Mycobacterium* ATP independent chaperone.

In another embodiment there is provided a *Mycobacterium* including a recombinant protein, nucleic acid or expression vector described above. The cell may be derived from *M. tuberculosis* or may be an attenuated strain of *M. tuberculosis*.

In related embodiments there is provided a method for providing an antigen specific immune response to *Mycobacterium* infection including:
introducing a strain of *Mycobacterium* into an antigen-presenting cell (APC);
wherein said strain includes:
a recombinant nucleic acid encoding a *Mycobacterium* antigen for providing an antigen specific immune response to *Mycobacterium* infection;
a promoter operably linked to the recombinant nucleic acid for expression of the recombinant nucleic acid when the strain is introduced into an APC, said promoter having a sequence of a *Mycobacterium* promoter that causes expression of a *Mycobacterium* ATP independent chaperone.

In another embodiment there is provided an expression vector including:
a nucleic acid encoding a *Mycobacterium* antigen for providing an antigen specific immune response to *Mycobacterium* infection;
a promoter operably linked to the nucleic acid for expression of the nucleic acid when the strain is introduced into an APC, said promoter having a sequence of a *Mycobacterium* promoter that causes expression of a *Mycobacterium* ATP independent chaperone.

In the above described embodiments, the *Mycobacterium* HspX promoter is a preferred promoter for use as a promoter having the sequence of a *Mycobacterium* promoter that causes expression of a *Mycobacterium* ATP independent chaperone.

In another embodiment there is provided a strain of *Mycobacterium* including the above described expression vector.

In another embodiment there is provided an expression vector including:
a nucleic acid encoding a protein including a first region having a sequence encoded by a *Mycobacterium* CysD gene and a further region having a sequence encoded by a *Mycobacterium* Agb85 gene;
a *Mycobacterium* HspX promoter that causes expression of said nucleic acid when said vector is introduced into an APC.

In another embodiment there is provided a cell, typically a *M. tubercluosis* cell or an attenuated *Mycobacterium* cell, for example an attenuated *M. bovis* cell such as BCG, or an attenuated *M. tuberculosis* cell, said cell including the expression vector described above.

In a related embodiment there is provided a method for minimising the likelihood of development of a *M. tubercluosis* infection in an individual including:
providing an attenuated *M. tubercluosis* cell in an individual in which likelihood of development of said infection is to be minimised;
wherein said cell includes:
an expression vector including:
a recombinant nucleic acid encoding a protein including a first region having a sequence encoded by a *Mycobacterium* Agb85 gene and a further region having a sequence encoded by a *Mycobacterium* CysD gene;
a *Mycobacterium* HspX promoter that causes expression of said recombinant nucleic acid when said vector is introduced into an APC;
wherein said cell is provided in said individual in conditions for forming an immune response in the individual to said protein;
thereby minimising the likelihood of development of a *Mycobacterium* infection in the individual.

BRIEF DESCRIPTION OF THE DRAWINGS

FIG. 3. Protection afforded by DNA vaccines encoding members of the sulphate-activation complex following *M.* tuberculosis challenge. C57BL/6 (n=5) mice were immunised 3 times by i.m injection at 2-week intervals with 100 μg each of either pCDNA3, DNA-cysD, DNA-cysNC or DNA-cysD combined with DNA-cysNC. At the time of the first injection of DNA vaccines, mice were immunised once by s.c injection with $5 \times 10^5$ CFU of BCG. Four weeks following the third immunisation, mice were challenged with aerosol M. tubercluosis. Four weeks post challenge the bacterial load was determined in the lung (A) and the spleen (B). These data are shown as the mean. CFU (±SEM) per organ and are representative of 1 of 3 individual experiments for all groups. The significance of the differences between unvaccinated and immunised groups in the lung and spleen were determined by ANOVA; *p<0.001.

Figure 4:
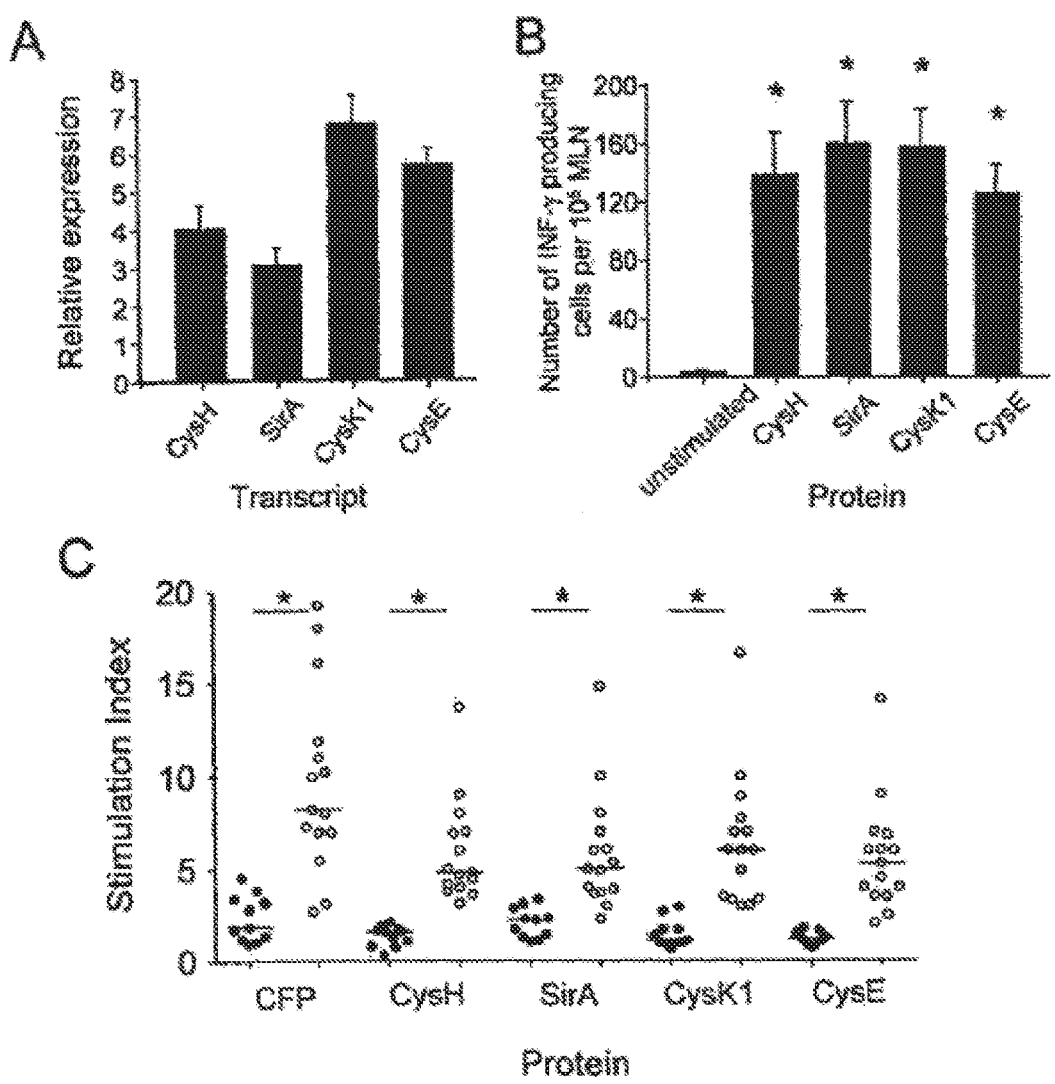

FIG. 4. Up-regulation and host immune recognition of downstream enzymes in the M. tuberculosis sulphate-activation pathway. (A) Relative up-regulation of M. tuberculosis SAP genes within RAW cells compared to in vitro grown bacilli. Total RNA was extracted from in vitro grown bacilli or M. tubercluosis infected RAW cells at 48 hrs post infection 1 μg of total RNA was reverse transcribed and subject to real-time PCR to assess expression of M. tubercluosis cysH, sirA, cysK1 and cysE. Data is the mean relative expression ±S.E.M measured in triplicate and is representative of two independent experiments. (B) Antigen-specific T cell responses in the MLN of mice were measured 8 weeks following M. tubercluosis challenge. IFN-γ secreting cells were enumerated by ELIspot following recall to CysH, SirA, CysK1 and CysE (10 μg/ml). Data are the means±S.E.M. for four mice and are representative of duplicate experiments. The significance of differences between protein-stimulated and unstimulated cells was determined by ANOVA; *p<0.0001. (C) Recognition of SAP proteins in TB infected individuals. Antigen-specific T cell responses were measured in the peripheral blood of M. tuberculosis infected patients (open circles) (n=15) and TST-ve individuals (filled circles) (n=11). T cell proliferation in response to M. tubercluosis CFP (as per FIG. 2C), CysH, SirA, CysK1 and CysE proteins at 10 μg/ml was measured as described in FIG. 2C. Significance of differences between M. tubercluosis infected patients and TST-ve individuals was determined by a Mann-Whitney U test; *p<0.001.

Figure 5:
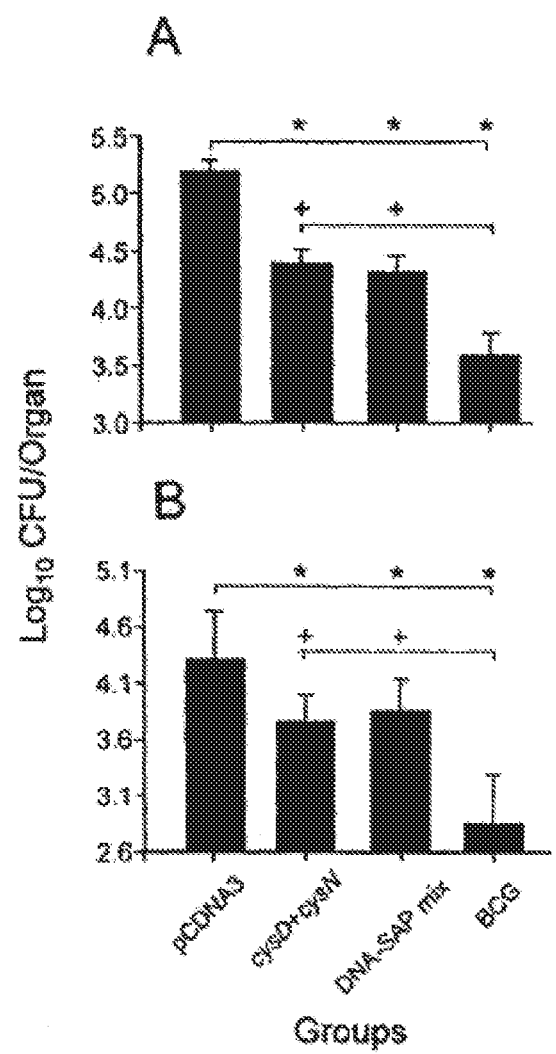

FIG. 5. Protective efficacy of DNA vaccines encoding downstream SAP enzymes. C57BL/6 mice (n=5) were immunised 3 times by i.m injection at 2-week intervals with 100 μg each of either pCDNA3, DNA-cysD combined with DNA-cysNC, or a mix of DNA vaccines expressing cysH, sirA, cysK1 or cysE. At the time of the first injection of DNA vaccines, mice were immunised once by s.c injection with $5 \times 10^5$ CFU of BCG. Four weeks following the third immunisation, mice were challenged by the aerosol M. tuberculosis. Four weeks later, the bacterial load was determined in the lung (A) and the spleen (B). These data are shown as the mean CFU (±SEM) per organ and are representative of 1 of 3 individual experiments for all groups. The significance of the differences between unvaccinated and immunised groups in the lung and spleen (*p<0.0001) and the differences between BCG immunised animals and other immunised groups (+p<0.0001) were determined by ANOVA.

Figure 6:
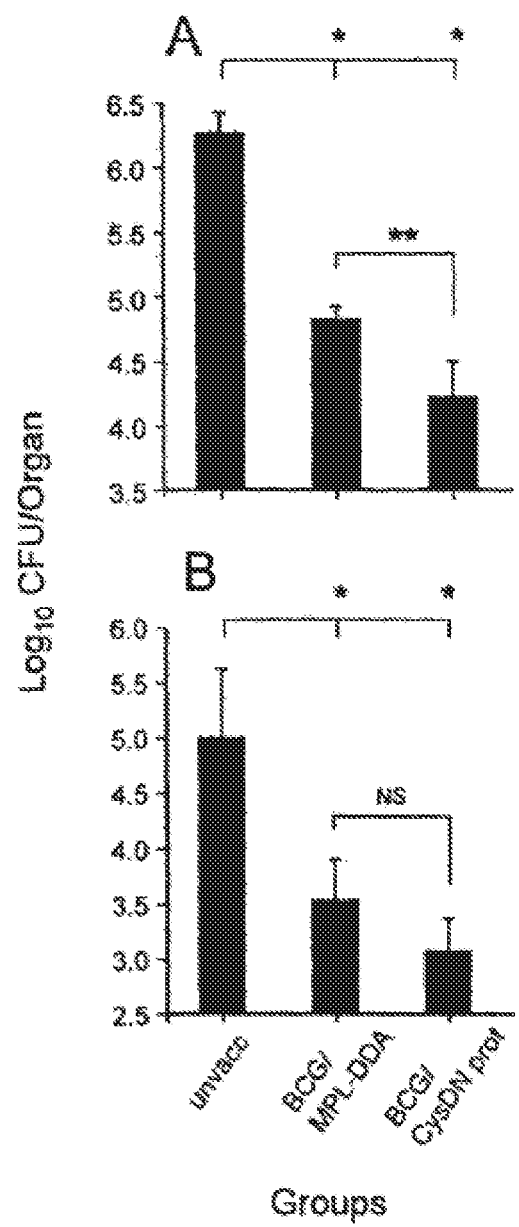

FIG. 6. Protective efficacy of BCG after boosting with CysDN protein. Groups of mice were immunized with 5×105 CFU BCG by s.c injection and after 24 weeks mice received s.c 100 μg of CysDNC protein in MPL-DDA (3 times at 2 week intervals). After 6 weeks mice were challenged with aerosol M. tuberculosis. Control mice were not immunized either no immunisation or immunisation with BCG and boosted with MPL-DDA adjuvant alone. Four weeks post-challenge the bacterial loads in the lung (A) and spleen (B) were determined. These data are presented as the mean bacterial number ±SEM per organ for 6 to 10 mice per group. Data are representative of 2 independent experiments. The significance of differences between unimmunised mice and other groups (*p<0.0001) and of the differences between BCG/MPL-DDA—immunised animals and other groups (**p<0.0001; NS—no significant difference) were determined by ANOVA.

Figure 7:
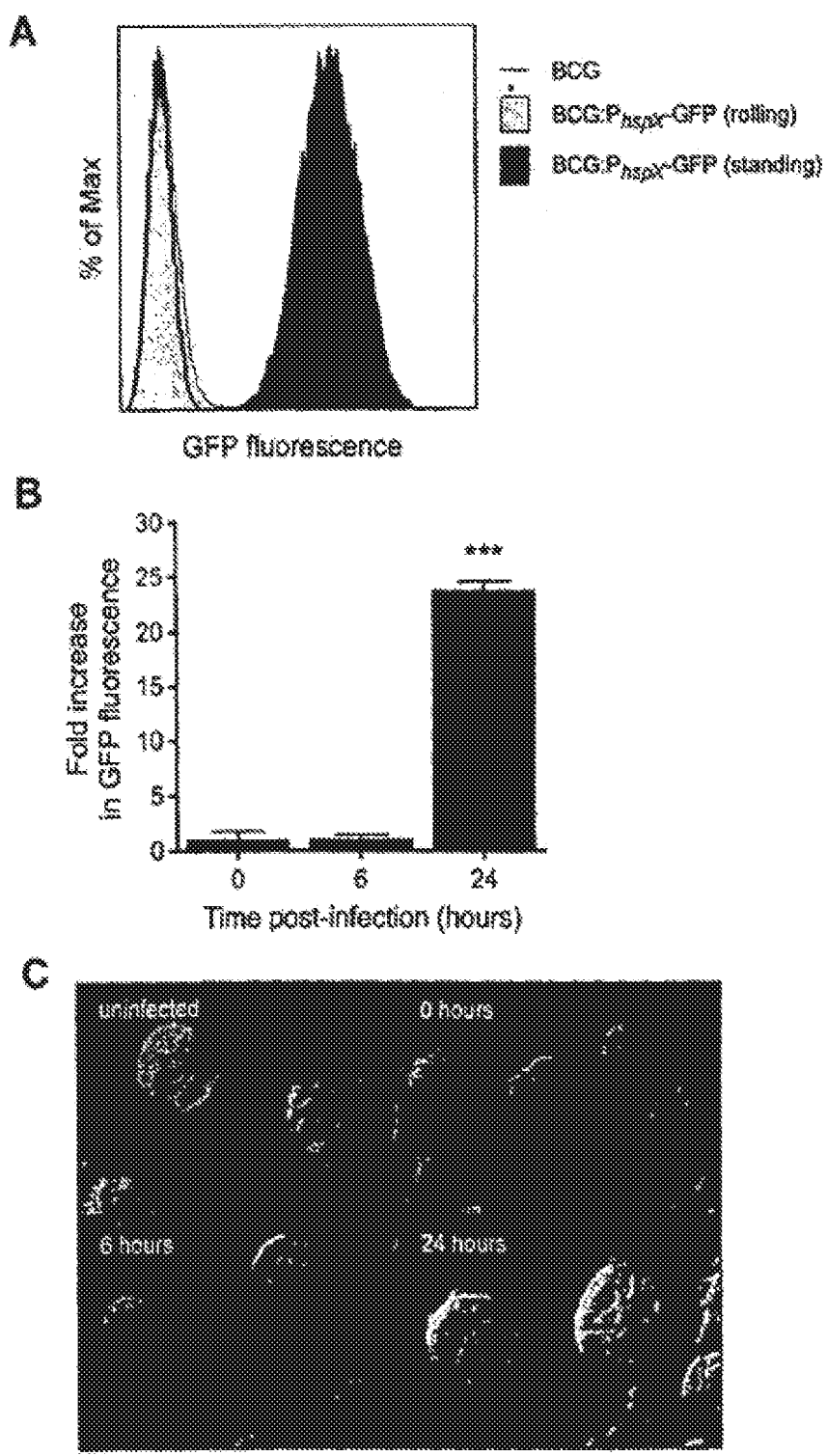

FIG. 7. Rapid induction of the hspX promoter within dendritic cells. The level of GFP expression by BCG Pasteur, aerated BCG:$P_{hspX}$-GFP cultures (rolling) or BCG:$P_{hspX}$GFP grown under low oxygen tension for 7 days (standing) was measured by flow cytometry (A). BMDC culture from C57BL/6 mice were infected with BCG:$P_{hspX}$-GFP at MOI of 1:1 and GFP fluorescence determined at 0, 6 and 24 h post-infection by flow cytometry (B). Data show means±SEM (n=3) and are representative of two independent experiments. The significances of differences relative to the zero timepoint were determined by ANOVA (***p<0.0001). GFP expression by BCG:$P_{hspX}$-GFP was visualized by confocal microscopy at 0, 6 and 24 h post-BMDC infection (C). Images shown are composites using the GFP filter and phase-contrast images to visualize cellular morphology.

Figure 8:
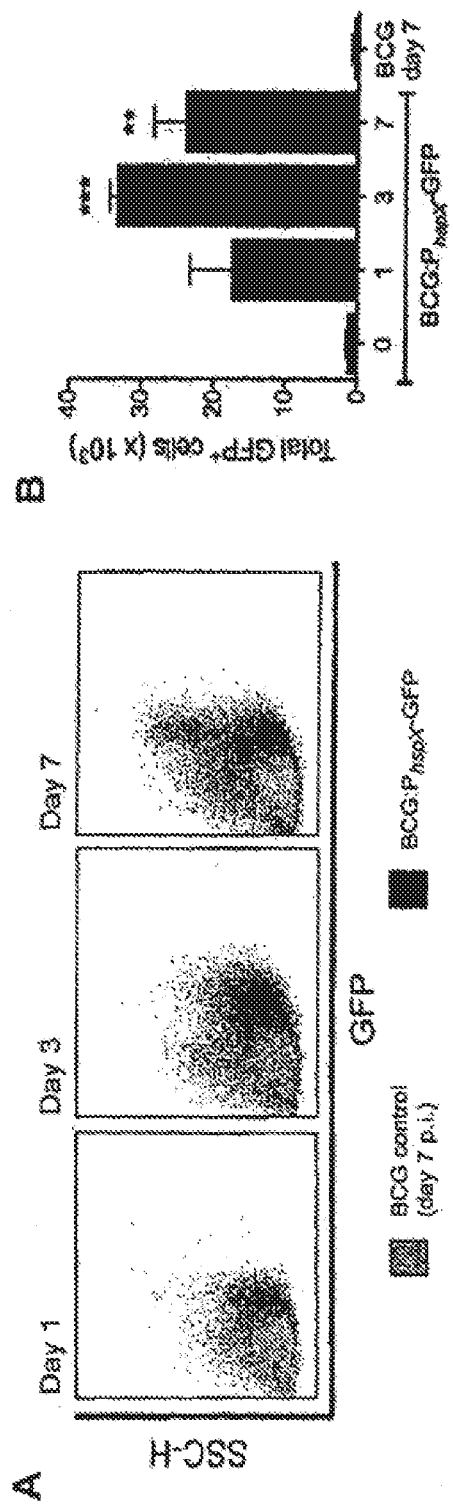

FIG. 8. In vivo induction of the hspX promoter within the host. Mice were vaccinated subcutaneously with $1 \times 10_7$ CFU of control BCG or BCG:$P_{hspX}$-GFP and at 0, 1, 3 and 7 days post-infection the level of GFP expression in $CD45_+$ cells from the infection site was determined (A). Scatter plot of cells from BCG:$P_{hspX}$-GFP mice (black dots) is overlaid on the level of GFP expression from mice infected with control BCG (grey dots). The total number of GFP from the injected is shown in (B). Data shown are the means±SEM and are representative of two independent experiments. The significance of differences between day 0 and other time-points was determined by ANOVA (p<0.01; *p<0.0001).

Figure 9:
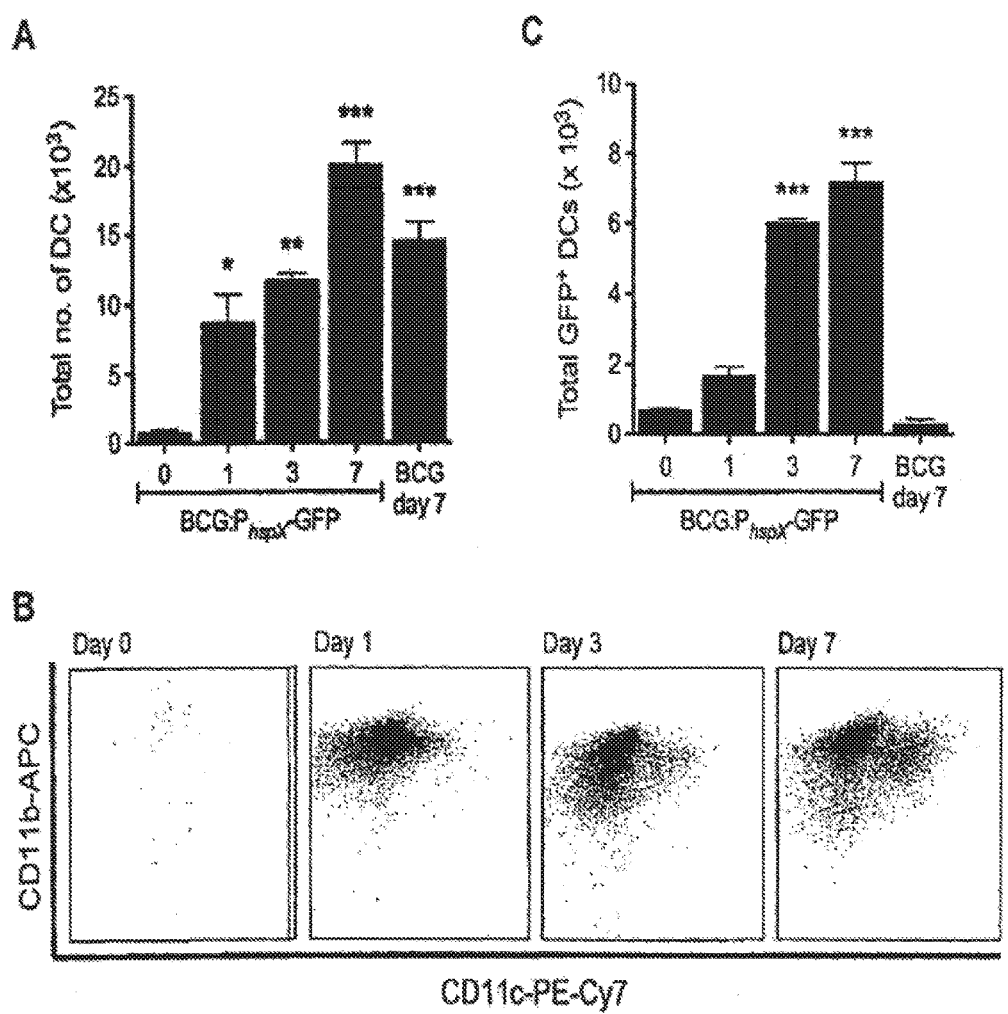

FIG. 9. Expression of the hspX promoter within dendritic cells recruited to the site of vaccination. Mice were vaccinated as described in FIG. 2 and the number of cells displaying a DC phenotype ($CD11c_{hi}CD11b_{hi}$) was determined by flow cytometry (A). GFP-expressing cells within CD45, population is shown as a scatter plot (B) along with the total number of GFP $CD11b_{hi}CD11c_{hi}$ cells at the vaccination site over the timecourse (C). Data shown are means±SEM and are representative of two independent experiments. The significance of differences between day 0 and other time-points was determined by ANOVA (*p<0.05; p<0.001; *p<0.0001).

Figure 10:
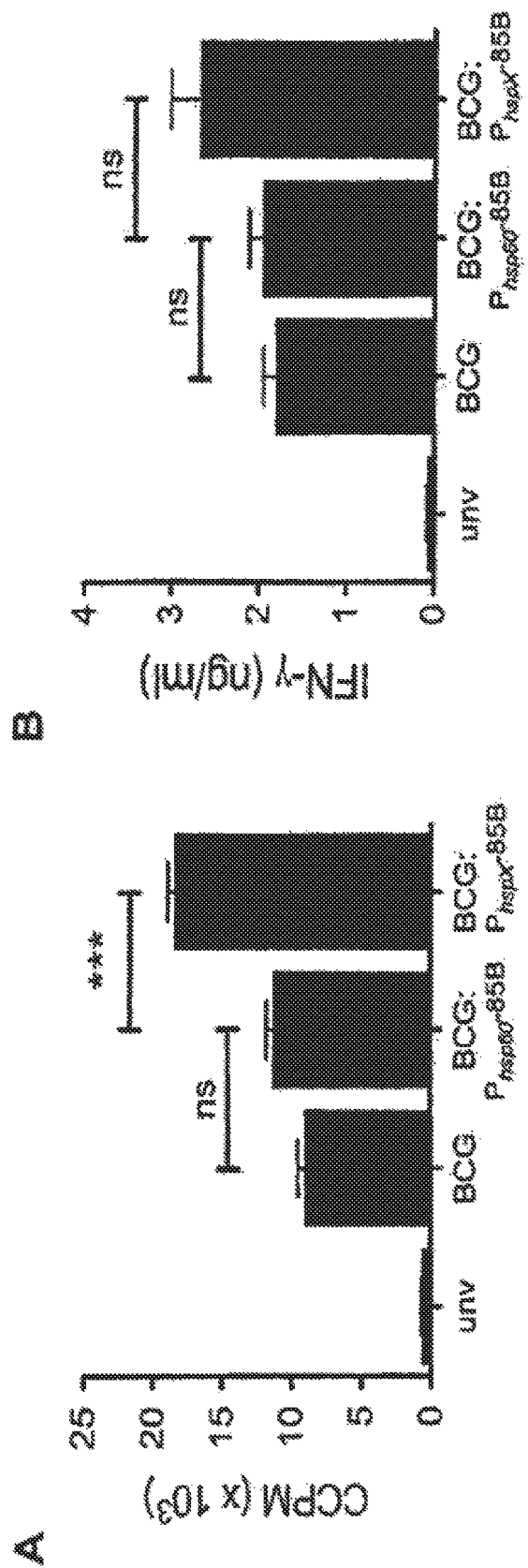

FIG. 10. The hspX promoter can facilitate improved T cell recognition of a recombinant antigen within APCs. Cultured BMDC were left uninfected (uni) or infected with control BCG, BCG:$P_{hspX}$-85B or BCG:$P_{hspX}$-85B for 4 h prior to co-incubation with Ag85B-specific T cells purified from p25 mice. The proliferation (A) and IFN-_ release (B) by p25 T cells at day 3 was determined by [$_3$H]-thymidine uptake or IFN-_ ELISA respectively. Data show means±SEM (n=3) and are representative of at least two independent experiments. The significances of differences between uninfected cells and other groups were determined by ANOVA (***p<0.0001; ns, not significant).

Figure 11:
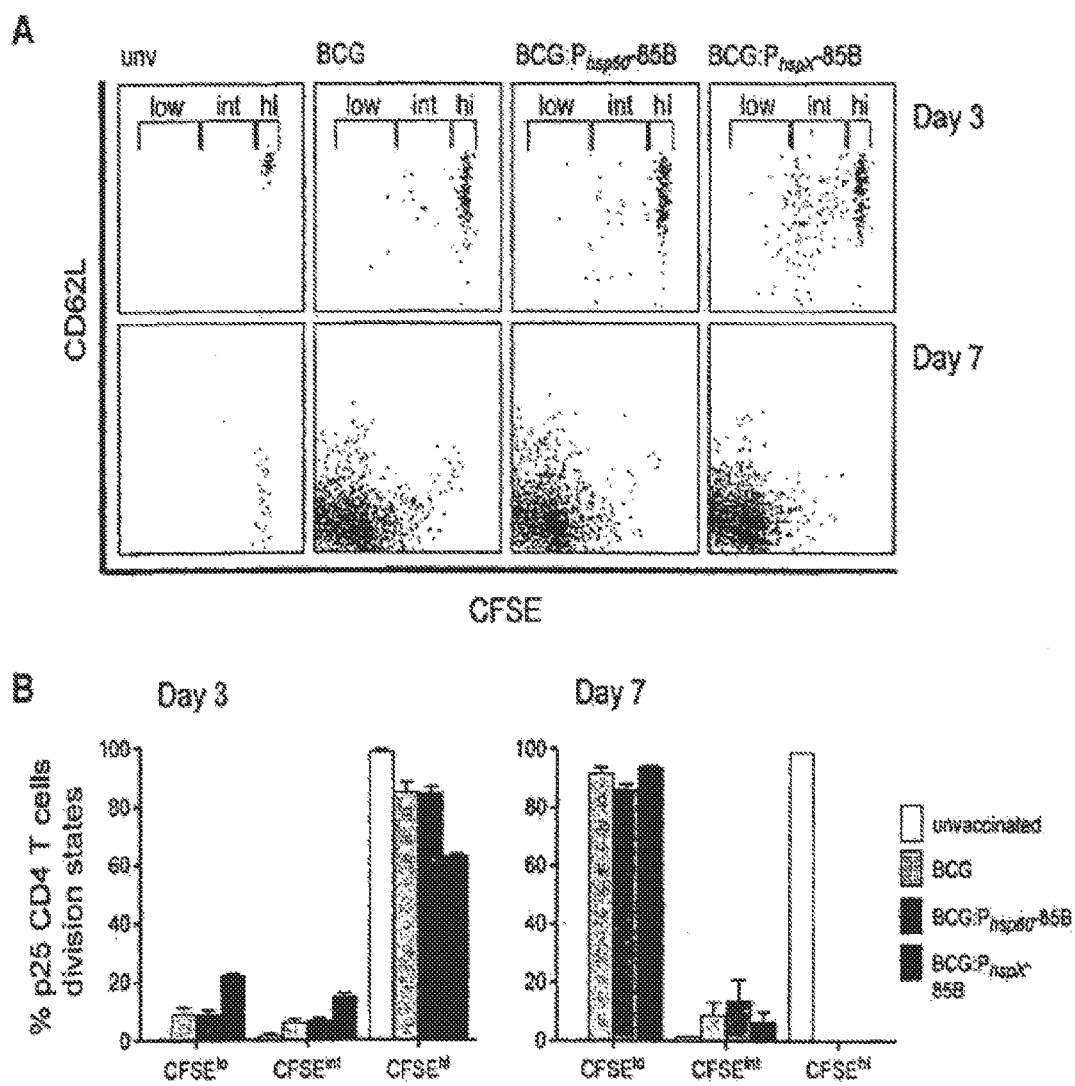

FIG. 11. Priming of Ag85B-reactive T cells in the DLNs of mice vaccinated with BCG:$P_{hspX}$-85B. C57BL/6 mice were injected intravenously with $5 \times 10_5$ CFSE-labelled p25 transgenic lymph node cells and one day later left as uninfected controls (unv) or subcutaneously vaccinated with $5 \times 10_5$ CFU of BCG, BCG:$P_{hsp60}$-85B or BCG:$P_{hspX}$-85B.

At 3 or 7 days post-infection, the CFSE and CD62L profile of transferred p25 CD4 T cells in the DLNs was determined (A). The division states are represented as $CFSE_{hi}$ (hi), $CFSE_{int}$ (divisions 1-5, int) or $CSFE_{lo}$ (divisions >6, low). The proportion of p25 CD4 T cells in division states based on CFSE levels was determined (B).

Figure 12:
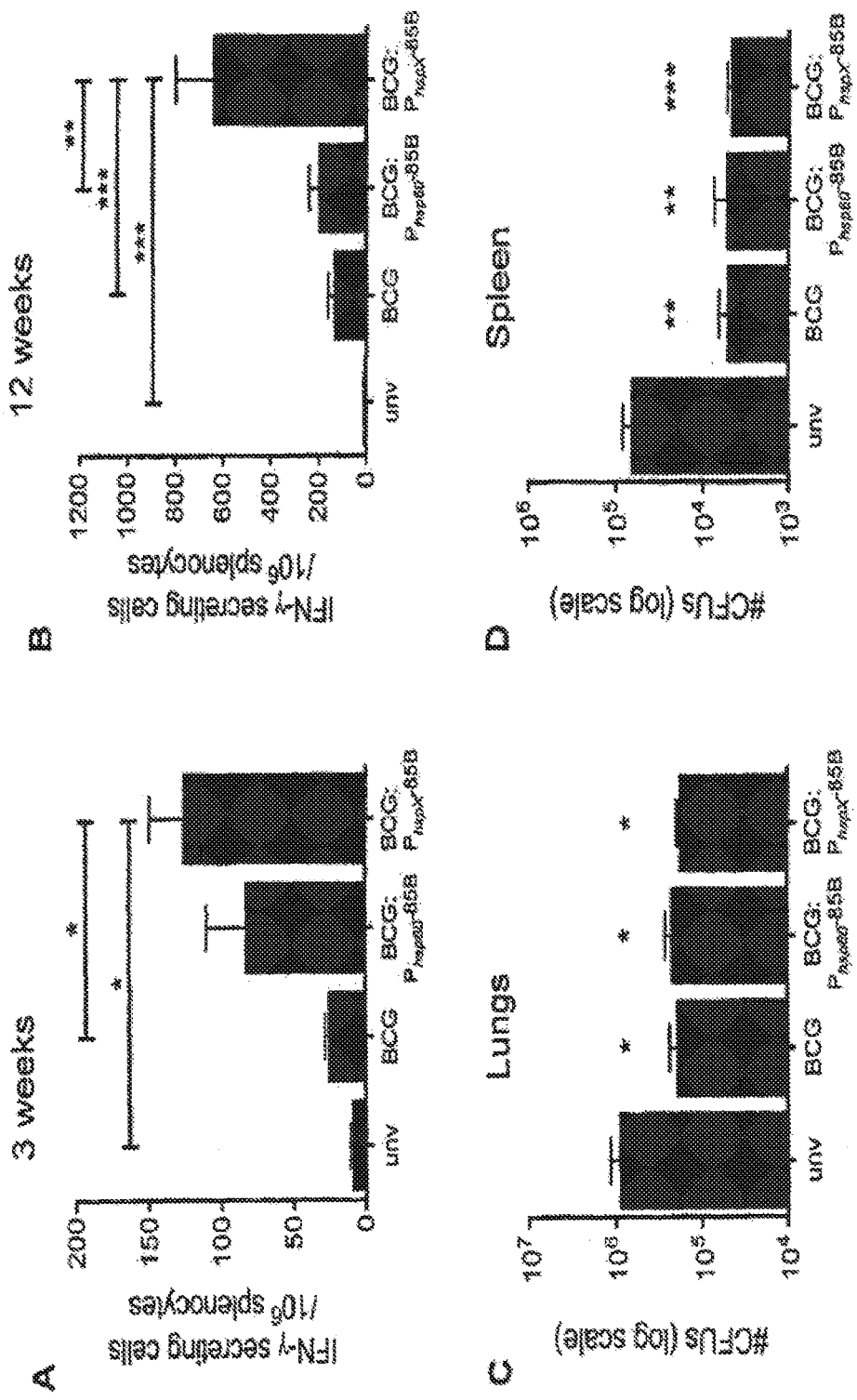

FIG. 12. Increased specific T cell immunity induced by vaccination with BCG expressing Ag85B under the control of the hspX promoter. Mice were left unvaccinated (unv) or vaccinated subcutaneoulsy with $5\times10_5$ CFU of control BCG, $BCG:P_{hsp60}$-85B or $BCG:P_{hspX}$-85B. The number of IFN-_-secreting splenocytes responding to the p25 peptide from Ag85B was determined at 3 weeks (A) or 12 weeks (B) post-vaccination. Twelve weeks following vaccination, groups of mice were also aerosolized with M. tuberculosis H37Rv and 4 weeks post-challenge the M. tuberculosis load in the lungs (C) and the spleen (D) were determined. Data shown are the means±SEM for three mice per group and are representative of two independent experiments. The significances of differences between unvaccinated mice and BCG-vaccinated groups were determined by ANOVA (*$p<0.05$; $p<0.001$; *$p<0.0001$).

Figure 13:
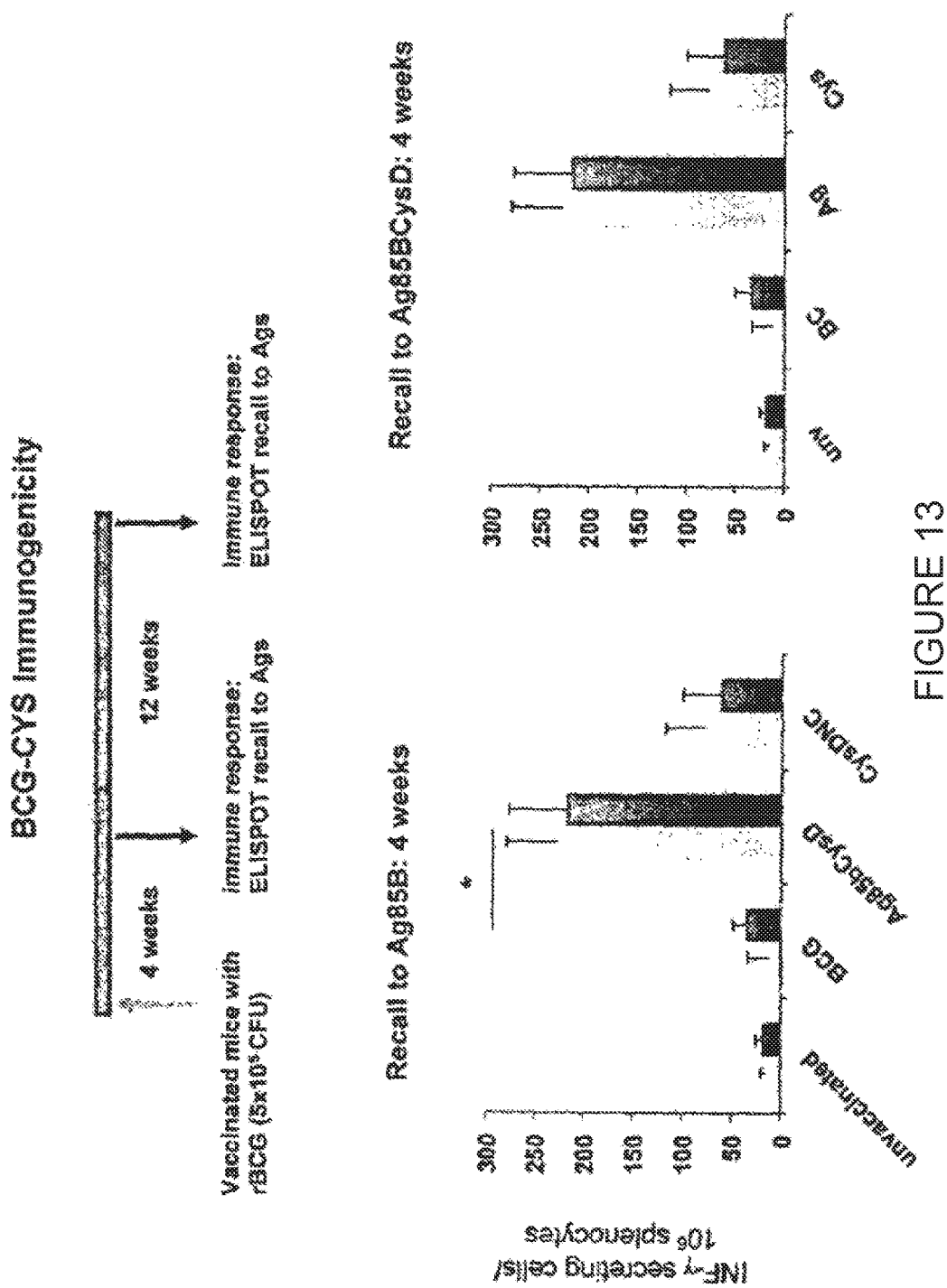
Figure 13:
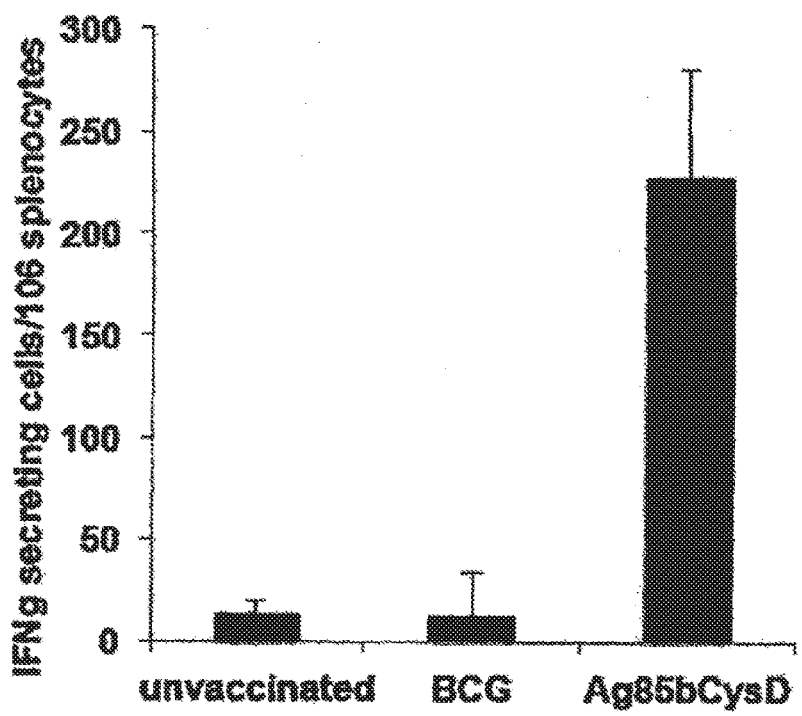

FIG. 13. Vaccination with BCG:Ag85BCysD displays improved immunogenicity. C57BL/6 mice (n=5) were immunised with $5\times10^5$ CFU of BCG or BCG expressing the Ag85BCysD fusion protein. Splenocytes re-stimulated with Ag85BCysD protein demonstrated an increased number of IFN-g-secreting cells compared with splenocytes from mice immunised with BCG only.

Figure 14:
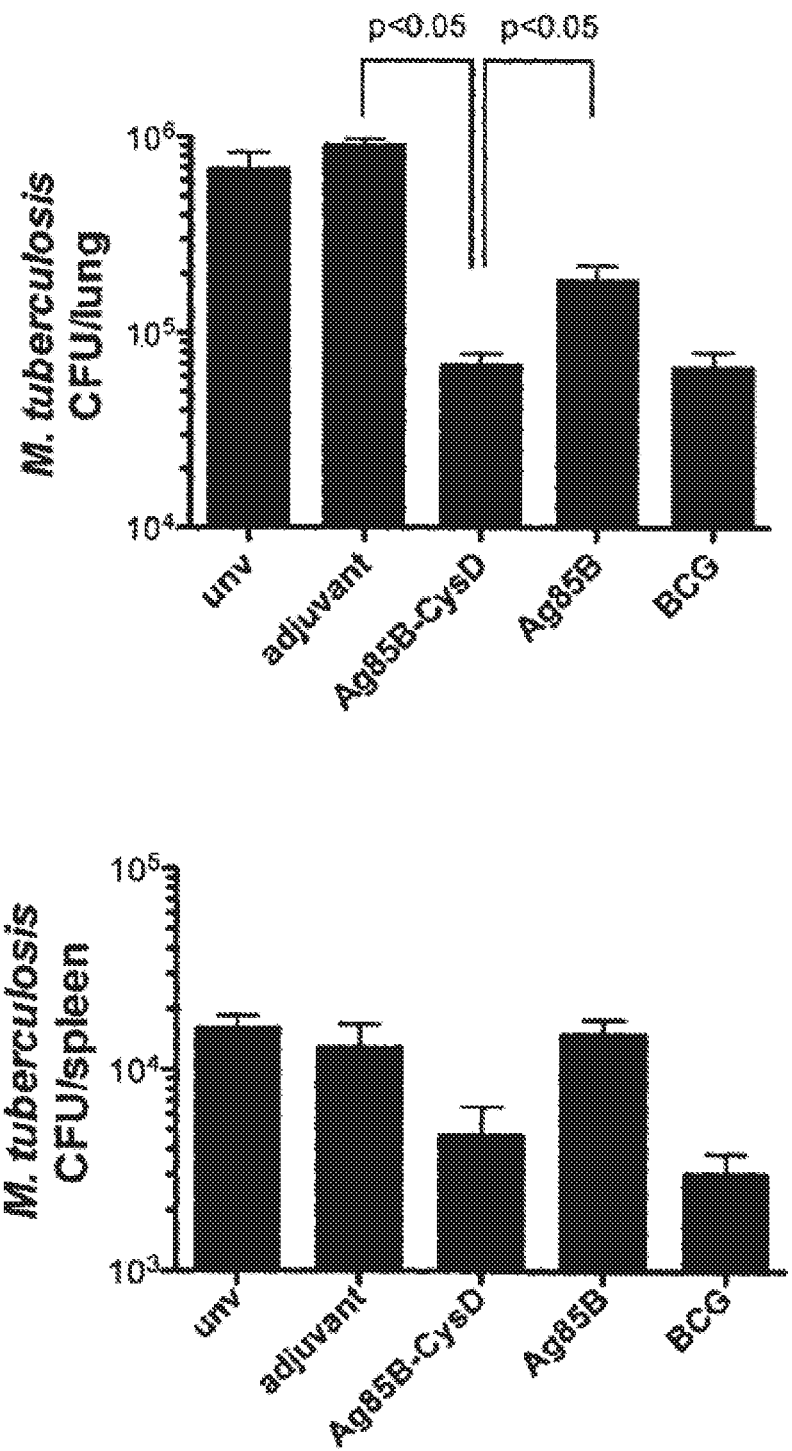

FIG. 14. Protection induced by the Ag85B-CysD fusion protein. C57BL/6 mice (n=5) were immunized 3 times by s.c injection with either adjuvant (MPL/DDA), Ag85B-CysD fusion protein (10 mg) or Ag85B (10 mg). At the time of the first injection of protein vaccines, mice were immunized once by s.c injection with $5\times10^5$ CFU of BCG. Four weeks following the third immunization, mice were challenged with aerosol M. tuberculosis with an infective dose of □100 viable bacilli per lung and bacterial load was determined in the lung (A) and the spleen (B) 4 weeks later. Data are shown as the mean CFU (±SEM) per organ. The significance of the differences between groups was evaluated by one-way ANOVA with pair-wise comparison of multi-grouped data sets achieved using the Bonferroni post hoc test.

Figure 15:
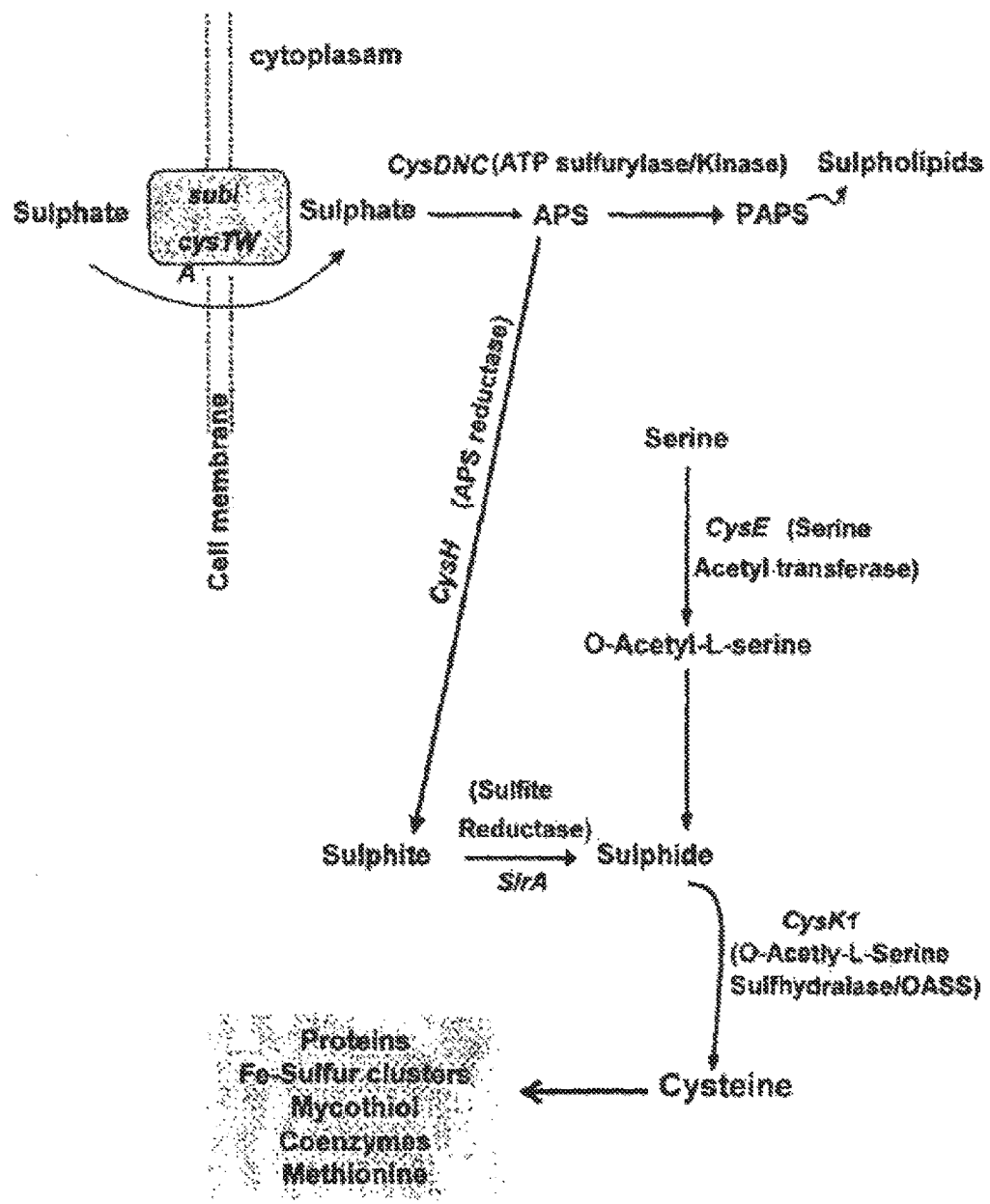

FIG. 15. Sulphate assimilation in mycobacteria. Once imported into the cell, sulphate is activated by ATP Sulfurylase, encoded by cysDNC to produce adenosine-5'-phosphosulfate (APS). In mycobacteria, APS lies at a metabolic branch point. It could be phosphorylated by APS kianse, encoded by cysC, to produce phosphoadenosine-5'-phosphosulfate (PAPS), which functions as the universal sulphate donor for the sulfation of biomolecules that are the building block of the mycobacterial cell wall. The sulphate moiety in APS could also be reduced to sulfite, catalysed by APS reductase and encoded by cysH. Sulfite is further reduced to sulphide by sulfite reductase, (encoded by sirA) and is the form of sulphur that is incorporated into cysteine in the last step of this reductive pathway involving two enzymes, O-Acetylserine sulfhydralse (OASS) and serine acetyltransferase encoded by cysK1 and cysE respectively. Cysteine is the building block of many important molecules in mycobacteria.

DETAILED DESCRIPTION OF THE EMBODIMENTS

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text or drawings. All of these different combinations constitute various alternative aspects of the invention.

All of the patents and publications referred to herein are incorporated by reference in their entirety.

For purposes of interpreting this specification, terms used in the singular will also include the plural and vice versa.

As described herein, the inventors show that sulphate assimilation pathway (SAP) genes and related gene products are highly immunoreactive in the sense that stimulation of lymph node derived lymphocytes from M. tubercluosis-infected mice with SAP proteins provides a strong Th1 response lasting for up to 8 weeks post infection. Further, in humans infected with M. tuberculosis, peripheral blood lymphocytes were observed to proliferate in response to SAP proteins to a greater extent than cells from M. tubercluosis negative individuals.

Further to the above, the inventors show that SAP genes and proteins can be utilised to induce an antigen specific protective immune response. More specifically, the inventors show that immunisation with SAP genes and proteins provides protection to lungs and spleen in mice subsequently infected with M. tubercluosis and the protective efficacy approached that observed with BCG immunisation.

Still further, the inventors show that SAP genes and gene products can be used to improve the protective immunity provided by BCG vaccination whereby, as shown in the specification, the SAP components improved the protective effect of BCG against M. tubercluosis infection which was most apparent in lung tissue.

As discussed herein, these findings are unanticipated as SAP proteins are proposed to be intracellular or membrane associated proteins which, given location, should be less likely than secreted proteins to be subject to immune surveillance. In this regard it is surprising that the amount of immune activation observed in these studies is equivalent to that observed for the cell surface antigen or secreted antigen, Ag85B.

A. Definitions

As used herein, except where the context requires otherwise, the term "comprise" and variations of the term, such as "comprising", "comprises" and "comprised", are not intended to exclude further additives, components, integers or steps.

Sulphate assimilation pathway or SAP generally refers to the pathway by which Mycobacteria reduce sulphur, thereby obtaining substrate for the biosynthesis of cysteine and downstream products including mycothiol. In more detail, the pathway involves the formation of adenosine 5'-phosphosulfate (APS) from sulphate, from which APS reductase (encoded by CysH) may produce sulphite, and from which sulfite reductase (encoded by SirA) may produce sulphide, and from which, and with O-Acetyl-L-serine, O-Acetyl-L-

Serine Sulfhydalase (encoded by CysK1) may produce cysteine. Key enzymes of SAP include ATP sulfurylase (adenylyl-transferase) (encoded by CysD), GTPase (encoded by CysN), and APS kinase. These enzymes enable the formation of PAS from sulphate, and the formation of 3' phosphoadenosine 5'-phosphosulfate (PAPS) from APS.

A SAP component generally refers to a protein or enzyme involved in the reduction of sulphur in *Mycobacterium* according to the SAP, examples of which include those encoded by CysD, CysNC, CysH, SirA, CysE, CysK1 genes.

Sulphate activating complex or SAC generally refers to a heterodimeric complex formed from the association of the CysD gene product with the CysNC gene product. The CysD and CysNC genes exist together in Mycobacteria as an operon.

CysD gene generally refers to a nucleic acid encoding a ATP sulfurylase. The nucleic acid may have a nucleotide sequence substantially as shown in SEQ ID No: 1 herein or otherwise having defined homology and/or identity as defined herein.

CysD protein generally refers to a ATP sulfurylase. The protein may have an amino acid sequence substantially as shown in SEQ ID No: 2 herein or otherwise having defined homology and/or identity as defined herein.

CysNC gene generally refers to a nucleic acid encoding a GTPase and APS kinase. The nucleic acid may have a nucleotide sequence substantially as shown in SEQ ID No: 3 herein or otherwise having defined homology and/or identity as defined herein.

CysNC protein generally refers to a GTPase and APS kinase. The protein may have an amino acid sequence substantially as shown in SEQ ID No: 4 herein or otherwise having defined homology and/or identity as defined herein.

Ag85B gene generally refers to a nucleic acid having a nucleotide sequence substantially as shown in SEQ ID No: 5 herein or otherwise having defined homology and/or identity as defined herein.

Ag85B protein generally refers to a protein having an amino acid sequence substantially as shown in SEQ ID No: 6 herein or otherwise having defined homology and/or identity as defined herein.

HspX promoter generally refers to a nucleic acid having a nucleotide sequence substantially as shown in SEQ ID No: 7 herein or otherwise having defined homology and/or identity as defined herein.

85BCysD generally refers to a protein having an amino acid sequence substantially as shown in SEQ ID No: 8 herein.

pHspX85BCysD generally refers to a nucleic acid having a nucleotide sequence substantially as shown in SEQ ID No: 9 herein.

B. Induction of Antigen Specific Immunity

As discussed herein, and exemplified in the examples, the inventors have shown that SAP components elicit an antigen specific protective immune response. Specifically, immunisation with SAP components, and in particular, SAC components prevents the progression of *Mycobacterium* infection in mice later infected with *M. tuberculosis*. Further, the inventors show that the SAP components can be used to boost immunity arising from BCG immunisation, and that the SAP components are highly immunoreactive in *M. tubercluosis* infected individuals, suggesting that these components are useful for minimising development of a disease or condition caused by infection. Therefore, the invention provides methods for: (i) prophylaxis; (ii) treatment; and (iii) boosting immunity to *Mycobacterium* infection. It is in these contexts that the methods of the invention minimise the likelihood of development of an infection, either by preventing the infection from developing to a relevant disease or pathology, or by preventing further development of a disease or pathology once an infection has been established.

Accordingly in one embodiment there is provided a method for minimising the likelihood of development of a *Mycobacterium* infection in an individual including:
    forming an immune response to a component of a *Mycobacterium* sulphate assimilation pathway (SAP) in an individual;
    thereby minimising the likelihood of a *Mycobacterium* infection from developing in the individual.

In one embodiment, the individual may not have a detectable *Mycobacterium* infection and/or may not have been previously immunised against *Mycobacterium*. Such an individual can generally be identified by the Mantoux test which is widely used in the art.

In another embodiment, the individual may be asymptomatic or have sub-clinical symptoms of infection. An asymptomatic subject more typically, has one or more symptoms (e.g., fever, cough, weight loss). Bacilli may be present and culturable, i.e., can be grown in culture from the above body fluids and individuals may have radiographically evident pulmonary lesions which may include infiltration but without cavitation.

In another embodiment the individual may have obvious symptoms of infection such as cavitary lesions in the lungs. Bacilli may be culturable from smears of sputum and/or the other body fluids noted above, but also present in sufficient numbers to be detectable as acid-fast bacilli in smears of these fluids.

Typically the immune response is predominantly a Th1 response. This response is determined by detecting cellular proliferation after administration of the vaccine as measured by $^3$H thymidine incorporation, or using cellular assays in which IFN-γ production is assessed, such as flow cytometry and/or ELISA. The immune response can also be measured by detecting specific antibodies (at a titer in the range of 1 to $1\times10^6$, preferably $1\times10^3$, more preferable in the range of about $1\times10^3$ to about $1\times10^6$, and most preferably greater than $1\times10^6$).

An in vitro cellular response is determined by release of a relevant cytokine such as IFN-gamma, from lymphocytes withdrawn from an animal or human currently or previously infected with virulent mycobacteria, or by detection of proliferation of these T cells. The induction is performed by addition of the polypeptide or the immunogenic portion to a suspension comprising from $1\times10^5$ cells to $3\times10^5$ cells per well. The cells are isolated from either blood, the spleen, the liver or the lung and the addition of the polypeptide or the immunogenic portion of the polypeptide result in a concentration of not more than 20 ug per ml suspension and the stimulation is performed from two to five days. For monitoring cell proliferation the cells are pulsed with radioactive labelled thymidine and after 16-22 hours of incubation the proliferation is detected by liquid scintillation counting. A positive response is a response more than background plus two standard deviations. The release of IFN-gamma can be determined by the ELISA method, which is well known to a person skilled in the art. A positive response is a response more than background plus two standard deviations. Other cytokines than IFN-gamma could be relevant when monitoring an immunological response to the polypeptide, such as IL-12, TNF-.alpha., IL-4, IL-5, IL-10, IL-6, TGF-.beta. Another and more sensitive method for determining the presence of a cytokine (e.g. IFN-gamma) is the ELISPOT method where the cells isolated from either the blood, the spleen, the liver or the lung are diluted to a concentration of preferable of 1 to $4\times10^6$ cells/ml and incubated for 18-22 hrs in the presence of the polypeptide or the immunogenic portion of the polypeptide resulting in a concentration of not more than 20 ug per ml. The cell suspensions are hereafter diluted to 1 to $2\times10^6$/ml and transferred to Maxisorp plates coated with anti-IFN-gamma and incubated for preferably 4 to 16 hours. The IFN-gamma producing cells are determined by the use of labelled secondary anti-IFN-antibody and a relevant substrate giving rise to spots, which can be enumerated using a dissection microscope. It is also a possibility to determine the presence of mRNA coding for the relevant cytokine by the use of the PCR technique. Usually one or more cytokines will be measured utilizing for example the PCR, ELISPOT or ELISA. It will be appreciated by a person skilled in the art that a significant increase or decrease in the amount of any of these cytokines induced by a specific polypeptide can be used in evaluation of the immunological activity of the polypeptide.

The immune response may be formed by providing a component of a *Mycobacterium* SAP in an individual in conditions for enabling formation of an immune response to said component in said individual. These components may be provided in various forms as discussed under the relevant subheadings below.

Recombinant BCG and other live *mycobacterium* can be delivered subcutaneously or by inhalation. The dosage regimen may also be determined by the skilled person using his expertise (e.g. single administration, repeated administration (twice or more at regular or irregular intervals), etc. This will typically also depend on the disease to be treated and the individual receiving the treatment (in bladder cancer in humans, for instance, a low-dose BCG regimen has been described as 75 mg, while a standard dose is 150 mg). However, doses of BCG as low as 1 mg have been documented to effectively support an immune response for a long period of time (5 years). In *tuberculosis*, an example of a typical dose is much lower: 0.075 mg, corresponding to 0.3-1.2 million living mycobacteria). Roughly speaking, a typical dose may fall between 0.01 μg/kg body weight and 10 mg/kg body weight. In treatment of *tuberculosis*, one treatment typically protects for a number of years. However, it is also envisaged that repeat doses are given (as is e.g. typically the case in treatment of bladder cancer).

Where the vaccine or immune stimulating composition is peptide based, the manner of application may be varied widely. Any of the conventional methods for administration of a vaccine are applicable. These include oral, nasal or mucosal application in either a solid form containing the active ingredients (such as a pill, suppository or capsule) or in a physiologically acceptable dispersion, such as a spray, powder or liquid, or parenterally, by injection, for example, subcutaneously, intradermally or intramuscularly or transdermally applied. The dosage of the vaccine will depend on the route of administration and will vary according to the age of the person to be vaccinated and, to a lesser degree, the size of the person to be vaccinated. Currently, most vaccines are administered intramuscularly by needle injection and this is likely to continue as the standard route. However, vaccine formulations which induce mucosal immunity have been developed, typically by oral or nasal delivery. One of the most widely studied delivery systems for induction of mucosal immunity contains cholera toxin (CT) or its B subunit. This protein enhances mucosal immune responses and induces IgA production when administered in vaccine formulations. An advantage is the ease of delivery of oral or nasal vaccines. Modified toxins from other microbial species, which have reduced toxicity but retained immunostimulatory capacity, such as modified heat-labile toxin from Gram-negative bacteria or *staphylococcal* enterotoxins may also be used to generate a similar effect. These molecules are particularly suited to mucosal administration.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

Where the vaccine or immune stimulating composition is a viral vector, a carrier can be any substance that does not itself induce the production of antibodies harmful to the patient receiving the composition, and which can be administered without undue toxicity. Suitable carriers can be large, slowly metabolised macromolecules such as proteins, polysaccharides, polylactic acids, polyglycolic acids, polymeric amino acids, amino acid copolymers, and inactive virus particles. Such carriers are well known to those of ordinary skill in the art. Pharmaceutically acceptable carriers can include liquids such as water, saline, glycerol and ethanol. Auxiliary substances, such as wetting or emulsifying agents, pH buffering substances, and the like, can also be present in such vehicles. Stabilizing agents such as trehalose or substances that allow water-soluble sugar glass formation at ambient temperatures may also be present. The latter includes the use of mixed soluble glass stabilisation technology in microsphere format suspended in perfluorocarbon liquids. Liposomes are also suitable carriers. A thorough discussion of pharmaceutical carriers is available in Gennaro (2000) Remington: The Science and Practice of Pharmacy. 20th ed., ISBN: 0683306472. The pharmaceutical composition is preferably sterile. It is preferably pyrogen-free. It is preferably buffered e.g. at between pH 6 and pH 8, generally around pH 7. Preferably, the composition is substantially isotonic with humans. The compositions of the invention may be administered via a variety of different routes. Certain routes may be favoured for certain compositions, as resulting in the generation of a more effective response, or as being less likely to induce side effects, or as being easier for administration. For example, the compositions utilised in this invention may be administered by any number of routes including, but not limited to, oral, intravenous, intramuscular, intra-arterial, intramedullary, intrathecal, intraventricular, transdermal or transcutaneous applications, subcutaneous, intraperitoneal, intranasal, enteral, topical, sublingual, intravaginal or rectal means. The compositions may be prepared for intranasal administration, as nasal spray, nasal drops, gel or powder, as injectables, either as liquid solutions or suspensions; solid forms suitable for solution in, or suspension in, liquid vehicles prior to injection may also be prepared. Direct delivery of the compositions will generally be accomplished by injection, subcutaneously, intraperitoneally, intravenously or intramuscularly, intranasally, or delivered to the interstitial space of a tissue. Dosage treatment may be a single dose schedule or a multiple dose schedule.

C. Determining Immunity to *Mycobacterium* Infection

In another embodiment there is provided a method for determining whether an individual is immune to a *Mycobacterium* including:

provide a component of a *Mycobacterium* SAP in an individual in conditions for enabling formation of an immune response to said component in said individual;

determining whether the individual develops a protective immune response to said component;

wherein development of a protective immune response determines that the individual is immune to a *Mycobacterium*;

thereby determining whether the individual is immune to a *Mycobacterium*.

The method is particularly useful to confirm the result of Mantoux testing, or other conventional *Mycobacterium* testing, or otherwise for further delineating a Mantoux test result, for example to identify key specificities in a particular immune response, or nature of the relevant immunogens on which the response is based. The various assays mentioned in the previous sub-heading for detecting formation of an immune response can be implemented here.

D. Vaccines and Immune Stimulating Compositions

The invention provides vaccines and immune stimulating compositions. In certain embodiments the vaccines and immune stimulating compositions are useful for providing a protective immune response to *Mycobacterium* infection, especially *M. tubercluosis* infection.

Generally, four different forms of vaccine or composition are described as follows:

(i) those that are acellular and that contain as an active ingredient for immune stimulation, a recombinant or synthetic SAP component.

(ii) those that contain as an active ingredient for immune stimulation, a cellular extract that may be enriched for a SAP component.

(iii) those that contain as an active ingredient for immune stimulation, a cell that expresses a recombinant SAP component.

(iv) those that contain a nucleic acid encoding a SAP component that on administration to an individual is expressed to form the active ingredient for immune stimulation.

(v) those that contain a viral vector encoding a SAP component that forms an active ingredient for immunisation.

A preferred immunogen in each of these forms is the CysD gene or gene product, or fragments of homologs thereof.

These forms are described in more detail below.

D.1 Acellular Compositions Containing a Recombinant or Synthetic SAP Component.

In one embodiment, the immune response is formed by providing a component of the SAP in the form of an acellular composition including isolated or recombinant SAP protein in the individual.

Generally these compositions include two key components, the first being the immunogen in the form of the recombinant or synthetic SAP component and the second being an adjuvant for potentiating an immune response to the immunogen.

Turning to the immunogen, this may include any one or more of the SAP components as described herein. Preferably the immunogen includes CysD, or an immunogenic or antigenic fragment or homolog thereof. Fragments and homologs are described in more detail below.

It will be understood that the immunogen may further include other recombinant or synthetic *Mycobacterium* antigens or immunogens. These may be provided in a form whereby they are fused to CysD by a covalent bond, where they are non covalently associated with CysD, or where they are not bound to CysD at all. Particular examples of these antigens and immunogens include Ag85B. Others are discussed in WO2009/070700.

In one embodiment, a given SAP component (such as CysD, CysNC, CysH, SirA, CysE, CysK1 proteins and their encoding genes) may have a conserved function in terms of activity in the sulphate assimilation pathway and yet have a diverged sequence. These proteins or nucleic acids are referred to as homologs.

In certain embodiments a given SAP component is one having at least 75%, preferably 80%, more preferably 85%, more preferably 90%, more preferably 95%, more preferably 98% or 99% identity to a given SAP component. For example a CysD immunogen may be one having at least 75%, preferably 80%, more preferably 85%, more preferably 90%, more preferably 95%, more preferably 98% or 99% identity to a CysD protein shown in SEQ ID No: 2. The nucleic acid sequence encoding the CysD immunogen may be one having at least 75%, preferably 80%, more preferably 85%, more preferably 90%, more preferably 95%, more preferably 98% or 99% identity to a CysD gene shown in SEQ ID No: 1.

Percent sequence identity is determined by conventional methods, by means of computer programs known in the art such as GAP provided in the GCG program package (Program Manual for the Wisconsin Package, Version 8, August 1994, Genetics Computer Group, 575 Science Drive, Madison, Wis., USA 53711) as disclosed in Needleman, S. B. and Wunsch, C. D., (1970), Journal of Molecular Biology, 48, 443-453, which is hereby incorporated by reference in its entirety. GAP is used with the following settings for polypeptide sequence comparison: GAP creation penalty of 3.0 and GAP extension penalty of 0.1. Sequence identity of polynucleotide molecules is determined by similar methods using GAP with the following settings for DNA sequence comparison: GAP creation penalty of 5.0 and GAP extension penalty of 0.3.

In another embodiment a given SAP component is provided in the form of a fragment that is capable of forming a protective immune response. These fragments are generally of sufficient length and conformation enabling presentation by the APC on Class I or II. They may be of a length ranging generally from about 8 to 15, and about 8 to 11 for Class I presentation and 11 to 15 for Class II presentation.

In order to identify relevant T-cell epitopes which are recognized during an immune response, a common method is to use overlapping peptides for the detection of MHC class II epitopes, preferably synthetic, having a length of e.g. 20 amino acid residues derived from the polypeptide. These peptides can be tested in biological assays, such as the IFN-gamma assay as described herein and those that give a positive response will be classed as immunogenic T cell epitopes. MHC class I epitopes can be identified by predicting those peptides that will bind to Class I (Stryhn, A., et al 1996 Eur. J. Immunol. 26:1911-1918) and hereafter produce these peptides synthetically and test them in relevant biological assays e.g. the IFN-gamma assay as described herein.

The peptides preferably having a length of e.g. 8 to 11 amino acid residues derived from the polypeptide. B-cell epitopes can be determined by analyzing the B cell recognition to overlapping peptides covering the polypeptide of interest as e.g. described in Harboe, M., et al 1998 Infect. Immun. 66:2; 717-723

Any of CysD, CysNC, CysH, SirA, CysE, CysK1 or related nucleic acid sequences can be made by solid phase synthesis or recombinant DNA technology.

Turning to the adjuvant, there are many examples of adjuvants known in the art. See also Allison (1998, Dev. Biol. Stand., 92:3-11; incorporated herein by reference), Unkeless et al. (1998, Annu. Rev. Immunol., 6:251-281), and Phillips et al. (1992, Vaccine, 10:151-158). Exemplary adjuvants that can be utilized in accordance with the invention include, but are not limited to, cytokines, aluminium salts (e.g., aluminium hydroxide, aluminium phosphate, etc.; Baylor et al., Vaccine, 20:S18, 2002), gel-type adjuvants (e.g., calcium phosphate, etc.); microbial adjuvants (e.g., immunomodulatory DNA sequences that include CpG motifs; endotoxins such as monophosphoryl lipid A (Ribi et al., 1986, Immunology and Immunopharmacology of bacterial endotoxins, Plenum Publ. Corp., NY, p407, 1986); exotoxins such as cholera toxin, E. coli heat labile toxin, and pertussis toxin; muramyl dipeptide, etc.); oil-emulsion and emulsifier-based adjuvants (e.g., Freund's Adjuvant, MF59 [Novartis], SAF, etc.); particulate adjuvants (e.g., liposomes, biodegradable microspheres, etc.); synthetic adjuvants (e.g., nonionic block copolymers, muramyl peptide analogues, polyphosphazene, synthetic polynucleotides, etc.); and/or combinations thereof. Other exemplary adjuvants include some polymers (e.g., polyphosphazenes; described in U.S. Pat. No. 5,500,161), Q57, saponins (e.g., QS21, Ghochikyan et al., Vaccine, 24:2275, 2006), squalene, tetrachlorodecaoxide, CPG 7909 (Cooper et al., Vaccine, 22:3136, 2004), poly[di(carboxylatophenoxy)phosphazene] (PCCP; Payne et al., Vaccine, 16:92, 1998), interferon-γ (Cao et al., Vaccine, 10:238, 1992), block copolymer P1205 (CRL1005; Katz et al., Vaccine, 18:2177, 2000), interleukin-2 (IL-2; Mbwuike et al., Vaccine, 8:347, 1990), polymethyl methacrylate (PMMA; Kreuter et al., J. Pharm. ScL, 70:367, 1981), dimethyloctadecylammonium bromide (DDA), IC31® (Vann Dissel, Vaccine, 29:2100, 2011), etc.

These compositions may also include diluents, excipients and carriers enabling administration of the composition, as known in the art.

D.2 Cell Extracts

In another embodiment, the immune response is formed by providing a component of the SAP in the form of a cell extract including an isolated or recombinant SAP protein in the individual.

Cell extracts may be obtained by known techniques, including for example sonification of a Mycobacterium strain, pelleting by centrifugation and retrieving lysate for immunisation. The lysate could be further enriched for SAP components by for example immunoaffinity chromatography. This is most useful where the strain is not recombinant for a SAP component, i.e. where the strain is not otherwise an over-expressos of, or enriched for, a SAP component. Where the strain is a recombinant strain having high levels of expression of a SAP component, a chromatographic enrichment step may not be necessary.

The cell extracts may be particularly useful as an in vitro reagent for testing efficacy of an immunisation protocol.

D.3 Recombinant or Transformed Cells

In one embodiment of the invention, the immune response is formed by providing a component of the SAP in the form of a cell including an isolated or recombinant SAP protein in the individual.

It is particularly preferred that the cell is a *Mycobacterium*, and in particular a *M. tubercluosis* strain, especially an attenuated *M. tuberculosis* strain capable of forming a live attenuated vaccine. A 'live attenuated vaccine' as used herein is a vaccine containing live or viable micro-organisms with reduced virulence (attenuated); as opposed to an inactivated vaccine.

Other types of *mycobacterium* include members of the *Mycobacterium tuberculosis* complex (Taxon identifier 77643 in the UniProt or NCBI taxonomy database), which includes the species *M. tuberculosis* (the major cause of human *tuberculosis*), *M. bovis*, *M. bovis* BCG (the strain most often used for vaccination purposes), *M. africanum, M. microti, M. canetti*, and *M. pinnipedii*.

Preferably the cell is a BCG strain. Those of skill in the art will recognize that several suitable BCG strains exist which are suitable for use in the practice of the invention, including but not limited to those designated ATCC® Number:

27289 *Mycobacterium bovis* BCG, Chicago 1 [B; BCGT; tice]

27291 *M. bovis*

35731 *M. bovis* TMC 1002 [BCG Birkhaug]

35732 *M. bovis* TMC 1009 [BCG Swedish]

35735 *M. bovis* TMC 1012 [BCG Montreal; CIP 105920]

35736 *M. bovis* TMC 1013 [BCG Brazilian]

35737 *M. bovis* TMC 1019 [BCG Japanese]

35738 *M. bovis* TMC 1020 [BCG Mexican]

35739 *M. bovis* TMC 1021 [BCG Australian]

35741 *M. bovis* [BCG Glaxo]

35742 *M. bovis* TMC 1025 [BCG Prague]

35744 TMC 1029 [BCG Phipps]

35745 *M. bovis* TMC 1030 [BCG Connaught]

35746 *M. bovis* TMC 1101 [BCG Montreal, SM-R]

35747 *M. bovis* TMC 1103 [BCG Montreal, INH-R; CIP 105919]

35748 *M. bovis* TMC 1108 [BCG Pasteur SM-R]

27290 *M. bovis* [BCG Copenhagen H]

19274 *M. bovis* deposited as zrculosis subspecies bovis 50 [BCG]

19015 *Mycobacterium* sp. d<i as *M. bovis* Karlson and Lessel BCG

35733 *M. bovis* TMC 1010 [BCG Danish, SSI 1331] and

35734 *M. bovis* TMC 1011 [BCG Pasteur], etc.

It will be understood that the recombinant mycobacteria of the invention need not be confined to strains of BCG. Those of skill in the art will recognize that other *Mycobacterium* strains may also be employed, examples of which include but are not limited to: *M. tuberculosis* CDC1551 strain (See, e.g. Griffith et at., Am. J. Respir. Crit. Care Med. August; 152(2):808; 1995), *M. tuberculosis* Beijing strain (van Soolingen et al., J CHn Microbiol. December:33(12): 3234-8, 1995) H37Rv strain (ATCC#:25618), *M. tuberculosis* pantothenate auxotroph strain (Sambandamurthy et al., supra; *M. tuberculosis* rpo V mutant strain (Collins et al., Proc Natl Acad Sci USA. 92(17):8036; 1995), *M. tuberculosis* leucine auxotroph strain (Hondalus et al., Infect. Immun. 68(5):2888; 2000), etc., or other attenuated and/or recombinant strains derived from *M. tuberculosis*. Other candidate bacteria include other members of the *M. tuberculosis* complex, other mycobacteria (e.g. *M. africanum* or *M. avium* complex bacteria), or other mycobacterial species.

In this form of the invention, SAP component may be over-expressed, i.e. the protein may be expressed at a level that exceeds that of a suitable control organism, such as the same *mycobacterium* that has not been genetically engineered to over-express the SAP component. Those of skill in the art are well acquainted with comparative measurements of protein activity, and with the use of suitable standards and controls for such measurements.

The over-expression of the SAP component may be carried out by any suitable method known in the art. Generally, the method will involve linking nucleic acid sequences encoding the SAP component to a particular promoter or other regulatory element that is activated when the strain is introduced into a cell especially an APC. Those of skill in the art will recognize that many such expression control sequences are known and would be suitable for use in the invention. For example, if constitutive expression of SAP component is desired, expression control sequences (e.g. promoters and associated sequences) including but not limited to: *mycobacterium* optimal promoter (mop, George et al., 1995); blaF promoter (Timm et al., 1994); hsp60, ace or msp12 promoters; etc., with or without an optimized ribosomal binding site.

Alternatively, over-expression of SAP may not be constitutive but may instead be inducible, in response to an environmental cue. For example, expression of the protein may be driven by a promoter that is induced in a particular location or in response to an environmental stimulus, examples of which include but are not limited to: macrophage inducible promoter (which drives expression of genes that are specifically upregulated within the macrophage phagosome, see Schannapinger et al. JEM 2003); acetamidase promoter (Mahenthiralingam et al., J. Gen. Microbiol. 1993), and tetracycline-inducible (Blokpoel et al., Nucl. Acids Res. 33(2):e22, 2005), etc.

In addition, promoters from other species maybe utilized, examples of which include but are not limited to: various viral promoters, whereby after "gene therapy-like" strategies (e.g. co-inoculation of mycobacteria, and an engineered virus) the Mtb antigens are expressed in selected tissues infected by the co-administered virus; etc.

As a further alternative, native or naturally occurring SAP promoters may be altered by mutation to cause over-expression of SAP component.

Those of skill in the art will recognize that several avenues are available to introduce nucleic acid sequences encoding the SAP component, in operable linkage with one or more expression control sequences, into a mycobacterial host where over-expression will occur. For example, the sequences may be included in a vector that is subsequently introduced into the *mycobacterium*. Many vectors suitable for containing and expressing genes are known, and include but are not limited to various extra-chromosomal elements such as plasmids, e.g. those comprising the pAL500 origin of replication, modified to augment their copy number; or other plasmids with origins of replication that are or will be developed; or extrachromosomal elements that do not replicate or integrate into mycobacterial genome but provide a suicidal source for homologous recombination to occur; etc. Introduction of such a vector into a *mycobacterium* may be carried out by any of several known methods suitable for that particular vector, including but not limited to electroporation and mycobacteriophage-mediated transduction for homologous recombination. In a preferred embodiment, the vector is a plasmid and the method that is used is electroporation.

In other embodiments of the invention, the SAP component is over-expressed from the *M. tuberculosis* chromosome. Those of skill in the art will recognize that various molecular biology strategies exist for generating a *mycobacterium* with this property. For example, various mutations may be introduced into the chromosome (randomly or in a directed fashion) that result in over-production of the SAP component by the bacterium. Alternatively, nucleic acid sequences that include one or more expression control sequences operably linked to nucleic acid sequences encoding the SAP component may be introduced into the bacterial chromosome, e.g. by transduction with a suicide plasmid with or without a means for counter-selection, to provide sequences for homologous recombination.

In a particularly preferred embodiment of the invention, there is provided an expression vector including:
a nucleic acid encoding a *Mycobacterium* antigen for providing an antigen specific immune response to *Mycobacterium* infection;
a promoter operably linked to the nucleic acid for expression of the nucleic acid when the strain is introduced into an APC, said promoter having a sequence of a *Mycobacterium* promoter that causes immediate and sustained expression of a *Mycobacterium* antigen when said promoter is introduced into an APC.

In the above described embodiments, the *Mycobacterium* HspX promoter is a preferred promoter for use as a promoter having the sequence of a *Mycobacterium* promoter that causes expression of a *Mycobacterium* ATP independent chaperone. Specifically, as exemplified in Example 2 here, this promoter is capable of inducing high and sustained expression of a SAP component in a BCG strain. Other examples of promoters useful in the invention include Rv0962c. Rv0971c. Rv0983. Rv0986. Rv2428.Rv1130. Rv2626c as described in Fontan et al. 2008 Infect. & Immun. 76:pp 717.

Vaccine formulation under this subheading involves studies to determine maximum bacterial viability and stability throughout the manufacturing process. This includes determination of maximum organism viability (live to dead) during culture utilizing a variety of commonly used medium for the culture of Mycobacteria to include the addition of glycerol, sugars, amino acids, and detergents or salts. After culture cells are harvested by centrifugation or tangential flow filtration and resuspended in a stabilizing medium that allows for protection of cells during freezing or freeze-drying process. Commonly used stabilizing agents include sodium glutamate, amino acids or amino acid derivatives, glycerol, sugars or commonly used salts. The final formulation will provide sufficient viable organisms to be delivered by intradermal, percutaneous injection, perfusion or oral delivery with sufficient stability to maintain and adequate shelf life for distribution and use.

Prior to administration to humans as a vaccine, the BCG strains described under this subheading are tested according to methods that are well-known to those of skill in the art. For example, tests for toxicity, virulence, safety, etc. are carried out in suitable animal models, e.g. in mice, guinea pigs, etc., some of which are immunocompromised. The ability of the vaccine preparations to elicit an immune response is likewise typically tested in suitable animal models, e.g. mice, guinea pigs, etc. In addition, protection studies involving vaccination, boosting, and subsequent challenge with live Mtb may be carried out using suitable animal models such as mice, guinea pigs, and non-human primates. Finally, those of skill in the art are familiar with the arrangements for carrying out clinical trials in consenting humans, in order to test the efficacy of the vaccine preparations. For details, see, for example, U.S. Pat. No. 7,625,572 (Sun et al.) and references cited therein.

D.4 Nucleic Acid Vaccines

In another embodiment, the immune response is formed by providing a component of the SAP in the form of or a nucleic acid encoding a SAP protein in the individual.

In particular, as exemplified Example 1, the inventors have shown that protective immunity can be provided by administering a DNA vaccine containing a gene encoding CysD in mice challenged with *M. tubercluosis*.

The nucleic acid may be provided in linearised or circular form for injection. Generally the nucleic acid will have a promoter enabling expression of the SAP component in the relevant cell. For example, where the administration is to muscle tissue, the vector will contain a promoter capable of activation by muscle transcription factors and enhancers. In these embodiments, it is generally understood that the muscle cell will produce the relevant SAP component which will then be phagocytosed by an APC such as a dendritic cell for presentation to a T cell, upon which immunity is established.

D.5 Viral Vectors

In another embodiment, the immune response is formed by providing a component of the SAP in the form of a viral vector that contains a nucleic acid that encodes the component, or that expresses a component of the SAP.

Examples of suitable vectors include those based on a vaccinia genome and those based on an adenovirus genome.

Some of the compositions described under the above subheadings may be formulated as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, ethanol and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration.

It will be understood that the invention disclosed and defined in this specification extends to all alternative combinations of two or more of the individual features mentioned or evident from the text or drawings. All of these different combinations constitute various alternative aspects of the invention.

EXAMPLES

Example 1

*M. tuberculosis* can survive in a broad spectrum of environments, including high levels of oxidative stress, low pH and nutrient deprivation ((Nathan, 2000 #29). Exposure and adaption of *M. tuberculosis* to these conditions during infection requires the coordinated regulation of gene expression ((Timm, 2003 #93). Genes involved in the metabolism of sulphur have consistently been identified as up-regulated in conditions that mimic the macrophage environment ((Pinto, 2004 #14; #35; Muttucumaru, 2004 #34; Manganelli, 2002 #75; Hampshire, 2004 #33; Betts, 2002 #49) and during macrophage infection ((Schnappinger, 2003 #31).

These genes encode enzymes of the sulphate assimilation pathway (SAP) of *M. tubercluosis*, required for the reduction of sulphur. Indeed, sulphur-containing compounds are fundamental in a wide range of biological activities. In its reduced form sulphur is used in the biosynthesis of the amino acid cysteine, one of the prime targets for reactive nitrogen intermediates encountered by *M. tubercluosis* in the intracellular environment ((Rhee, 2005 #92). Cysteine can be subsequently incorporated into mycothiol which functions analogously to glutathione ((Fan, 2009 #197) and is crucial to *M. tuberculosis* within the granuloma in regulating the redox balance upon encountering free radicals released by host cells. Mutants of *Mycobacterium smegmatis* in which mycothiol biosynthesis has been abrogated exhibit high-level resistance to isoniazid and are more susceptible than wild-type strains to oxidative stress and antibiotics ((Rawat, 2002 #82; Buchmeier, 2003 #85). This first line of defence by *M. tuberculosis* therefore is linked to the availability of cysteine and as such has been shown to be required for the organism's surivial ((Sareen, 2003 #84; Buchmeier, 2006 #83; Newton, 2002 #81). Reinforcing this increased need for cysteine in the macrophage environment, is the up-regulation of ATP sulfurylase, the first enzyme in the SAP, upon exposure to oxidative stress ((Pinto, 2004 #14; #35; Schnappinger, 2003 #31). Disabling the biosynthesis of cysteine attenuates bacterial virulence and persistence during the chronic phase of infection in mice ((Senaratne, 2006 #3).

Although members of the SAP appear to be highly expressed under conditions presumably encountered within the host, it is not known if these proteins constitute immunogenic components of *M. tuberculosis*. Most focus has been on secreted proteins of mycobacteria, as these are predicted to be recognized by early host immune responses ((Andersen, 1992 #202; Roberts, 1995 #203). Sulphate reduction takes place within the cell and for this reason SAP enzymes are either intracellular or membrane bound components ((de Souza, 2011 #206; Bhave, 2007 #205; Schelle, 2006 #204) and would not be detected in screens for immunogenic secreted antigens of *M. tuberculosis* ((Andersen, 1992 #202). In this report we demonstrate that members of the SAP are highly immunogenic components of *M. tubercluosis*, being recognised by *M. tubercluosis* infected individuals and conferring protective immunity in a murine model of TB. Our results suggest that SAP members are potential candidates for inclusion into new TB vaccines.

Materials and Methods

Bacterial Strains and Growth Conditions.

*Escherichia coli* K-12 and BL21 (DE3) were grown in Luria-Bertani (LB) broth or agar (Sigma-Aldrich). *M. tubercluosis* H37Rv or strain MT103 ((Jackson, 1999 #208) were grown in Middlebrook 7H9 medium (Difco Laboratories) supplemented with 0.5% glycerol, 0.05% Tween 80, and 10% albumin-dextrose-catalase (ADC) or on solid Middlebrook 7H11 medium (Difco Laboratories) supplemented with oleic acid—ADC. All cultures were grown at 37° C. with or without shaking. Antibiotics were added to media when required at 25 µg/mL for kanamycin and 100 µg/mL for ampicillin. Non-replicating persistence of in vitro grown *M. tubercluosis* was achieved by adding daily 50 µM of the nitric oxide-donating compound 2,2'-(Hydroxynitrosohydrazono)bis-ethanamine (DETA-NO) (Sigma) using the method of ((Bryk, 2008 #36). At day 0, 1, 3 and 7 bacterial counts were determined for these cultures and at day 7, RNA was extracted from both cultures for real-time (RT) PCR analysis.

Protein Antigens and DNA Vaccines

Culture Filtrate protein (CFP) was obtained from the NIH Biodefense and Emerging Infections Research Resources Repository (NR-14825). Concavalin A (ConA) was purchased from Sigma-Aldrich. Purification of SAP protein antigens and construction of DNA vectors encoding SAP genes are described in supplementary table 1.

Macrophage Infection and Real-Time PCR

The RAW264.7 mouse macrophage cell line was grown in RPMI (Gibco-BRL) supplemented with 10% fetal calf serum (FCS; Gibco-BRL) and 2 mM L-glutamine (Invitrogen) (Complete RPMI), at 37° C. in 5% $CO_2$. Adhered RAW264.7 cells were infected with *M. tubercluosis* at a multiplicity of infection of 1:1. Four hours post-infection, macrophage monolayers were washed with phosphate buffered saline (PBS), cells were incubated for an additional 48 hours in fresh medium and total RNA was extracted for RT PCR analysis.

*M. tubercluosis* pellets from broth culture or *M. tubercluosis*-infected macrophages were resuspended in TRI reagent (Invitrogen) and disrupted with 0.1-mm zirconia/silica beads in a BioSpec Products Bead Beater. RNA was extracted, treated with TURBO DNase (Ambion) and resuspended in DPEC-treated water (Invitrogen) as described previously ((Muttucumaru, 2004 #34). cDNA was synthesised from 1 µg of total RNA by using Superscript III reverse transcriptase (Invitrogen). Quantitive RT-PCR was performed using 4 µL of cDNA, SYBR green I PCR Master Mix (Qiagen) and 5 µM of the gene-specific primer pair (supplementary table 1) in a reaction volume of 25 µL. PCR reactions were run on a Rotogene 6000-series sequence detector (Corbett research) in triplicate per primer pair. Relative expression levels were determined using the comparative threshold cycle method of Livak and Schmittgen ((Livak, 2001 #99) using the non-induced *M. tubercluosis* 16S rRNA (encoded by rrs) asB the control ((Banaiee, 2006 #101).

Human Studies

Subjects:

15 *M. tubercluosis*-infected, HIV negative patients were recruited from the TB clinic at Royal Prince Alfred Hospital, Missenden Rd, NSW, Australia. Peripheral blood mononuclear cells (PBMCs) were obtained from biopsy or culture-proven patients of varying ages and gender that had or had not yet started anti-TB treatment. Ethical approval for this study was given by Sydney South West Area Health Service (protocol number: X06-0248). Patients were compared with 11 healthy tuberculin skin test negative (TST-ve) individuals.

T Cell Proliferation Assay:

PBMCs from whole blood were isolated on a Ficoll gradient (Histopaque-1077, Sigma Aldrich). $2.5 \times 10^5$ cells/well of PBMCs were incubated at 37° C. in 5% $CO_2$ for 5 days in the presence of 10 µg/mL of the SAP proteins, 10 µg/mL of CFP, Ag-85B or 3 µg/mL of ConA. T cell proliferation was assayed by $^3$H-thymidine incorporation (MP Biomedicals, 1 µCi/well) at day 5 using liquid scintillation spectroscopy (Microbeta Luminescence Counter, Wallace). The lymphocyte stimulation index (SI) was calculated using the following formula: average counts per minute (cpm) in the presence of antigen/average cpm in the absence of antigen. A SI of greater than or equal to 3 was considered a positive response to antigen. Murine studies Six- to eight-week-old female C57BL/6 mice were obtained from Animal Resources Centre (Perth, Australia) and maintained in specific pathogen-free conditions. For determination of immunogenicity, mice (4/group) were infected via the intra-nasal (i.n) route with $5 \times 10^4$ colony forming units (CFU) of *M. tuberculosis* Mt103. Three and 8 weeks post-infection single cell suspensions were prepared from the mediastinal lymph node (MLN) of immunized mice in complete RPMI medium and the number of interferon (IFN)-γ-producing cells was determined by ELISpot as described previously ((Palendira, 2002 #210) using SAP enzymes, CFP and Ag85B at a concentration of 10 µg/ml with ConA used at 3 µg/ml. For the analysis of protective efficacy, mice (5/group) were immunised subcutaneously (s.c) once with either $5 \times 10^5$ CFU of *M. bovis* BCG, or 3 times at 2 week intervals with 10 µg of CysDNC protein co-administered with dimethyl dioctadecyl ammoniumbromide (DDA) (1.25 mg/ml) and monophosphoryl lipid A (MPL) (125 µg/ml) or intramuscularly (i.m) with 100 µg DNA vaccine per injection. Eight weeks after the final vaccination, mice were challenged with aerosol *M. tuberculosis* Mt103 using an inhalation exposure apparatus (Glas-Col) with an infective dose of □100 viable bacilli per lung. Bacterial load was determined 4 weeks after challenge by plating homogenates of lung and spleen.

Statistical Analysis

For assessment of protective efficacy, the significance of differences was evaluated by one-way ANOVA with pair-wise comparison of multi-grouped data sets achieved using the Bonferroni post hoc test. For assessment of induction of host immune responses by SAP enzymes of infected mice or *M. tuberculosis* infected individuals compared to uninfected mice or TST-ve individuals respectively, the Mann-Whitney's U test was used (*$P<0.05$).

Results

Induction of *M. Tubercluosis* ATP Sulfurylase mRNA in the Intracellular Environment Correlates with Potent Antigen-Specific Immunity.

Figure 1:
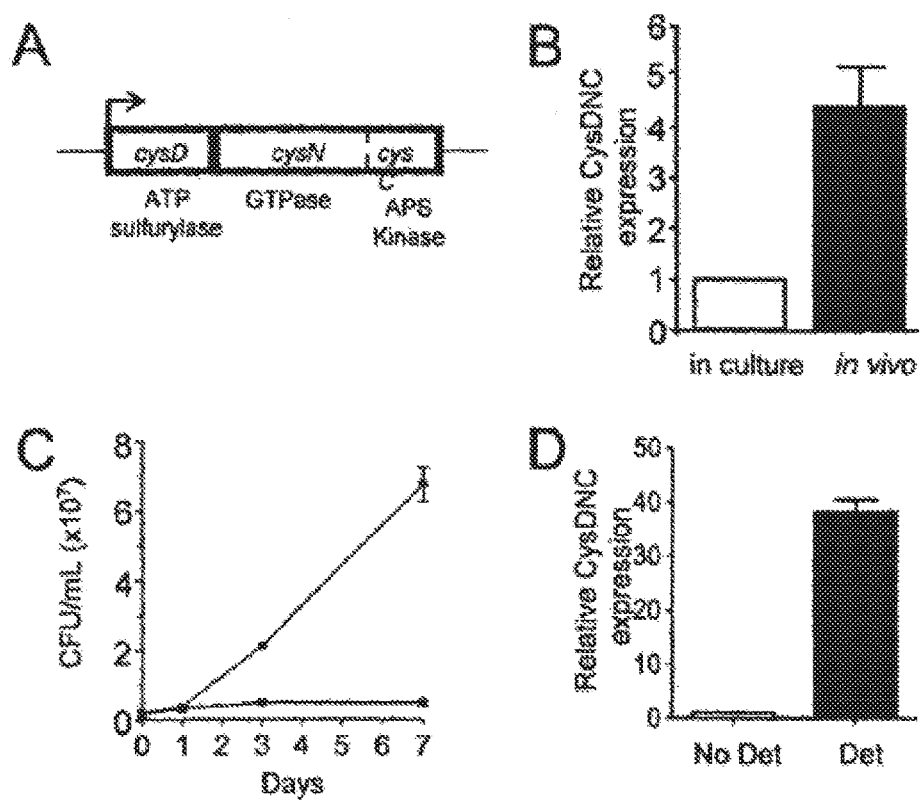
FIG. 1. Up-regulation of the *M. tuberculosis* sulphate-activation complex within host cells and during non-replicating persistence. (A) Genetic organisation of the cysDNC locus encoding the sulphate activation complex. In *M. tubercluosis* the cysN (GTPase) and cysC (kinase) activities are fused together in one polypeptide and cysDNC constitute an operon. (B) Relative expression level of cysDNC, measured by quantitative real time PCR, of bacilli grown for 48 hours in culture (clear bar) or 48 hours post infection of RAW cells (black bar). Data is the mean relative expression±S.E.M measured in triplicate and is representative of two independent experiments. (C) Effect of DETA-NO (Det) on growth of cultured *M. tuberculosis*. 50 µM DETA-NO was added to *M. tubercluosis* culture (filled squares) every 24 hours for 7 days or left untreated (filled circles). At days 0, 1, 3 and 7, aliquots were taken to determine CFU/mL. (D) Relative expression level of cysDNC (black bar) at day 7 post DETA-NO treatment compared to the untreated *M. tuberculosis* culture (clear bar).

The sulphate activating complex (SAC) of *M. tuberculosis* is the first step in the SAP (FIG. 15) and constitutes 3 catalytic activities, ATP sulfurylase, GTPase and APS kinase activity encoded by the CysDNC operon (FIG. 1A). The ability of *M. tubercluosis* SAC to up-regulate its expression in culture conditions that mimic intracellular stress ((Pinto, 2004 #14), suggests that its expression may also be induced in the intracellular environment. To test this, we examined the changes in CysDNC mRNA levels within RAW264.7 cells during *M. tuberculosis* infection. We found that expression of CysDNC was significantly enhanced, displaying an approximately 4.4-fold increase over the level found in broth-cultured bacilli during the first 48 hours (FIG. 1B). We also determined if expression of CysDNC was induced in non-replicating bacteria in order to mimic conditions encountered during latent infection. Using the nitric oxide donor DETA-NO ((Bryk, 2008 #156) we were able to inhibit *M. tubercluosis* replication in vitro compared to non-treated bacteria (FIG. 1C). *M. tuberculosis* CysDNC was highly up-regulated under conditions of non-replicating persistence and demonstrated a 35-fold increase in gene expression compared to actively growing mycobacteria (FIG. 1D). This implies that CysDNC may be involved in the ability of *M. tubercluosis* to adapt to the variety of stresses encountered in the intracellular environment and progression to the latent state.

As CysDNC was induced at high levels within the intracellular environment and in non-replicating bacteria, we hypothesized that the enzyme may be recognized by the immune response during *M. tuberculosis* infection. To test this, we intranasally infected mice with *M. tubercluosis* and examined the frequency of IFN-γ secreting cells in the mediasteinal lymph nodes (MLN). At three weeks post infection, stimulation of MLN cells with CysDNC ex vivo resulted in a strong induction of IFN-γ secreting T cells, which was similar to levels induced by the immuno-dominant secreted Ag85B protein of *M. tubercluosis* (FIG. 2A). This strong T cell response was maintained up to eight weeks post infection (FIG. 2B). Similar patterns of antigen-specific IFN-γ secreting cellular responses in response to CysDNC and Ag85B were observed in the lung (data not shown). In addition, lymphocyte proliferation assays of human PBMCs revealed that CysDNC was recognized during human *M. tubercluosis* infection (FIG. 2C). CysDNC responses were similar to that upon recall to Ag85B yet lower than that induced by CFP. However CysDNC significantly induced proliferation of PBMCs from TB patients compared to TST-ve individuals (FIG. 2C). These results indicate that *M. tubercluosis* CysDNC, encoding ATP sulfurylase is a potent immuno-stimulatory antigen of *M. tubercluosis*.

Protective Immunity Against Virulent *M. Tubercluosis* Challenge Following Vaccination with DNA Encoding ATP Sulfurylase.

The enhanced expression of the genes encoding ATP sulfurylase in the intracellular environment (FIG. 1B), in our non-replicating persistence model (FIG. 1C) and the ability of this protein complex to induce a robust antigen specific Th1 type cytokine response ex vivo (FIG. 2) may render the encoded products effective targets for anti-mycobaterial protective immunity. To determine this, mice were immunised with DNA vectors expressing cysD and/or cysNC and aerosol challenged with *M. tuberculosis*. Immunisation with all vectors expressing either cysD or cysNC resulted in significantly reduced bacterial load compared to mice vaccinated with the control vector, in both the lung (FIG. 3A) and spleen (FIG. 3B) ($p<0.01$). In all experiments, there was an increasing trend for DNA-cysD to afford better protective efficacy than DNA-cysNC in the lung, while using a combination of DNA-cysD and DNA-cysNC equalled the protection seen with DNA-cysD alone. The protective efficacy was significantly greater in the spleen when mice were immunised with a combination of these two plasmids, and this protection approached the level achieved with BCG (FIG. 3B). Therefore ATP sulfurylase is a highly protective component of *M. tuberculosis*.

Downstream Enzymes of *M. Tubercluosis* Sulphate Assimilation Pathway (SAP) are Immunogenic Components of *M. Tubercluosis*.

The promising results obtained with *M. tubercluosis* ATP sulfurylase (CysDNC) led us to question whether other members of the SAP are targets of the host immune response. We found that all SAP proteins tested were significantly up-regulated in the intracellular environment, with CysK1 mRNA displaying the highest induction of approximately 6.7 fold (FIG. 4A). The level of induction was similar for SirA and CysH while CysK1 and CysE also displayed similar levels of intracellular up-regulation. This is in agreement with the fact the SirA and CysH are located within the same operon in the *M. tuberculosis* genome ((Cole, 1998 #225) while CysK1 and. CysE lie adjacent in the genome ((Cole, 1998 #225; Schnell, 2007 #87). We also determined that these proteins are recognized in *M. tuberculosis* infected mice, as all proteins induced IFN-γ secreting T cells at 8 weeks post-infection (FIG. 4B). Like CysDNC (FIG. 2C), lymphocyte proliferation assays on human PBMCs revealed that all SAP enzymes studied were recognized during human *M. tubercluosis* infection (FIG. 4C).

As expression of all SAP enzymes was up-regulated in vivo and the proteins were recognized in mice and humans, we assessed if they could improve the protective efficacy afforded by DNA-CysDNC. When mice were vaccinated with DNA-CysDNC together with DNA encoding cysH, sirA, cysK1 and cysE, we did not observe increases in protective efficacy compared to DNA-CysDNC: alone both in the lung (FIG. 5A) or spleen (FIG. 5B). Therefore while all SAP members were recognized by the immune response in *M. tubercluosis* infected humans and mice, CysDNC alone afforded maximal protective efficacy in the mouse model used here.

Boosting BCG Vaccinated Mice with ATP Sulfurylase Improves Protection Afforded by BCG in the Lung Against Challenge with *M. Tubercluosis*.

Considering the strong recognition of C ATP sulfurylase by TB patients and its protective effect in mice, we determined if this protein complex may be a suitable candidate to boost the protective effect of BCG upon *M. tuberculosis* challenge. After low dose, aerosol delivery of *M. tubercluosis*, naive mice demonstrated substantial bacterial growth in the lungs and dissemination to spleens were detected (FIGS. 6A and 6B). In contrast, immunisation with BCG alone resulted in significant protection against *M. tuberculosis* challenge with an approximate 1.5-$\log_{10}$ reduction in the *M. tubercluosis* load in the lung and spleen (FIGS. 6A, 6B). Boosting with CysDNC protein led to a further significant reduction compared to vaccination with BCG alone of 0.5-log 10 *M. tubercluosis* in the lung (FIG. 6A). While bacterial burden was reduced in the spleen with boosting, this difference did not achieve significance (FIG. 6B). Therefore CysDNC is able to improve the protective effect of the BCG against *M. tuberculosis* infection, which was most apparent in the lung.

Discussion

The identification of new targets of host immunity would markedly aid efforts to develop more effective TB vaccines. In this report we identify the sulphate activation complex (SAC) of *M. tuberculosis* as a major antigenic component of the *bacillus*. The SAC is an enzyme complex with 3 catalytic activities ((Pinto, 2004 #14; Sun, 2005 #13). This complex is predicted to play a role in adaption of *M. tuberculosis* to the host cell environment, due to up-regulation of CysDNC within macrophages (FIG. 1B) ((Schnappinger, 2003 #31), and in response to a number of in vitro stress conditions including nutrient starvation and oxidative stress ((Hatzios, 2011 #167; Pinto, 2004 #14). Therefore it is possible that strong recognition of CysDNC by both TB patients (FIG. 2C) and *M. tuberculosis*-infected mice (FIGS. 2A&B) may be due to the enhanced expression of CysDNC within the host. Intriguingly, CysDNC also displayed significant up-regulation in a model of non-replicating growth of *M. tubercluosis* (FIG. 1D). This result implies that CysDNC-expression may be required for the adaption of *M. tubercluosis* to the latent state during chronic infection. This is supported by the role of reduced sulphur compounds in the onset of chronic *M. tubercluosis* infection ((Senaratne, 2006 #3) and corresponds to the sustained recognition of CysDNC by T cells at late-stages of *M. tubercluosis* infection in mice (FIG. 2B). This further implies that *M. tuberculosis* CysDNC may contribute to the organism's survival in a state of non-replicating persistence by sustaining metabolic pathways that utilize cysteine. Cysteine is incorporated into Acetyl CoA, the building block for lipids in the organism's cell wall and a substrate for the glyoxylate shunt, a pathway required for *M. tubercluosis* to persist in macrophages and in mice ((McKinney, 2000 #211). Further, CysDNC is up-regulated during low-oxygen dormancy ((Voskuil, 2004 #35) and plays a role in the suppression of apoptosis by macrophages ((Danelishvili, 2010 #116), implying a role for CysDNC in evasion of the host immune response. Interestingly cysD was found to be up-regulated after exposure to anti-TB drugs that are bactericidal to non-replicating bacteria ((Fu, 2009 #117; Heifets, 2005 #120; Tasneen, 2008 #12 I).

Figure 3:
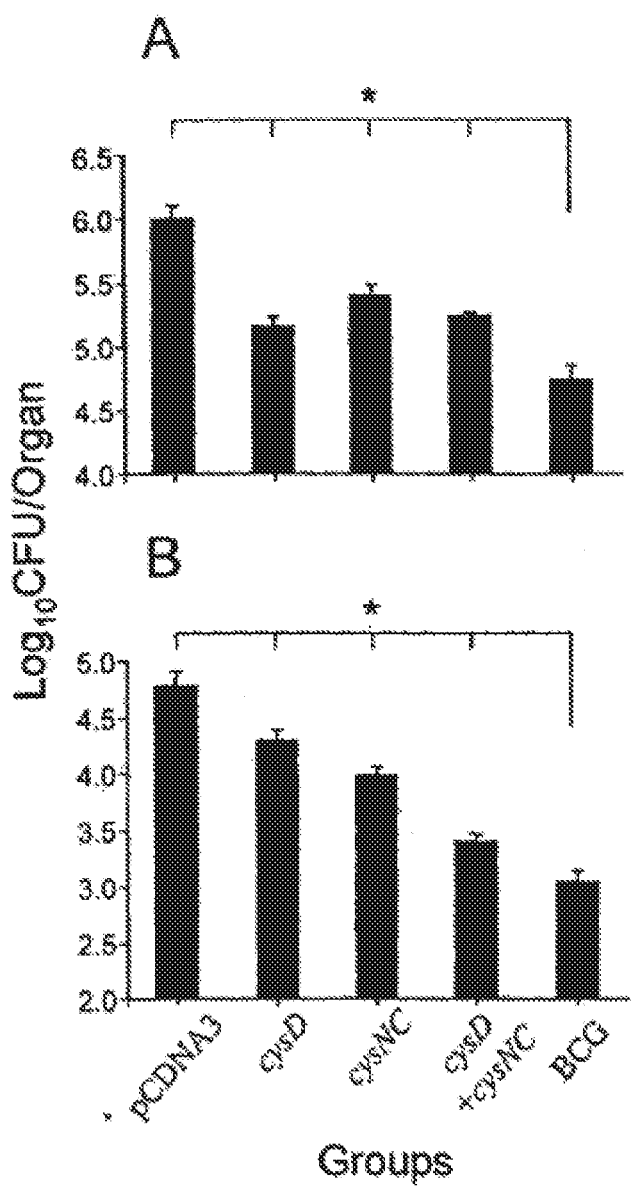

Enhanced recognition of mycobacterial antigens by the host immune response does not always correlate protection against challenge with virulent *M. tubercluosis* in animal models ((Gartner, 2007 #215; Kamath, 1999 #143; Skinner, 2003 #115). We therefore assessed if CysDNC was protective in our low-dose murine model of aerosol *M. tubercluosis* infection. When delivered as DNA vaccines, CysD and CysNC were protective as single components in both the lung and spleen, and a combination of the two constructs achieved a level of protection similar to that induced by BCG (FIG. 3). Thus the strong expression of genes encoding CysDNC correlates with the protective effect of the antigenic complex in the models used here. However, addition of DNA vaccines encoding other components of the SAP did not improve the protective effect of CysDNC, despite the fact that proteins were recognised by PBMCs from TB patients, were up-regulated within macrophages and induced strong IFN-☐ responses from T cells of *M. tubercluosis*-infected mice (FIG. 4). It is unclear as to why CysDNC appears to be dominant member of the SAP in terms of protective efficacy, but may relate to MHC-restricted responses based on the mouse strain used in this study. It is also of interest to note that the SAP antigens are proposed to be intracellular or membrane-associated proteins due to their function in sulfur metabolism ((de Souza, 2011 #206), and we have confirmed this for some of the members by Western blot (not shown). However, all *M. tubercluosis* antigens in clinical trials are secreted proteins, as these are predicted to be the early targets of host immunity ((Kaufmann, 2011 #196). This study suggests that non-secreted proteins may also be suitable components of new TB vaccine formations. Further, the recent identification of stress-induced, latency-associated antigens improving protection at late-stages post *M. tuberculosis* infection ((Aagaard, 2011 #213) warrants further testing of CysDNC in similar models, considering the marked induction of the protein complex in non-replicating bacteria and in response to in vitro stress.

An important property of potential subunit vaccines is the capacity to 'boost' protection with prior BCG immunization, as this is the proposed role for such vaccines in new TB vaccine schedules ((Kaufmann, 2011 #196). A handful of proteins have demonstrated an ability to boost BCG-induced protection in experimental *M. tuberculosis* infection ((Lu, 2011 #144; Dey, 2011 #145; Rouanet, 2009 #214). CysDNC can now be added to this list, as the antigen complex was able to significantly increase the protective effect of BCG alone in the lung, the primary site of infection in the model used (FIG. 6).

In addition to defining the antigenic role of the SAP proteins, this study has also expanded our knowledge of regulation of SAP gene expression during infection. All components of the SAP tested displayed up-regulation within the macrophage cell line used here. This adaptation to the phagosome environment is an indication of the bacterium's ability to supply cysteine to the cell in a timely fashion, which has been extensively reviewed by Hatzios and Bertozzi ((Hatzios, 2011 #167). It may be that enzymes in the SAP regulate the expression of each other. For instance serine acetyl transferase has been shown to associate and form a complex with the last enzyme in the pathway o-acetylserine sulthydralase (OASS) ((Droux, 1998 #218).

Figure 2:
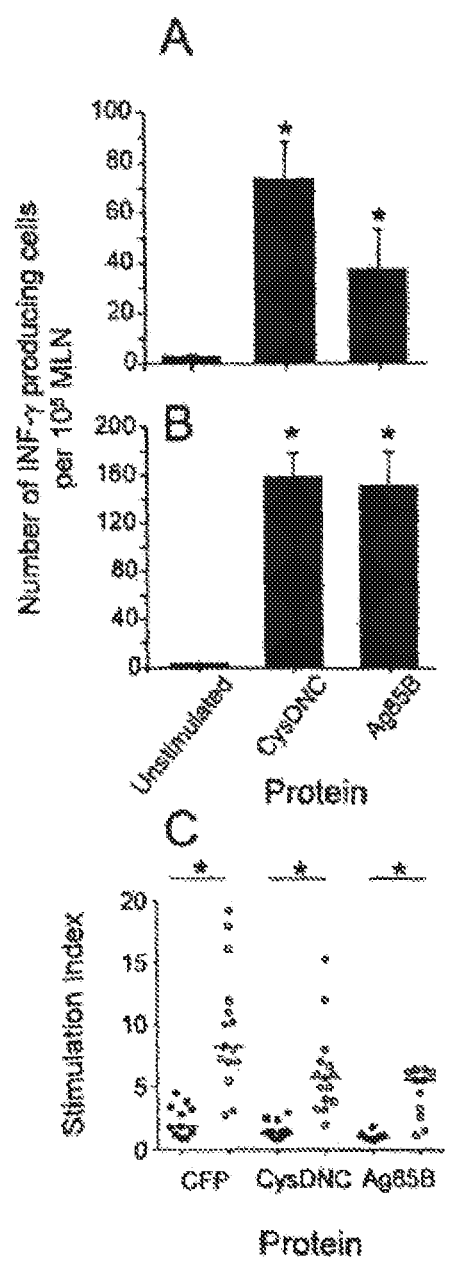
FIG. 2. Host immune recognition of the *M. tuberculosis* sulphate-activation complex. Antigen-specific T cell responses in the MLN of mice were measured 3. (A) and 8 (B) weeks following intranasal *M. tubercluosis* challenge. IFN-γ secreting cells were enumerated by ELIspot following recall to CysDNC or 85B proteins (10 µg/ml). Data are the means±S.E.M. for four mice and are representative of duplicate experiments. The significance of differences between protein-stimulated and unstimulated cells was determined by ANOVA; *p<0.0001. (C) Antigen-specific T cell responses were measured in the peripheral blood of *M. tuberculosis* infected patients (open circles) (n=15) and TST-ve individuals (filled circles) (n=11). T cell proliferation in response to *M. tubercluosis* CFP, CysDNC and Ag85B proteins at 10 µg/ml was measured via the incorporation of $^3$H-thymidine and a stimulation index calculated. Horizontal lines represent the median for each group. Significance of difference's between *M. tubercluosis* infected patients and TST-ve individuals was determined by the Mann-Whitney U test; *p<0.001.

While this interaction negatively regulates OASS ((Mino, 2000 #222; Schnell, 2007 #87), similar to ATP-sulfurylase, it's expression and activity may depend on the requirement for cysteine ((Kredich, 1966 #219; Mino, 1999 #220; Mino, 2000 #221; Pinto, 2004 #14). Further more, *E. coli* ATP sulfurylase forms a tight complex with, OASS ((Wei, 2002 #96) and it is this complex that can activate sulphate to produce APS (FIG. 15). It has been suggested that given the similarities between *E. coli* and *M. tubercluosis* ATP sulfurylases, that the mycobacterial system also forms a higher order complex, linking catalytic functions with other enzymes in the SAP ((Sun, 2005 #13). This has not been formally tested, however, it may be the reason why all of the enzymes of the SAP induce robust host immune responses (FIG. 2, FIGS. 4B &C). Also highlighting the regulation of sulphur metabolism genes is their enhanced transcription upon exposure to various antibiotics which may influence how *M. tubercluosis* responds to these drugs ((Hatzios, 2011 #167). Presumably drug-responsive genes encode proteins that are relevant to the drugs mode of action, and many sulphur-metabolising enzymes are promising drug targets ((Bhave, 2007 #1).

In summary, we have identified components of the SAP as host-cell induced proteins that are major antigenic components of *M. tubercluosis*.

Example 2

The preferred niche within the host of virulent mycobacteria and the attenuated BCG vaccine strain is the intracellular environment of the macrophage. It has been observed that mycobacteria also have the ability to infect and persist within DCs and stimulate in vivo T cell responses [8,9].

We hypothesized that the targeted expression of antigen by recombinant (r) BCG within DCs may influence the subsequent generation of antigen-specific immunity. We considered that the promoter controlling expression of the *M. tuberculosis* hspX gene may be a suitable candidate to direct expression of antigen to APCs after vaccination with BCG.

HspX, or α-crystallin protein, is a member of the small molecular weight heat-shock proteins that act as ATP-independent chaperones [10,11]. The hspX promoter is rapidly induced upon entry of *M. tuberculosis* into cultured macrophages [12]. The gene is also up-regulated in vitro by hypoxia [12], during stationary phase of growth of aerated *M. tuberculosis* cultures [11] and by addition of NO donors [13], which may all represent conditions encountered by *M. tubercluosis* within host cells. Importantly, the hspX gene is up-regulated after infection of mice with virulent *M. tuberculosis* [14].

In this report, we demonstrate that the hspX promoter can be used to modulate expression of antigens expressed by rBCG, and antigen expression is rapidly induced upon entry of rBCG within DCs. Use of the hspX promoter to control antigen expression resulted in accelerated priming of antigen-specific T cells and sustained in vivo generation of antigen-reactive T cells after vaccination.

Materials and Methods

Bacterial Strains, Media and Antigens

*M. tuberculosis* 1437Rv (ATC27294) and *M. bovis* BCG (Pasteur strain) were grown on Middlebrook 7H9 medium (Difco, BD) supplemented with 0.5% glycerol, 0.05% Tween-80 and 10% ADC or on solid Middlebrook 7H11 medium (Difco, BD) supplemented with OADC. When required, the antibiotic kanamycin (Km) was added at a concentration of 20 μ/ml.

Mice

Six to eight weeks old C57BL/6 mice were obtained from. Animal Resources Centre (Perth, WA, Australia) and maintained in specific pathogen-free conditions. The p25 CD4+ TCR transgenic (specific for residues 240-254 of Ag85B) were obtained from Prof. K. Takatsu (University of Tokyo, Japan) and Prof. J. Ernst (New York University School of Medicine, NY) [15] and were backcrossed onto B6.SJL/Ptprca to obtain the p25+CD45.1+ line. Animal experiments were performed with approval of the University of Sydney Animal Care and Ethics Committee.

Construction of Recombinant (r)BCG Strains

BCG expressing GFP under control of the M. tubercluosis hspX promoter (BCG:$P_{hspX}$-GFP) was constructed by transformation of plasmid pMV306:GFP into BCG, which was a kind gift of Professor Cliff Barry, Tuberculosis Research Section, NIAID, National Institutes of Health, Rockville, Md. To develop BCG in which the hspX promoter drives expression of the Ag85B protein, the Ag85B protein-encoding fbpB gene was amplified from M. tuberculosis genomic DNA and used to replace the gfp gene in pMV306:GFP, resulting in the intermediate vector pJEX88. The $P_{hspX}$-fbpB fragment was excised by digestion with XbaI and HpaI and ligated to the shuttle-vector pMV261 [16] digested with the same enzymes. The resultant plasmid was transformed into BCG to produce BCG:$P_{hspX}$-85B. Control BCG used in this study was either BCG Pasteur strain or BCG Pasteur transformed with pMV261 [16]. Construction of rBCG overexpressing the M. tuberculosis Ag85B protein under the control of the hsp60 promoter (BCG:$P_{hsp60}$-85B) has been described previously [17].

Dendritic Cell Infections

DCs were prepared form the bone marrow of mice as described previously [18]. For DC infection, 4-day old DC cultures were incubated with rBCG strains at a multiplicity of infection of 5:1 or 1:1. After 4 h, extracellular bacteria were removed by extensive washing and at 6 and 24 h post-infection, DCs were lysed and bacteria collected for flow cytometry (LSR-II, Becton Dickinson, San Jose, Calif., USA). The fold increase in fluorescence was determined by dividing the fluorescence of bacteria populations at 6 and 24 h by the initial value (day 0). For visualisation by confocal microscopy, similar infection conditions were used, except DCs were allowed to adhere onto round 25 mm coverslips (Leica Microsystems, Wetzlar, Germany) prior to rBCG infection and then viewed under the LP5 Confocal microscope (Leica).

In Vitro Immunogenicity Assays

Four-day DC culture (1×105 cells) were infected with Rbcg strains at an MOI of 5:1. CD4 T cells were purified from p25+CD45.1+ mice by autoMACS separation (Miltenyi Biotec, Bergisch Gladbach, Germany) and 5×105 purified T cells cultured with infected DCs. Three days following co-incubation, supernatant were assayed for IFN-γ by ELISA as described previously [19] and T cell proliferation was measured by [3H]-thymidine uptake.

In Vivo Immune Response

To detect GFP expression in vivo, C57BL/6 mice were inoculated with 1×107 CFUs of fluorescent rBCG strains subcutaneously in the footpads. Tissue of the local inflammatory site was obtained immediately after infection or at days 1, 3 or 7 post-infection. Tissues were digested with collagenase and DNAse for at least 1 h and then strained to recover cells. Cells were stained with CD45-APCCy7, CD11b-APC and CD11c-PE-Cy7 (BD Pharmingen). Stained cells were analysed using the LSR-II flow cytometer (BD).

For determination of T cell priming after rBCG delivery, lymph node cells from p25+CD45.1+ mice were prepared and labelled with Carboxyfluorescein succinimidyl ester (CFSE; Molecular Probes, Invitrogen, USA). C57BL16 mice received 5×105 CFSE-labelled p25 lymph node cells i.v. and the next day were immunized subcutaneously with 5×105 CFU rBCG strains. At 3 or 7 days postvaccination organs were processed and the CFSE profile of dividing cells analysed.

For determination of rBCG immunogenicity, C57BL/6 mice were subcutaneously vaccinated with 5×105 CFUs of rBCG strains. At 3 and 12 weeks post-vaccination, splenocytes were recovered and 2×105 splenocytes were cultured with p25 peptide (3 μg/ml) at 37° C. in 5% $CO_2$. Eighteen hours following co-incubation, the number of IFN-γ secreting cells was determined by ELIspot as described previously [19] and at 72 h following the antigen challenge, T cell proliferation was assessed by [3H]-thymidine uptake.

Protective Efficacy

For assessment of protective efficacy, C57BL/6 mice (5 per group) were immunised with 5×105 CFU of BCG strains and at 12 weeks post-vaccination mice were challenged with aerosol M. tuberculosis H37Rv using a Middlebrook airborne infection apparatus (Glas-Col, Terre Haute, Ind., USA) with an infective dose of approximately 100 viable bacilli per lung. Four weeks after the challenge the number of bacteria within the lung and spleen was enumerated on Middlebrook 7H11 Bacto agar.

Statistical Analysis

The significance of differences for linear and log-transformed assays was determined by analysis of variance (ANOVA) using Bonferroni's Multiple Comparison test was used for pair-wise comparison of multi-grouped data sets. Differences with $p<0.05$ were considered significant.

Results

Induction of the M. Tuberculosis hspX Promoter within Dendritic Cells

We hypothesized that targeting antigen expression to DCs during mycobacterial infection would have a positive effect on the resultant immune response directed towards the antigen. In order to induce expression of foreign genes within DCs, we constructed BCG strains in which the M. tubercluosis hspX promoter ($P_{hspX}$) controlled gene expression. BCG:$P_{hspX}$-GFP, in which gfp was expressed using $P_{hspX}$, displayed marked up-regulation of GFP fluorescence only when grown in non-aerated cultures, confirming up-regulation of the hspX promoter under low oxygen tension (FIG. 7A). After infection of DCs for 24 h with BCG:$P_{hspX}$-GFP, isolated bacteria exhibited a dramatic increase in fluorescence when compared to the initial inoculum (day 0) or bacteria isolated 6 h post-infection (FIG. 7B). Visualisation of GFP fluorescence by confocal microscopy confirmed the induction of hspX-controlled expression of GFP within rBCG-infected DCs (FIG. 7C). These results demonstrate that the hspX promoter can be used to drive rapid and pronounced induction of gene expression by recombinant BCG within DCs.

Early In Vivo Induction of hspX-Induced Expression after Vaccination

In order to determine if the hspX promoter could be used to drive antigen expression in vivo, mice were vaccinated with BCG:$P_{hspX}$GFP and the presence of GFP host cells determined. GFP+ cells were detected as early as 1 day post-vaccination, and were prominent at days 3 and 7 post-vaccination (FIG. 8A). The proportion of GFP+ cells peaked at day 3 post-vaccination, however there were no significant differences between the three timepoints examined (FIG. 8B). We also detected an influx of CD11c$^{hi}$CD11b$^{hi}$ DCs to the site of rBCG vaccination, with numbers peaking at day 7 postvaccination (FIG. 9A). GFP$^+$ DCs were prominent at later stages of infection, with a significant number of DCs harbouring BCG:P$_{hspX}$GFP in an induced state at day 3 and day 7 respectively (FIGS. 9B and C). These data indicate that vaccination with BCG:P$_{hspX}$-GFP results in infection of DCs and rapid intracellular induction of the hspX promoter.

Use of the hspX Promoter to Drive Expression of Foreign Antigens in BCG

To determine if the hspX promoter could be used to modulate immunity to defined antigens, we expressed the gene encoding the immunodominant *M. tubercluosis* Ag85B antigen under the control of this promoter. Although a homologue of this protein is expressed by BCG, improved anti-Ag85B immunity is conferred on BCG by constitutive over-expression of the antigen [17.] The BCG:P$_{hspX}$-85B strain displayed up-regulation of Ag85B expression in cultures grown under conditions of limited aeration (data not shown). To determine if hspX-mediated expression influences presentation of Ag85B by DCs, in vitro cultured DCs from mouse bone marrow were infected with BCG:P$_{hspX}$-85B, BCG alone or BCG:P$_{hsp60}$-85B, in which Ag85B is constitutively expressed under the control of the strong hsp60 promoter [17]. Infected cells were cultured with transgenic Ag85B-specific CD4$^+$ T cells (p25 T cells [15]) and proliferation and cytokines release examined. DCs infected with all 3 strains induced p25 T cell proliferation (FIG. 10A) and IFN-γ secretion (FIG. 10B), which was not observed in uninfected cells. Responses were more prominent in DCs infected with BCG:P$_{hspX}$-85B, and this difference reached significance in T cell proliferation assays (FIG. 10A). Therefore the hspX promoter can be used to drive foreign antigen expression in BCG, and induction within DCs results in improved T cell proliferation in vitro.

Augmented In Vivo T Cell Immunity Induced by Vaccination with BCG:P$_{hspX}$-85B The in vitro immunogenicity experiments suggested that use of the hspX promoter might be able to modify BCG-induced immunity in vivo. Considering the rapid induction of expression driven by the hspX promoter after vaccination (FIG. 8), we first determined if vaccination with BCG:P$_{hspX}$-85B led to improved early priming of Ag85B reactive T cells compared to BCG alone or BCG:P$_{hsp60}$-85B. To do this, CFSE-labelled p25 T cells were transferred into wild-type recipients, and the activation and proliferation of the transferred cells examined after vaccination with BCG strains. At day 3 post-infection, BCG:P$_{hspX}$-85B vaccination had induced p25 T cells to proliferate, with most divided cells displaying an CFSE intermediate or low profile, while vaccination with BCG alone or BCG:Phsp60-85B did not result in appreciable proliferation (FIGS. 11A and B). At day 7 post-infection all BCG strains induced proliferation of the majority of transferred p25 T cells as determined by the CSFE profile of p25 CD4$^+$ T cells (FIG. 11A) with approximately 90% of p25 CD4 T cells displaying a CSFE low profile after vaccination with BCG, BCG:Phsp60-85B or BCG:P$_{hspX}$-85B (FIG. 11B). Taken together, these results indicate that induction of Ag85B in BCG:P$_{hspX}$-85B accelerates the initial priming of p25 T cells, however both BCG and BCG:P$_{hsp60}$-85B produced sufficient antigen to result in proliferation of p25 T cells at later timepoints.

We next assessed the long-term T cell responses by vaccinating mice with the three BCG strains and examining the generation of Ag85B-sepecific T cells at either 3 or 12 weeks post-vaccination. At 3 weeks post-vaccination, both BCG:P$_{hsp60}$-85B and BCG:P$_{hspX}$-85B led to the increased generation of Ag85B-specific IFN-γ-secreting cells compared to BCG alone, with BCG:P$_{hspX}$-85B in particular increasing the number of responding cells by approximately 5-fold compared to control BCG (FIG. 12A). At 12 weeks post-vaccination both BCG and BCG:P$_{hsp60}$-85B displayed equivalent levels of IFN-γ-secreting cells responding to Ag85B, which were significantly greater than that observed in unvaccinated mice (FIG. 12B). However, in mice vaccinated with BCG:P$_{hspX}$-85B the number of antigen specific IFN-γ-secreting cells was approximately 6 times greater than that induced by BCG alone and more than 3 times the response observed after vaccination with BCG:Phsp60-85B (FIG. 12B). These results indicate that the ability to induce Ag85B expression within host cells results in a pattern of increased in vivo T cell immunity, which is most evident at extended timepoints postvaccination.

Since Ag85B is an immunodominant antigen of *M. tuberculosis*, we determined if rBCG expressing Ag85B under control of the hspX promoter can improve the protective effect of BCG against *M. tuberculosis* infection. Twelve weeks post-vaccination, mice were challenged with low dose *M. tuberculosis* strain H37Rv via the aerosol route. The bacterial load in both the lungs (FIG. 12C) and the spleen (FIG. 12D) at 4 weeks post *M. tubercluosis* infection were significantly reduced in all mice vaccinated with BCG strains compared to unvaccinated mice. However, the protective effect was similar in mice vaccinated with BCG alone, BCG:P$_{hspX}$-85B, BCG:P$_{hsp60}$-85B, indicating that in this model Ag85B overexpression did not improve protective efficacy.

Discussion

The BCG vaccine displays variable protective efficacy against *tuberculosis*, however the vaccine can be engineered to express foreign molecules in a functional form, and this has driven the development of BCG as a recombinant vector to protect against infectious diseases and malignancies such as cancer [20]. Critical to the success of such approaches is the ability to modulate BCG-induced immunity to generate the desired immune response. In this report, we show that the *M. tuberculosis* hspX promoter can be used to modulate expression of recombinant antigens produced in BCG. We demonstrate that the hspX promoter is rapidly induced in vitro within DCs (FIG. 6), which complements existing literature on hspX expression within macrophages [21] and the uptake of BCG by DCs after infection of mice [8]. This rapid and pronounced in vivo induction of the hspX promoter within DCs is important for the use of this antigen carrier system due to the critical role of DCs in the initiation of mycobacterial immune responses [8,22,23]. We also demonstrate that hspX promoter activity is evident within DCs from rBCG-vaccinated mice as early as 24 h post-infection (FIG. 8). This rapid promoter induction appears to contradict with hspX transcript levels after low-dose aerosol *M. tuberculosis* infection of mice, with hspX mRNA detected only at approximately 15 days post-infection and most prevalent at later stages [14]. This suggests that in vivo hspX accumulation in *M. tuberculosis* may be a slow process, or could also relate to the delivery of a high rBCG dose used in the current study and the sensitive GFP reporting system facilitating the detection of hspX promoter activity.

In order to determine the antigen-specific effects of P$_{hspX}$-driven expression, we made use of the hspX promoter to modulate expression of *M. tuberculosis* Ag85B, a secreted mycobacterial protein that is a component of a number of candidate *tuberculosis* vaccines [24]. We observed that the early recruitment of DCs to the infection site and rapid phagocytosis of BCG (FIG. 9) correlated with enhanced priming and activation of Ag85B-reactive T cells after vaccination with BCG:P$_{hspX}$-85B (FIGS. 10 and 11). Further, this improved T cell priming resulted in sustained generation of IFN-γ-secreting cells recognising Ag85B up to 3 months postvaccination. Intriguingly, expression of the gene encoding Ag85B is down-regulated during chronic *M. tuberculosis* infection in mice [14], and it would be of interest to determine if vaccines which use the native Ag85B promoter to drive antigen expression in BCG can sustain long-term protective immunity in humans [25]. We also used a murine model of aerosol *M. tuberculosis* infection to determine if in vivo induction of Ag85B could improve the protective effect of the BCG vaccine. However, we did not observe an improved protective effect compared to BCG alone (FIG. 12). In a previous study, we similarly observed that overexpression of Ag85B in BCG does not improved the protective effect of BCG, despite increasing anti-Ag85B immunity in vaccinated mice [17]. This suggests that other antigens may need to be assessed in this system to determine the effect of P$_{hspX}$-driven expression in BCG to protect against *M. tubercluosis* infection, or alternatively BCG:P$_{hspX}$-85B should be assessed in other pre-clinical models of *tuberculosis* where Ag85B expression doe impart some level of improved protective efficacy when expressed in rBCG [25].

The mechanism of improved and sustained immunity due to up-regulation of antigen via the hspX promoter is unclear. Constitutive over-expression of Ag85B using the mycobacterial hsp60 promoter leads to very strong expression levels in rBCG as detected by western blotting [17] and is superior to BCG alone at stimulating antigen specific T cell immunity early after vaccination, however this effect is not sustained long-term (FIGS. 12A and 12B). It is possible that P$_{hsp60}$ transcription is down-regulated at later stages of BCG infection, thus resulting in reduced antigen levels at extended timepoints, or instability of the promoter in vivo reduces immunogenicity [26]. Conversely, P$_{hspX}$ activity appears to be maximal at longer timepoints post-infection [14], indicating that this approach may result in heightened and sustained levels of antigen expression by BCG:P$_{hspX}$-85B. It has been previously reported that Ag85B overexpression in BCG leads to improved autophagy and, improved capacity of the rBCG strain to stimulate antigen-specific T cell responses [27]. When we inhibited autophagy in rBCG-infected. DCs using 3-methyladenine and determined the extent of activation of Ag85B specific T cells, we observed a trend of reduced T cell activation in treated DCs infected with BCG:P$_{hspX}$-85B, however this effect did not reach statistical significance in all experiments (data not shown).

The results presented in the current study demonstrate that the capacity to induce antigen expression using rBCG as the carrier leads to significant and sustained generation of cellular immune responses. This has clear implications for diseases that require 'Th1' like responses for their control, such as *tuberculosis*.

Example 3

Methods

C57BL/6 mice (n=5) were immunized 3 times by s.c injection with either adjuvant (MPL/DDA), Ag85B-CysD fusion protein (10 mg) or Ag85B (10 mg). At the time of the first injection of protein vaccines, mice were immunized once by s.c injection with 5×10$^5$ CFU of BCG. Four weeks following the third immunization, mice were challenged with aerosol *M. tubercluosis* with an infective dose of ~100 viable bacilli per lung.

Results

Bacterial load was determined in the lung (FIG. 14A) and the spleen (FIG. 14B) 4 weeks after immunised mice were challenged with aerosol *M. tubercluosis*. Data are shown as the mean CFU (±SEM) per organ. The significance of the differences between groups was evaluated by one-way ANOVA with pair-wise comparison of multi-grouped data sets achieved using the Bonferroni post hoc test.

Vaccination with Ag85B-CysD resulted in protection equivalent to the existing BCG vaccine. This is a remarkable result considering BCG expresses a large number of antigenic targets, yet our fusion of two antigens is equally protective (FIG. 14).

REFERENCES

1. Dye, C. and B. G. Williams, *The population dynamics and control of tuberculosis*. Science, 2010. 328(5980): p. 856-61.
2. Kaufmann, S. H., *Fact and fiction in tuberculosis vaccine research: 10 years later*. The Lancet infectious diseases, 2011. 11(8): p. 633-40.
4. Timm, J., et al., *Differential expression of iron-, carbon-, and oxygen-responsive mycobacterial genes in the lungs of chronically infected mice and tuberculosis patients*. Proc Natl Acad Sci USA, 2003. 100(24): p. 14321-6.
5. Pinto, R., et al., *The Mycobacterium tuberculosis cysD and cysNC genes form a stress-induced operon that encodes a tri-functional sulfate-activating complex*. Microbiology, 2004. 150(Pt 6): p. 1681-6.
6. Banaiee, N.; W. R. Jacobs, Jr., and J. D. Ernst, *Regulation of Mycobacterium tuberculosis whiB3 in the mouse lung and macrophages*. Infect Immun, 2006. 74(11): p. 6449-57.
7. Muttucumaru, D. G., et al., *Gene expression profile of Mycobacterium tuberculosis in a non-replicating state*. Tuberculosis (Edinb), 2004. 84(3-4): p. 239-46.
8. Manganelli, R., et al., *Role of the extracytoplasmic-function sigma factor sigma(H)in Mycobacterium tuberculosis global gene expression*. Mol Microbiol, 2002. 45(2): p. 365-74.
9. Hampshire, T., et al., *Stationary phase gene expression of Mycobacterium tuberculosis following a progressive nutrient depletion: a model for persistent organisms?* Tuberculosis (Edinb), 2004. 84(3-4): p. 228-38.
10. Betts, J. C., et al., *Evaluation of a nutrient starvation model of Mycobacterium tuberculosis persistence by gene and protein expression profiling*. Mol Microbiol, 2002. 43(3): p. 717-31.
11. Schnappinger, D., et al., *Transcriptional Adaptation of Mycobacterium tuberculosis within Macrophages: Insights into the Phagosomal Environment*. J Exp Med, 2003. 198(5): p. 693-704.
12. Rhee, K. Y., et al., *S-nitroso proteome of Mycobacterium tuberculosis: Enzymes of intermediary metabolism and antioxidant defense*. Proc Natl Acad Sci USA, 2005. 102(2): p. 467-72.
13. Fan, F., et al., *Structures and mechanisms of the mycothiol biosynthetic enzymes*. Current opinion in chemical biology, 2009. 13(4): p. 451-9.
14. Rawat, M., et al., *Mycothiol-deficient Mycobacterium smegmatis mutants are hypersensitive to alkylating agents, free radicals, and antibiotics*. Antimicrob Agents Chemother, 2002. 46(11): p. 3348-55.

15. Buchmeier, N. A., et al., *Association of mycothiol with protection of Mycobacterium tuberculosis from toxic oxidants and antibiotics*. Mol Microbiol, 2003. 47(6): p. 1723-32.

16. Sareen, D., et al., *Mycothiol is essential for growth of Mycobacterium tuberculosis Erdman*. J Bacteriol, 2003. 185(22): p. 6736-40.

17. Buchmeier, N. and R. C. Fahey, *The mshA gene encoding the glycosyltransferase of mycothiol biosynthesis is essential in Mycobacterium tuberculosis Erdman*. FEMS Microbiol Lett, 2006. 264(1): p. 74-9.

18. Newton, G. L. and R. C. Fahey, *Mycothiol biochemistry*. Arch Microbiol, 2002. 178(6): p. 388-94.

19. Senaratne, R. H., et al., *5'-Adenosinephosphosulphate reductase (CysH) protects Mycobacterium tuberculosis against free radicals during chronic infection phase in mice*. Mol Microbiol, 2006. 59(6): p. 1744-53.

20. Andersen, P., et al., *Identification of immunodominant antigens during infection with Mycobacterium tuberculosis*. Scandinavian journal of immunology, 1992. 36(6): p. 823-31.

21. Roberts, A. D., et al., *Characteristics of protective immunity engendered by vaccination of mice with purified culture filtrate protein antigens of Mycobacterium tuberculosis*. Immunology, 1995. 85(3): p. 502-8.

22. de Souza, G. A., et al., *Bacterial proteins with cleaved or uncleaved signal peptides of the general secretory pathway*. Journal of proteomics, 2011.

23. Bhave, D. P., W. B. Muse, 3rd, and K. S. Carroll, *Drug targets in mycobacterial sulfur metabolism*. Infectious disorders drug targets, 2007. 7(2): p. 140-58.

24. Schelle, M. W. and C. R. Bertozzi, *Sulfate metabolism in mycobacteria*. Chembiochem: a European journal of chemical biology, 2006. 7(10): p. 1516-24.

25. Jackson, M., et al., *Persistence and protective efficacy of a Mycobacterium tuberculosis auxotroph vaccine*. Infection and immunity, 1999. 67(6): p. 2867-73.

26. Bryk, R., et al., *Selective killing of nonreplicating mycobacteria*. Cell Host Microbe, 2008. 3(3): p. 137-45.

27. Livak, K. J. and T. D. Schmittgen, *Analysis of relative gene expression data using real-time quantitative PCR and the 2(-Delta Delta C(T)) Method*. Methods, 2001. 25(4): p. 402-8.

28. Palendira, U., et al., *Coexpression of interleukin-12 chains by a self-splicing vector increases the protective cellular immune response of DNA and Mycobacterium Bovis BCG vaccines against Mycobacterium tuberculosis*. Infection and immunity, 2002. 70(4): p. 1949-56.

29. Cole, S. T., et al., *Deciphering the biology of Mycobacterium tuberculosis from the complete genome sequence*. Nature, 1998. 393(6685): p. 537-44.

30. Schnell, R., et al., *Structural insights into catalysis and inhibition of O-acetylserine sulfhydrylase from Mycobacterium tuberculosis. Crystal structures of the enzyme alpha-aminoacrylate intermediate and an enzyme-inhibitor complex*. J Biol. Chem, 2007. 282(32): p. 23473-81.

31. Sun, M., et al., *The trifunctional sulfate-activating complex (SAC) of Mycobacterium tuberculosis*. J Biol Chem, 2005. 280(9): p. 7861-6.

32. Hatzios, S. K. and C. R. Bertozzi, *The regulation of sulfur metabolism in Mycobacterium tuberculosis*. PLoS pathogens, 2011. 7(7): p. e1002036.

33. McKinney, J. D., et al., *Persistence of Mycobacterium tuberculosis in macrophages and mice requires the glyoxylate shunt enzyme isocitrate lyase*. Nature, 2000. 406 (6797): p. 735-8.

34. Voskuil, M. L, K. C. Visconti, and G. K. Schoolnik, *Mycobacterium tuberculosis gene expression during adaptation to stationary phase and low-oxygen dormancy*. Tuberculosis (Edinb), 2004. 84(3-4): p. 218-27.

35. Danelishvili, L., et al., *Secreted Mycobacterium tuberculosis Rv3654c and Rv3655c proteins participate in the suppression of macrophage apoptosis*. PLoS One, 2010. 5(5): p. e10474.

37. Heifets, L., J. Simon, and V. Pham, *Capreomycin is active against non-replicating M. tuberculosis*. Ann Clin Microbiol Antimicrob, 2005. 4: p. 6.

38. Tasneen, R., et al., *Enhanced bactericidal activity of rifampin and/or pyrazinamide when combined with PA-824 in a murine model of tuberculosis*. Antimicrob Agents Chemother, 2008. 52(10): p. 3664-8.

39. Gartner, T., et al., *Mucosal prime-boost vaccination for tuberculosis based on TLR triggering OprI lipoprotein from Pseudomonas aeruginosa fused to mycolyl-transferase Ag85A*. Immunology letters, 2007. 111(1): p. 26-35.

40. Kamath, A. T., et al., *Co-immunization with DNA vaccines expressing granulocyte-macrophage colony-stimulating factor and mycobacterial secreted proteins enhances T-cell immunity, but not protective efficacy against Mycobacterium tuberculosis*. Immunology, 1999. 96(4): p. 511-6.

41. Skinner, M. A., et al., *A DNA prime-live vaccine boost strategy in mice can augment IFN-gamma responses to mycobacterial antigens but does not increase the protective efficacy of two attenuated strains of Mycobacterium bovis against bovine tuberculosis*: Immunology, 2003. 108(4): p. 548-55.

42. Aagaard, C., et al., *A multistage tuberculosis vaccine that confers efficient protection before and after exposure*. Nature medicine, 2011. 17(2): p. 189-94.

43. Lu, J., et al., *Immunogenicity and Protective Efficacy against Murine Tuberculosis of a Prime-Boost Regimen with BCG and a DNA Vaccine Expressing ESAT-6and Ag85A Fusion Protein*. Clin Dev Immunol, 2011. 2011: p. 617892.

44. Dey, B., et al., *Latency Antigen alpha-Crystallin Based Vaccination Imparts a Robust Protection against TB by Modulating the Dynamics of Pulmonary Cytokines*. PLoS One, 2011. 6(4): p. e18773.

45. Rouanet, C., et al., *Subcutaneous boosting with heparin binding haemagglutinin increases BCG-induced protection against tuberculosis*. Microbes and infection/Institut Pasteur, 2009. 11(13): p. 995-1001.

47. Droux, M., et al., *Interactions between serine acetyltransferase and O-acetylserine (thiol) lyase in higher plants—structural and kinetic properties of the free and bound enzymes*. European journal of biochemistry/FEBS, 1998. 255(1): p. 235-45.

48. Mino, K., et al., *Characteristics of serine acetyltransferase from Escherichia coli deleting different lengths of amino acid residues from the C-terminus.* Bioscience, biotechnology, and biochemistry, 2000. 64(9): p. 1874-80.
49. Kredich, N. M. and G. M. Tomkins, *The enzymic synthesis of L-cysteine in Escherichia coli and Salmonella typhimurium.* The Journal of biological chemistry, 1966. 241(21): p. 4955-65.
50. Mino, K., et al., *Purification and characterization of serine acetyltransferase from Escherichia coli partially truncated at the C-terminal region.* Bioscience, biotechnology, and biochemistry, 1999. 63(1): p. 168-79.
51. Wei, J., et al., *Cysteine biosynthetic enzymes are the pieces of a metabolic energy pump.* Biochemistry, 2002. 41(26): p. 8493-8.
[1] Nchinda G, Kuroiwa J, Oks M, Trumpfheller C, Park C G, Huang Y, et al. The efficacy of DNA vaccination is enhanced in mice by targeting the encoded protein to dendritic cells. J Clin Invest 2008 April; 118(4):1427-36.
[2] Ryan A A, Wozniak T M, Shklovskaya E, O'Donnell M A, Fazekas de St Groth B, Britton W J, et al. Improved protection against disseminated *tuberculosis* by *Mycobacterium bovis* bacillus Calmette-Guérin secreting murine GM-CSF is associated with expansion and activation of APCs. J Immunol 2007; 179(December (12)):8418-24.
[3] Lozza L, Rivino L, Guarda G, Jarrossay D, Rinaldi A, Bertoni F, et al. The strength of T cell stimulation determines IL-7 responsiveness, secondary expansion, and lineage commitment of primed human CD4(+)IL-7R(hi) T cells. Eur J Immunol 2008; 38(January (1)):30-9.
[4] Ohara N, Yamada T. Recombinant BCG vaccines. Vaccine 2001; 19(30):4089-98.
[5] Alexandroff A B, Jackson A M, O'Donnell M A, James K. BCG immunotherapy of bladder cancer: 20 years on. Lancet 1999; 353(9165):1689-94.
[6] Ristori G, Buzzi M G, Sabatini U, Giugni E, Bastianello S, Viselli F, et al. Use of Bacille Calmette-Guerin (BCG) in multiple sclerosis. Neurology 1999; 53(October (7)): 1588-9.
[7] Kodama S, Davis M, Faustman D L. The therapeutic potential of tumor necrosis factor for autoimmune disease: a mechanistically based hypothesis. Cell Mol Life Sci 2005; 62(August (16)):1850-62.
[8] Jiao X, Lo-Man R, Guermonprez P, Fiette L, Deriaud E, Burgaud S, et al. Dendritic cells are host cells for mycobacteria in vivo that trigger innate and acquired immunity. J Immunol 2002; 168(February (3)): 1294-301.
[9] Wolf A J, Linas B, Trevejo-Nunez G J, Kincaid E, Tamura T, Takatsu K, et al. *Mycobacterium tuberculosis* infects dendritic cells with high frequency and impairs their function in vivo. J Immunol 2007; 179(August (4)):2509-19.
[10] Chang Z, Primm T P, Jakana J, Lee I H, Serysheva I, Chiu W, et al. *Mycobacterium tuberculosis* 16-kDa antigen (Hsp16.3) functions as an oligomeric structure in vitro to suppress thermal aggregation. J Biol Chem 1996; 271(12):7218-23.
[11] Yuan Y, Crane D D, Barry 3rd C E. Stationary phase-associated protein expression in *Mycobacterium tuberculosis*: function of the mycobacterial alpha-crystallin homolog. J Bacteriol 1996; 178(15):4484-92.
[12] Yuan Y, Crane D D, Simpson R M, Zhu Y Q, Hickey M J, Sherman D R, et al. The 16-kDa alpha-crystallin (Acr) protein of *Mycobacterium tuberculosis* Is required for growth in macrophages. Proc Natl. Acad Sci USA 1998; 95(16):9578-83.
[13] Garbe T R, Hibler N S, Deretic V. Response to reactive nitrogen intermediates in *Mycobacterium tuberculosis*: induction of the 16-kilodalton alpha-crystallin homolog by exposure to nitric oxide donors. Infect Immun 1999; 67(1):460-5.
[14] Shi L, Jung Y J, Tyagi S, Gennaro M L, North R J. Expression of Th1-mediated immunity in mouse lungs induces a *Mycobacterium tuberculosis* transcription pattern characteristic of non-replicating persistence. Proc Natl Acad Sci USA 2003; 100(1):241-6
[15] Tamura T, Ariga H, Kinashi T, Uehara S, Kikuchi T, Nakada M, et al. The role of antigenic peptide in CD4+ T helper phenotype development in a T cell receptor transgenic model. Int Immunol 2004; 16(December (12)): 1691-9.
[16] Stover C K, de la Cruz V F, Fuerst T R, Burlein J E, Benson L A, Bennett L T, et al. New use of BCG for recombinant vaccines. Nature 1991; 351(6326):456-60.
[17] Palendira U, Spratt J M, Britton W I, Triccas J A. Expanding the antigenic repertoire of BCG improves protective efficacy against aerosol *Mycobacterium tuberculosis* infection. Vaccine 2005; 23(February (14)):1680-5.
[18] Demangel C, Bean A G, Martin E, Feng C G, Kamath A T, Britton W J. Protection against aerosol *Mycobacterium tuberculosis* infection using *Mycobacterium bovis* Bacillus Calmette Guérin-infected dendritic cells. Eur J Immunol 1999; 29(6):1972-9.
[19] Triccas J A, Sun L, Palendira U, Britton W J. Comparative affects of plasmidencoded interleukin 12 and interleukin 18 on the protective efficacy of DNA vaccination against *Mycobacterium tuberculosis*. Immunol Cell Biol 2002 August; 80(4):346-50.
[20] Triccas J A. Recombinant BCG as a vaccine vehicle to protect against *tuberculosis*. Bioeng Bugs 2001; 1(2):1-6.
[21] Yuan Y, Crane D D, Simpson R M, Zhu Y Q, Hickey M J, Sherman D R, et al. The 16-kDa alpha-crystallin (Acr) protein of *Mycobacterium tuberculosis* is required for growth in macrophages. Proc Natl Acad Sci USA 1998; 95(16):9578-83.
[22] Hickman S P, Chan J, Salgame P. *Mycobacterium tuberculosis* induces differential cytokine production from dendritic cells and macrophages with divergent effects on naive T cell polarization. J Immunol 2002; 168(May (9)):4636-42.
[23] Giacomini E, Iona E, Ferroni L, Miettinen M, Fattorini L, Orefici G, et al. Infection of human macrophages and dendritic cells with *Mycobacterium tuberculosis* induces a differential cytokine gene expression that modulates T cell response. J Immunol 2001; 166(June (12)):7033-41.
[24] Dietrich J, Lundberg C V, Andersen P. TB vaccine strategies—what is needed to solve a complex problem? Tuberculosis (Edinb) 2006; 86(May-July (3-4)):163-8.
[25] Horwitz M A, Harth G, Dillon B J, Maslesa-Galic S. Recombinant *Bacillus* Calmette-Guérin (BCG) vaccines expressing the *Mycobacterium tuberculosis* 30-kDa major secretory protein induce greater protective immunity against *tuberculosis* than conventional BCG vaccines in a highly susceptible animal model. Proc Natl Acad Sci USA 2000; 97(December (25)):13853-8.
[26] Al-Zarouni M, Dale J W. Expression of foreign genes in *Mycobacterium bovis* BCG strains using different promoters reveals instability of the hsp60 promoter for expression of foreign genes in *Mycobacterium bovis* BCG strains. *Tuberculosis* (Edinb) 2002; 82(6):283-91.

[27] Jagannath C, Lindsey D R, Dhandayuthapani S, Xu Y, Hunter Jr R L, Eissa N T. Autophagy enhances the efficacy of BCG vaccine by increasing peptide presentation in mouse dendritic cells. Nat Med 2009; 15(March (3)):267-76.

[28] Hohmann E L, Oletta C A, Loomis W P, Miller S I. Macrophage-inducible expression of a model antigen in *Salmonella typhimurium* enhances immunogenicity. Proc Natl Acad Sci USA 1995; 92(March (7)):2904-8.

[29] Dunstan S J, Simmons C P, Strugnell R A. Use of in vivo-regulated promoters to deliver antigens from attenuated *Salmonella enterica* var *Typhimurium*. Infect Immun 1999; 67(October (10)):5133-41.

[30] Londono L P, Chatfield S, Tindle R W, Herd K, Gao X M, Frazer I, et al. Immunisation of mice using *Salmonella typhimurium* expressing human papillomavirus type 16 E7 epitopes inserted into hepatitis B virus core antigen. Vaccine 1996; 14(April (6)):545-52.

Pinto R., Harrison J S, Hsu T, et al. Sulfite reduction in mycobacteria. J Bacteriol 2007; 189: 6714-22.

Hara S, Payne M A, Schnackerz K D, et al A rapid purification procedure and computer-assisted sulfide ion selective electrode assay for O-acetlyserine sulfhydrylase from *Salmonella typhimurium*. Protein Expr Purif 1990; 1:70-6

Sun M, Leyh, T. S. Channeling in sulfate activating complexes. Biochemistry 2006; 45:11304-11.

TABLE 1

Supplementary
Primer and clones for protein purification used in this study

For Real-time PCR

| Gene annotation | Gene name | Forward primer | Reverse primer |
|---|---|---|---|
| cysDN | ATP sulfurylase | 5'-agt cat cgc cga aac tgc-3' | 5'-ttg cca tcg tcg acg gaa-3' |
| cysH | APS reductase | 5'-gac atc gcg ggt gga ca-3' | 5'-gac gga etc gat cgc atc tc-3' |
| sirA | Sulphite reductase | 5'-gtt cga gca cag cat ttg gt-3' | 5'-gtc cgt cgt cga tca tct gt-3' |
| cysK1 | O-Acetyl-serine Sulfhydralse | 5'-ttc tcg aac cca cga gcg-3' | 5'-ccc gga gtg agg atg agt tc-3' |
| cysE | Serine Acetlysulfhydralse | 5'-ttc atc gac cac gcg acc-3' | 5'-gat cgg acc gag gac ctt g-3' |
| rrs | 16s rRNA | 5'-agg cag cag tgg gga ata-3' | 5'-cta ccg tca atc cga gag aa-3' |

For DNA vaccine cloning-all genes cloned into pcDNA3.
Restriction Enzyme site used in cloning is highlighted.

| | Forward primer | Reverse primer |
|---|---|---|
| DNA-cysD | cysD was cut out of a pET22b (Novagen) vector using BamHI and XhoI restriction enzymes and cloned into pcDNA3 cut with the same enzymes | |
| DNA-cysN | cysN was cut out of a pET22b vector using BamHI and NotI restriction enzymes and cloned into pcDNA3 cut with the same enzymes | |
| DNA-cysH | 5'-acg aaa gct tat gag cgg cga gac a-3' | 5'-ggg ggg atc ccg agg cgt gca acc c-3' |
| DNA-sirA | 5'-tag gaa gct tat gtc cgc gaa gga g-3' | 5'-tcg cgg tac ctc gca ggt cgt cct c-3' |
| DNA-cysK1 | 5'-ggc gaa gct tat gag cat cgc cga g-3' | 5'-gca tgg atc cgt cagcca cgt cgg c-3' |
| DNA-cysE | 5'-tga caa gct tat gct gac ggc cat g-3' | 5'-tat tgg tac cga tcg aga agt cct c-3' |

For protein purification

| | Description | Reference |
|---|---|---|
| CysDN | Described previously | ((Pinto, 2004; Sun, 2005) |
| CysH | Described previously | ((Sun, 2006) |
| SirA | Described previously | ((Pinto, 2007) |
| CysK1 | Cloned into pET-23A (Noavagen) using Nde I and BamH I restriction enzymes and purified as described previously | ((Hara, 1990; Wei, 2002) |
| CysE | Cloned into a dual-tag expression vector derived from pGEX vector ((Andreassi, 2004 #98) using Nde I and Not I restriction enzymes and was purified as described previously | ((Sun, 2005) |
| Ag85B | Cloned into pET19b (Noavagen) expression vector with NdeI & BamHI restriction enzymes and purification of this protein was carried out through standard His-tag purification protocols (Qiagen) | |

(CysD nucleic sequence)

SEQ ID No: 1

ATGGCAATAACCATAAATATGGTCAATCCTACCGGATTTATCAGGTATGAGGACGTGGAACAG

GAAGCCATGACCAGCGATGTGACGGTGGGCCCCGCACCCGGCCAGTACCAACTGAGCCATCTG

CGCTTGCTGGAGGCCGAAGCCATCCACGTCATCCGGGAGGTGGCCGCCGAGTTCGAGCGGCCA

GTGCTGTTGTTCTCGGGGGGCAAGGACTCCATCGTCATGCTGCACCTGGCGCTGAAGGCGTTT

CGGCCCGGGCGACTGCCGTTCCCGGTCATGCACGTCGACACCGGTCACAACTTCGACGAAGTT

ATCGCTACCCGAGACGAGTTGGTCGCCGCGGCCGGGGTGCGGCTGGTGGTGGCGTCGGTGCAG

GACGATATCGATGCCGGTCGGGTCGTCGAGACCATCCCGTCGCGAAATCCGATACAGACCGTG

ACGCTGCTGCGGGCCATCCGGGAGAACCAATTCGACGCGGCATTCGGGGGAGCCCGGCGCGAC

GAGGAGAAGGCCCGCGCCAAGGAGCGGGTGTTCAGCTTCCGCGACGAGTTCGGCCAGTGGGAC

CCGAAGGCTCAGCGGCCGGAACTGTGGAACCTCTACAACGGACGGCACCACAAGGGCGAGCAC

ATCCGGGTCTTCCCGCTGTCCAACTGGACCGAATTCGACATCTGGTCCTACATCGGCGCCGAG

CAGGTCAGGCTGCCGTCCATCTATTTCGCCCACCGGCGCAAGGTGTTTCAGCGCGACGGCATG

TTGCTGGCCGTGCACCGGCACATGCAACCGCGAGCCGACGAGCCGGTGTTCGAGGCCACGGTG

CGATTCCGCACCGTCGGGGATGTTACCTGCACCGGGTGCGTCGAGTCGTCGGCATCGACGGTC

GCGGAAGTCATCGCCGAAACTGCGGTGGCCCGCTTGACGGAGCGCGGGGCGACCAGGGCTGAC

GACCGGATCTCGGAGGCTGGAATGGAAGACCGCAAGCGGCAGGGATACTTCTGA (CysD amino acid sequence)

SEQ ID No: 2

MAITINMVNPTGFIRYEDVEQEAMTSDVTVGPAPGQYQLSHLRLLEAEAIHVIREVAAEFERP

VLLFSGGKDSIVMLHLALKAFRPGRLPFPVMHVDTGHNFDEVIATRDELVAAAGVRLVVASVQ

DDIDAGRVVETIPSRNPIQTVTLLRAIRENQFDAAFGGARRDEEKARAKERVFSFRDEFGQWD

PKAQRPELWNLYNGRHHKGEHIRVFPLSNWTEFDIWSYIGAEQVRLPSIYFAHRRKVFQRDGM

LLAVHRHMQPRADEPVFEATVRFRTVGDVTCTGCVESSASTVAEVIAETAVARLTERGATRAD

DRISEAGMEDRKRQGYF (CysNC DNA sequence)

SEQ ID No: 3

ATGACGACGCTATTGCGGCTGGCGACAGCGGGTTCCGTCGACGATGGCAAGTCCACGCTGATT

GGCGGCTACTCTACGACTCCAAGGCTGTGATGGAAGACCAGTGGGCGTCGGTGGAGCAAACG

TCCAAGGACCGGGGCCACGACTACACCGACCTGGCTCTGGTCACCGACGGCCTGCGGGCCGAG

CGGGAACAGGGCATCACCATCGACGTTGCCTACCGCTACTTCGCCACTCCCAAGCGGAAATTC

ATCATTGCCGACACCCCGGGACACATCCAATACACCCGCAACATGGTGACCGGTGCGTCCACC

GCCCAACTGGTGATCGTACTGGTGGATGCCCGGCACGGCTTGCTGGAGCAATCCCGCCGGCAC

GCCTTCCTGGCGTCGCTGCTGGGCATCCGCCACCTGGTGCTCGCGGTCAACAAGATGGACTTG

CTTGGCTGGGACCAAGAGAAATTCGACGCGATTCGAGACGAATTCCACGCCTTCGCGGCCCGC

CTCGACGTGCAGGACGTCACCTCCATCCCAATCTCCGCGCTGCACGGCGACAACGTGGTGACC

AAATCCGACCAGACGCCCTGGTACGAGGGACCGTCGCTGCTGTCGCATCTCGAAGACGTCTAC

ATCGCCGGTGACCGCAACATGGTCGACGTGCGATTCCCGGTCCAGTACGTCATCCGGCCGCAC

ACCCTCGAGCATCAAGACCACCGCAGCTACGCGGGCACCGTGGCCAGTGGGGTAATGCGTTCA

GGCGACGAAGTTGTCGTGCTGCCGATCGGTAAGACCACCCGGATCACCGCGATCGACGGCCCG

AACGGCCCGGTGGCAGAAGCGTTTCCGCCGATGGCGGTTTCGGTGCGGCTCGCCGACGACATC

GATATCTCGCGTGGTGACATGATCGCTCGCACCCACAACCAGCCCAGGATCACACAAGAATTC

GACGCGACCGTGTGCTGGATGGCCGACAACGCGGTGCTAGAGCCCGGCCGCGACTACGTTGTC

-continued

```
AAGCACACCACCCGAACCGTCCGCGCGAGGATAGCCGGGCTGGATTACCGGCTCGATGTCAAC

ACCCTGCATCGCGACAAGACCGCAACGGCGTTGAAACTCAACGAACTGGGCCGTGTTTCGCTG

CGCACCCAGGTGCCGTTGCTGCTTGACGAGTACACCCGCAACGCTAGCACCGGCTCGTTCATC

CTCATTGACCCCGACACCAACGGAACGGTGGCGGCGGGCATGGTGTTACGCGACGTCTCGGCC

CGCACGCCTAGCCCGAACACGGTGCGGCACAGATCGCTCGTCACTGCGCAAGATCGGCCGCCC

AGGGGCAAGACGGTGTGGTTTACCGGACTGTCCGGCTCCGGCAAGTCGTCGGTGGCCATGCTG

GTTGAGCGGAAGCTACTCGAAAAGGGCATCTCCGCTTACGTTCTGGACGGCGACAACCTACGG

CATGGCCTCAACGCCGACCTGGGCTTTTCCATGGCCGACCGCGCGGAGAACCTGCGCCGGCTG

TCGCATGTGGCCACACTGCTCGCCGATTGTGGCCACCTGGTGCTGGTGCCCGCGATCAGCCCC

CTTGCTGAGCACCGTGCCCTGGCTCGTAAAGTGCACGCTGATGCGGGAATCGACTTTTTCGAG

GTGTTCTGTGACACCCCGCTGCAGGACTGTGAGAGGCGTGATCCCAAAGGGTTGTACGCCAAA

GCGCGTGCGGGTGAGATCACGCACTTCACCGGGATCGACAGCCCATATCAGCGGCCCAAGAAC

CCAGACCTACGGCTTACGCCGGATCGCAGCATAGACGAGCAGGCGCAGGAGGTTATCGACCTG

TTGGAGTCATCGTCTTAG
```

(CysNC amino acid sequence)  
SEQ ID No: 4

```
MTTLLRLATAGSVDDGKSTLIGRLLYDSKAVMEDQWASVEQTSKDRGHDYTDLALVTDGLRAR

EQGITIDVAYRYFATPKRKFIIADTPGHIQYTRNMVTGASTAQLVIVLVDARHGLLEQSRRHA

FLASLLGIRHLVLAVNKMDLLGWDQEKFDAIRDEFHAFAARLDVQDVTSIPISALHGDNVVTK

SDQTPWYEGPSLLSHLEDVYIAGDRNMVDVRFPVQYVIRPHTLEHQDHRSYAGTVASGVMRSG

DEVVVLPIGKTTRITAIDGPNGPVAEAFPPMAVSVRLADDIDISRGDMIARTHNQPRITQEFD

ATVCWMADNAVLEPGRDYVVKHTTRTVRARIAGLDYRLDVNTLHRDKTATALKLNELGRVSLR

TQVPLLLDEYTRNASTGSFILIDPDTNGTVAAGMVLRDVSARTPSPNTVRHRSLVTAQDRPPR

GKTVWFTGLSGSGKSSVAMLVERKLLEKGISAYVLDGDNLRHGLNADLGFSMADRAENLRRLS

HVATLLADCGHLVLVPAISPLAEHRALARKVHADAGIDFFEVFCDTPLQDCERRDPKGLYAKA

RAGEITHFTGIDSPYQRPKNPDLRLTPDRSIDEQAQEVIDLLESSS
```

(Ag85B nucleic acid sequence)  
SEQ ID No: 5

```
ATGACAGACGTGAGCCGAAAGATTCGAGCTTGGGGACGCCGATTGATGATCGGCACGGCAGCG

GCTGTAGTCCTTCCGGGCCTGGTGGGGCTTGCCGGCGGAGCGGCAACCGCGGGCGCGTTCTCC

CGGCCGGGGCTGCCGGTCGAGTACCTGCAGGTGCCGTCGCCGTCGATGGGCCGCGACATCAAG

GTTCAGTTCCAGAGCGGTGGGAACAACTCACCTGCGGTTTATCTGCTCGACGGCCTGCGCGCC

CAAGACGACTACAACGGCTGGGATATCAACACCCCGGCGTTCGAGTGGTACTACCAGTCGGGA

CTGTCGATAGTCATGCCGGTCGGCGGGCAGTCCAGCTTCTACAGCGACTGGTACAGCCCGGCC

TGCGGTAAGGCTGGCTGCCAGACTTACAAGTGGGAAACCTTCCTGACCAGCGAGCTGCCGCAA

TGGTTGTCCGCCAACAGGGCCGTGAAGCCCACCGGCAGCGCTGCAATCGGCTTGTCGATGGCC

GGCTCGTCGGCAATGATCTTGGCCGCCTACCACCCCCAGCAGTTCATCTACGCCGGCTCGCTG

TCGGCCCTGCTGGACCCCTCTCAGGGGATGGGCCTAGCCTGATCGGCCTCGCGATGGGTGAC

GCCGGCGGTTACAAGGCCGCAGACATGTGGGGTCCCTCGAGTGACCCGGCATGGGAGCGCAAC

GACCCTACGCAGCAGATCCCCAAGCTGGTCGCAAACAACACCCGGCTATGGGTTTATTGCGGG

AACGGCACCCCGAACGAGTTGGGCGGTGCCAACATACCCGCCGAGTTCTTGGAGAACTTCGTT

CGTAGCAGCAACCTGAAGTTCCAGGATGCGTACAACGCCGCGGGCGGGCACAACGCCGTGTTC
```

-continued

AACTTCCCGCCCAACGGCACGCACAGCTGGGAGTACTGGGGCGCTCAGCTCAACGCCATGAAG
GGTGACCTGCAGAGTTCGTTAGGCGCCGGCTGA (Ag85B amino acid sequence)

SEQ ID No: 6

MTDVSRKIRAWGRRLMIGTAAAVVLPGLVGLAGGAATAGAFSRPGLPVEYLQVPSPSMGRDIK

VQFQSGGNNSPAVYLLDGLRAQDDYNGWDINTPAFEWYYQSGLSIVMPVGGQSSFYSDWYSPA

CGKAGCQTYKWETFLTSELPQWLSANRAVKPTGSAAIGLSMAGSSAMILAAYHPQQFIYAGSL

SALLDPSQGMGPSLIGLAMGDAGGYKAADMWGPSSDPAWERNDPTQQIPKLVANNTRLWVYCG

NGTPNELGGANIPAEFLENFVRSSNLKFQDAYNAAGGHNAVFNFPPNGTHSWEYWGAQLNAMK

GDLQSSLGAG (HspX promoter)

SEQ ID No: 7

CTGCACCGCGCTCTTGATGACATCGGTGGTCACCATGGTGTCCGGCATGATCAACCTCCGCTG

TTCGATATCACCCCGATCTTTCTGAACGGCGGTTGGCAGACAACAGGGTCAATGGTCCCCAAG

TGGATCACCGACGGGCGCGGACAAATGGCCCGCGCTTCGGGGACTTCTGTCCCTAGCCCTGGC

CACGATGGGCTGGTCGGATCAAAGGCATCCGTTTCCATCGATTAGGAGG (Ag85BCysD amino acid sequence)

SEQ ID No: 8

MTDVSRKIRAWGRRLMIGTAAAVVLPGLVGLAGGAATAGAFSRPGLPVEYLQVPSPSMGRDIK

VQFQSGGNNSPAVYLLDGLRAQDDYNGWDINTPAFEWYYQSGLSIVMPVGGQSSFYSDWYSPA

CGKAGCQTYKWETFLTSELPQWLSANRAVKPTGSAAIGLSMAGSSAMILAAYHPQQFIYAGSL

SALLDPSQGMGPSLIGLAMGDAGGYKAADMWGPSSDPAWERNDPTQQIPKLVANNTRLWVYCG

NGTPNELGGANIPAEFLENFVRSSNLKFQDAYNAAGGHNAVFNFPPNGTHSWEYWGAQLNAMK

GDLQSSLGAGGFMAITINMVNPTGFIRYEDVEQEAMTSDVTVGPAPGQYQLSHLRLLEAEAIH

VIREVAAEFERPVLLFSGGKDSIVMLHLALKAFRPGRLPFPVMHVDTGHNFDEVIATRDELVA

AAGVRLVVASVQDDIDAGRVVETIPSRNPIQTVTLLRAIRENQFDAAFGGARRDEEKARAKER

VFSFRDEFGQWDPKAQRPELWNLYNGRHHKGEHIRVFPLSNWTEFDIWSYIGAEQVRLPSIYF

AHRRKVFQRDGMLLAVRHMQPRADEPVFEATVRFRTVGDVTCTGCVESSASTVAEVIAETAV

ARLTERGATRADDRISEAGMEDRKRQGYF (pHspX85BCysD nucleic acid sequence)

SEQ ID No: 9

CTAGACGCCACCCTCCGGGCCGTTGCTTCGCAACGTTCAAATCCGCTCCCGGCGGATTTGTCC

TACTCAGGAGAGCGTTCACCGACAAACAACAGATAAAACGAAAGGCCCAGCCTTTCGACTGAG

CCTTTCGTTTTATTTGATGCCTGGCAGTTCCCTACTCTCGCATGGGGAGACCCCACACTACCA

TCGGCGCTAGAGCCGACTAGACCTGCACCGCGCTCTTGATGACATCGGTGGTCACCATGGTGT

CCGGCATGATCAACCTCCGCTGTTCGATATCACCCCGATCTTTCTGAACGGCGGTTGGCAGAC

AACAGGGTCAATGGTCCCCAAGTGGATCACCGACGGGCGCGGACAAATGGCCCGCGCTTCGGG

GACTTCTGTCCCTAGCCCTGGCCACGATGGGCTGGTCGGATCAAAGGCATCCGTTTCCATCGA

TTAGGAGGAAGCTTATGACAGACGTGAGCCGAAAGATTCGAGCTTGGGACGCCGATTGATGA

*TCGGCACGGCAGCGGCTGTAGTCCTTCCGGGCCTGGTGGGCTTGCCGGCGGAGCGGCAACCG*

*CGGGCGCGTTCTCCCGGCCGGGGCTGCCGGTCGAGTACCTGCAGGTGCCGTCGCCGTCGATGG*

*GCCGCGACATCAAGGTTCAGTTCCAGAGCGGTGGGAACAACTCACCTGCGGTTTATCTGCTCG*

*ACGGCCTGCGCGCCCAAGACGACTACAACGGCTGGGATATCAACACCCCGGCGTTCGAGTGGT*

*ACTACCAGTCGGGACTGTCGATAGTCATGCCGGTCGGCGGGCAGTCCAGCTTCTACAGCGACT*

*GGTACAGCCCGGCCTGCGGTAAGGCTGGCTGCCAGACTTACAAGTGGGAAACCTTCCTGACCA*

-continued

```
GCGAGCTGCCGCAATGGTTGTCCGCCAACAGGGCCGTGAAGCCCACCGGCAGCGCTGCAATCG
GCTTGTCGATGGCCGGCTCGTCGGCAATGATCTTGGCCGCCTACCACCCCCAGCAGTTCATCT
ACGCCGGCTCGCTGTCGGCCCTGCTGGACCCCTCTCAGGGGATGGGGCCTAGCCTGATCGGCC
TCGCGATGGGTGACGCCGGCGGTTACAAGGCCGCAGACATGTGGGGTCCCTCGAGTGACCCGG
CATGGGAGCGCAACGACCCTACGCAGCAGATCCCCAAGCTGGTCGCAAACAACACCCGGCTAT
GGGTTTATTGCGGGAACGGCACCCCGAACGAGTTGGGCGGTGCCAACATACCCGCCGAGTTCT
TGGAGAACTTCGTTCGTAGCAGCAACCTGAAGTTCCAGGATGCGTACAACGCCGCGGGCGGGC
ACAACGCCGTGTTCAACTTCCCGCCCAACGGCACGCACAGCTGGGAGTACTGGGGCGCTCAGC
TCAACGCCATGAAGGGTGACCTGCAGAGTTCGTTAGGCGCCGGCGGATCCATGGCAATAACCA
TAAATATGGTCAATCCTACCGGATTTATCAGGTATGAGGACGTGGAACAGGAAGCCATGACCA
GCGATGTGACGGTGGGCCCCGCACCCGGCCAGTACCAACTGAGCCATCTGCGCTTGCTGGAGG
CCGAAGCCATCCACGTCATCCGGGAGGTGGCCGCCGAGTTCGAGCGGCCAGTGCTGTTGTTCT
CGGGGGGCAAGGACTCCATCGTCATGCTGCACCTGGCGCTGAAGGCGTTTCGGCCCGGGCGAC
TGCCGTTCCCGGTCATGCACGTCGACACCGGTCACAACTTCGACGAAGTTATCGCTACCCGAG
ACGAGTTGGTCGCCGCGGCCGGGGTGCGGCTGGTGGTGGCGTCGGTGCAGGACGATATCGATG
CCGGTCGGGTCGTCGAGACCATCCCGTCGCGAAATCCGATACAGACCGTGACGCTGCTGCGGG
CCATCCGGGAGAACCAATTCGACGCGGCATTCGGGGGAGCCCGGCGCGACGAGGAGAAGGCCC
GCGCCAAGGAGCGGGTGTTCAGCTTCCGCGACGAGTTCGGCCAGTGGGACCCGAAGGCTCAGC
GGCCGGAACTGTGGAACCTCTACAACGGACGGCACCACAAGGGCGAGCACATCCGGGTCTTCC
CGCTGTCCAACTGGACCGAATTCGACATCTGGTCCTACATCGGCGCCGAGCAGGTCAGGCTGC
CGTCCATCTATTTCGCCCACCGGCGCAAGGTGTTTCAGCGCGACGGCATGTTGCTGGCCGTGC
ACCGGCACATGCAACCGCGAGCCGACGAGCCGGTGTTCGAGGCCACGGTGCGATTCCGCACCG
TCGGGGATGTTACCTGCACCGGGTGCGTCGAGTCGTCGGCATCGACGGTCGCGGAAGTCATCG
CCGAAACTGCGGTGGCCCGCTTGACGGAGCGCGGGGCGACCAGGGCTGACGACCGGATCTCGG
AGGCTGGAATGGAAGACCGCAAGCGGCAGGGATACTTCCAGCTGCACCACCACCACCACCACT
GA GTTAACTAGCGTACGATCGACTGCCAGGCATCAAATAAAACGAAAGGCTCAGTCGAAAGAC
TGGGCCTTTCGTTTTATGCCATCATGGCCGCGGTGATCAGCTAGCCACCTGACGTCGGGGGGG
GGGGAAAGCGACGTTGTGTCTCAAAATCTCTGATGTTACATTGCACAAGATAAAATATATCAT
CATGAACAATAAAACTGTCTGCTTACATAAACAGTAATACAAGGGGTGTTATGAGCCATATTC
AACGGGAAACGTCTTGCTCGAGGCCGCGATTAAATTCCAACATGGATGCTGATTTATATGGGT
ATAAATGGGCTCGCGATAATGTCGGGCAATCAGGTGCGACAATCTATCGCTTGTATGGGAAGC
CCCATGCGCCAGAGTTGTTTCTGAAACATGGCAAAGGTAGCGTTGCCAATGATGTTACAGATG
AGATGGTCAGACTAAACTGGCTGACGGAATTTATGCCTCTTCCGACCATCAAGCATTTTATCC
GTACTCCTGATGATGCATGGTTACTCACCACTGCGATCCCCGGGAAAACAGCATTCCAGGTAT
TAGAAGAATATCCTGATTCAGGTGAAAATATTGTTGATGCGCTGGCAGTGTTCCTGCGCCGGT
TGCATTCGATTCCTGTTTGTAATTGTCCTTTTAACAGCGATCGCGTATTTCGTCTCGCTCAGG
CGCAATCACGAATGAATAACGGTTTGGTTGATGCGAGTGATTTTGATGACGAGCGTAATGGCT
GGCCTGTTGAACAAGTCTGGAAAGAAATGCATAATCTTTTGCCATTCTCACCGGATTCAGTCG
TCACTCATGGTGATTTCTCACTTGATAACCTTATTTTTGACGAGGGGAAATTAATAGGTTGTA
TTGATGTTGGACGAGTCGGAATCGCAGACCGATACCAGGATCTTGCCATCCTATGGAACTGCC
```

-continued

```
TCGGTGAGTTTTCTCCTTCATTACAGAAACGGCTTTTTCAAAAATATGGTATTGATAATCCTG
ATATGAATAAATTGCAGTTTCATTTGATGCTCGATGAGTTTTTCTAATCAGAATTGGTTAATT
GGTTGTAACACTGGCAGAGCATTACGCTGACTTGACGGGACGGCGGCTTTGTTGAATAAATCG
AACTTTTGCTGAGTTGAAGGATCAGATCACGCATCTTCCCGACAACGCAGACCGTTCCGTGGC
AAAGCAAAAGTTCAAAATCACCAACTGGTCCACCTACAACAAAGCTCTCATCAACCGTGGCTC
CCTCACTTTCTGGCTGGATGATGGGGCGATTCAGGCCTGGTATGAGTCAGCAACACCTTCTTC
ACGAGGCAGACCTCACTAGTTCCACTGAGCGTCAGACCCCGTAGAAAAGATCAAAGGATCTTC
TTGAGATCCTTTTTTTCTGCGCGTAATCTGCTGCTTGCAAACAAAAAAACCACCGCTACCAGC
GGTGGTTTGTTTGCCGGATCAAGAGCTACCAACTCTTTTTCCGAAGGTAACTGGCTTCAGCAG
AGCGCAGATACCAAATACTGTCCTTCTAGTGTAGCCGTAGTTAGGCCACCACTTCAAGAACTC
TGTAGCACCGCCTACATACCTCGCTCTGCTAATCCTGTTACCAGTGGCTGCTGCCAGTGGCGA
TAAGTCGTGTCTTACCGGGTTGGACTCAAGACGATAGTTACCGGATAAGGCGCAGCGGTCGGG
CTGAACGGGGGGTTCGTGCACACAGCCCAGCTTGGAGCGAACGACCTACACCGAACTGAGATA
CCTACAGCGTGAGCATTGAGAAAGCGCCACGCTTCCCGAAGGGAGAAAGGCGGACAGGTATCC
GGTAAGCGGCAGGGTCGGAACAGGAGAGCGCACGAGGGAGCTTCCAGGGGGAAACGCCTGGTA
TCTTTATAGTCCTGTCGGGTTTCGCCACCTCTGACTTGAGCGTCGATTTTTGTGATGCTCGTC
AGGGGGGCGGAGCCTATGGAAAAACGCCAGCAACGCGGCCTTTTTACGGTTCCTGGCCTTTTG
CTGGCCTTTTGCTCACATGTTCTTTCCTGCGTTATCCCCTGATTCTGTGGATAACCGTATTAC
CGCCTTTGAGTGAGCTGATACCGCTCGCCGCAGCCGAACGACCGAGCGCAACGCGTGAGCCCA
CCAGCTCCGTAAGTTCGGGTGCTGTGTGGCTCGTACCCGCGCATTCAGGCGGCAGGGGGTCTA
ACGGGTCTAAGGCGGCGTGTACGGCCGCCACAGCGGCTCTTAGCGGCCCGGAAACGTCCTCGA
AACGACGCATGTGTTCCTCCTGGTTGGTACAGGTGGTTGGGGGTGCTCGGCTGTCGCTGGTGT
TTCATCATCAGGGCTCGACGGGAGAGCGGGGGAGTGTGCAGTTGTGGGGTGGCCCCTCAGCGA
AATATCTGACTTGGAGCTCGTGTCGGACCATACACCGGTGATTAATCGTGGTTTATTATCAAG
CGTGAGCCACGTCGCCGACGAATTTGAGCAGCTCTGGCTGCCGTACTGGTCCCTGGCAAGCGA
CGATCTGCTCGAGGGGATCTACCGCCAAAGCCGCGCGTCGGCCCTAGGCCGCCGGTACATCGA
GGCGAACCCAACAGCGCTGGCAAACCTGCTGGTCGTGGACGTAGACCATCCAGACGCAGCGCT
CCGAGCGCTCAGCGCCCGGGGGTCCCATCCGCTGCCCAACGCGATCGTGGGCAATCGCGCCAA
CGGCCACGCACACGCAGTGTGGGCACTCAACGCCCCTGTTCCACGCACCGAATACGCGCGGCG
TAAGCCGCTCGCATACATGGCGGCGTGCGCCGAAGGCCTTCGGCGCGCCGTCGATGGCGACCG
CAGTTACTCAGGCCTCATGACCAAAAACCCCGGCCACATCGCCTGGGAAACGGAATGGCTCCA
CTCAGATCTCTACACACTCAGCCACATCGAGGCCGAGCTCGGCGCGAACATGCCACCGCCGCG
CTGGCGTCAGCAGACCACGTACAAAGCGGCTCCGACGCCGCTAGGGCGGAATTGCGCACTGTT
CGATTCCGTCAGGTTGTGGGCCTATCTTCCCGCCCTCATGCGGATCTACCTGCCGACCCGGAA
CGTGGACGGACTCGGCCGCGCGATCTATGCCGAGTGCCACGCGCGAAACGCCGAATTTCCGTG
CAACGACGTGTGTCCCGGACCGCTACCGGACAGCGAGGTCCGCGCCATCGCCAACAGCATTTG
GCGTTGGATCACAACCAAGTCGCGCATTTGGGCGGACGGGATCGTGGTCTACGAGGCCACACT
CAGTGCGCGCCATGCGGCCATCTCGCGGAAGGGCGCAGCAGCGCGCACGGCGGCGAGCACAGT
TGCGCGGCGCGCAAAGTCCGCGTCAGCCATGGAGGCATTGCTATGAGCGACGGCTACAGCGAC
GGCTACAGCGACGGCTACAACTGGCAGCCGACTGTCCGCAAAAAGCGGCGCGTGACCGCCGCC
GAAGGCGCTCGAATCACCGGACTATCCGAACGCCACGTCGTCCGGCTCGTGGCGCAGGAACGC
```

AGCGAGTGGTTCGCCGAGCAGGCTGCACGCCGCGAACGCATCCGCGCCTATCACGACGACGAG

GGCCACTCTTGGCCGCAAACGGCCAAACATTTCGGGCTGCATCTGGACACCGTTAAGCGACTC

GGCTATCGGGCGAGGAAAGAGCGTGCGGCAGAACAGGAAGCGGCTCAAAAGGCCCACAACGAA

GCCGACAATCCACCGCTGTTCTAACGCAATTGGGGAGCGGGTGTCGCGGGGGTTCCGTGGGGG

GTTCCGTTGCAACGGGTCGGACAGGTAAAAGTCCTGGTAGACGCTAGTTTTCTGGTTTGGGCC

ATGCCTGTCTCGTTGCGTGTTTCGTTGCGTCCGTTTTGAATACCAGCCAGACGAGACGGGGTT

CTACGAATCTTGGTCGATACCAAGCCATTTCCGCTGAATATCGTGGAGCTCACCGCCAGAATC

GGTGGTTGTGGTGATGTACGTGGCGAACTCCGTTGTAGTGCTTGTGGTGGCATCCGTGGCGCG

GCCGCGGTACCAGATCTTTAAAT

Bold = hspX promoter sequence

Bold & underlined = cloning sites

*Italic* = Ag85B-CysD gene

<u>Underlined</u> = 6 histidine tag

---

The invention claimed is:

1. A recombinant or synthetic protein including:
   a first region having the sequence of a CysD protein as shown in SEQ ID NO: 2; and
   a further region having the sequence of an Ag85B protein, having the sequence shown in SEQ ID NO: 6.

2. The recombinant or synthetic protein according to claim 1 wherein the protein has the sequence as shown in SEQ ID NO: 8.

3. A vaccine or immune stimulating composition for providing an immune response to *Mycobacterium tuberculosis* in an individual including:
   a recombinant or synthetic protein having the sequence encoded by a CysD gene wherein the protein has the sequence as shown in SEQ ID NO: 2; and
   an effective amount of a compound for potentiating an immune response to the recombinant or synthetic protein.

4. A vaccine or composition according to claim 3, wherein the recombinant or synthetic protein further has the sequence of a CysNC protein as shown in SEQ ID NO: 4.

5. A vaccine or composition according to claim 3, wherein the recombinant or synthetic protein includes the sequence of an Ag85B protein as shown in SEQ ID NO: 6.

6. A vaccine or composition according to claim 3, wherein the recombinant or synthetic protein has the sequence as shown in SEQ ID NO: 8.

7. The vaccine or composition according to claim 3, wherein the compound for potentiating an immune response includes an adjuvant in the form of monophosphoryllipid A (MPL) and/or dimethyl dioctadecyl ammoniumbromide (DDA).

8. The vaccine or composition according to claim 3, wherein the recombinant or synthetic protein is provided in the vaccine or composition in the form recombinant bacterial cell having the recombinant or synthetic protein expressed in the cell.

* * * * *

SEQUENCE LISTING

<160> NUMBER OF SEQ ID NOS: 29

<210> SEQ ID NO 1
<211> LENGTH: 999
<212> TYPE: DNA
<213> ORGANISM: Mycobacterium SPP

<400> SEQUENCE: 1

```
atggcaataa ccataaatat ggtcaatcct accggattta tcaggtatga ggacgtggaa      60
caggaagcca tgaccagcga tgtgacggtg ggccccgcac ccggccagta ccaactgagc     120
catctgcgct tgctggaggc cgaagccatc cacgtcatcc gggaggtggc cgccgagttc     180
gagcggccag tgctgttgtt ctcgggggc aaggactcca tcgtcatgct gcacctggcg      240
ctgaaggcgt ttcggcccgg cgactgccg ttcccggtca tgcacgtcga caccggtcac      300
aacttcgacg aagttatcgc tacccgagac gagttggtcg ccgcggccgg ggtgcggctg     360
gtggtggcgt cggtgcagga cgatatcgat gccggtcggg tcgtcgagac catcccgtcg     420
cgaaatccga tacagaccgt gacgctgctg cgggccatcc gggagaacca attcgacgcg     480
gcattcgggg gagcccggcg cgacgaggag aaggcccgcg ccaaggagcg ggtgttcagc     540
ttccgcgacg agttcggcca gtgggacccg aaggctcagc ggccggaact gtggaacctc     600
tacaacggac ggcaccacaa gggcgagcac atccgggtct tcccgctgtc caactggacc     660
gaattcgaca tctggtccta catcggcgcc gagcaggtca ggctgccgtc catctatttc     720
gcccaccggc gcaaggtgtt tcagcgcgac ggcatgttgc tggccgtgca ccggcacatg     780
caaccgcgag ccgacgagcc ggtgttcgag gccacggtgc gattccgcac cgtcggggat     840
gttacctgca ccgggtgcgt cgagtcgtcg gcatcgacgg tcgcggaagt catcgccgaa     900
actgcggtgg cccgcttgac ggagcgcggg gcgaccaggg ctgacgaccg gatctcggag     960
gctggaatgg aagaccgcaa gcggcaggga tacttctga                           999
```

<210> SEQ ID NO 2
<211> LENGTH: 332
<212> TYPE: PRT
<213> ORGANISM: Mycobacterium SPP

<400> SEQUENCE: 2

| | | | | | | | | | | | | | | |
|---|---|---|---|---|---|---|---|---|---|---|---|---|---|---|
| Met | Ala | Ile | Thr | Ile | Asn | Met | Val | Asn | Pro | Thr | Gly | Phe | Ile | Arg | Tyr |
| 1 | | | | 5 | | | | | 10 | | | | | 15 | |

Met Ala Ile Thr Ile Asn Met Val Asn Pro Thr Gly Phe Ile Arg Tyr
1               5                   10                  15

Glu Asp Val Glu Gln Glu Ala Met Thr Ser Asp Val Thr Val Gly Pro
            20                  25                  30

Ala Pro Gly Gln Tyr Gln Leu Ser His Leu Arg Leu Leu Glu Ala Glu
        35                  40                  45

Ala Ile His Val Ile Arg Glu Val Ala Ala Glu Phe Glu Arg Pro Val
    50                  55                  60

Leu Leu Phe Ser Gly Gly Lys Asp Ser Ile Val Met Leu His Leu Ala
65              70                  75                  80

Leu Lys Ala Phe Arg Pro Gly Arg Leu Pro Phe Pro Val Met His Val
                85                  90                  95

Asp Thr Gly His Asn Phe Asp Glu Val Ile Ala Thr Arg Asp Glu Leu
            100                 105                 110

Val Ala Ala Ala Gly Val Arg Leu Val Val Ala Ser Val Gln Asp Asp
        115                 120                 125

Ile Asp Ala Gly Arg Val Val Glu Thr Ile Pro Ser Arg Asn Pro Ile
130                 135                 140

Gln Thr Val Thr Leu Leu Arg Ala Ile Arg Glu Asn Gln Phe Asp Ala
145                 150                 155                 160

Ala Phe Gly Gly Ala Arg Arg Asp Glu Glu Lys Ala Arg Ala Lys Glu
                165                 170                 175

Arg Val Phe Ser Phe Arg Asp Glu Phe Gly Gln Trp Asp Pro Lys Ala
            180                 185                 190

Gln Arg Pro Glu Leu Trp Asn Leu Tyr Asn Gly Arg His His Lys Gly
        195                 200                 205

Glu His Ile Arg Val Phe Pro Leu Ser Asn Trp Thr Glu Phe Asp Ile
    210                 215                 220

Trp Ser Tyr Ile Gly Ala Glu Gln Val Arg Leu Pro Ser Ile Tyr Phe
225                 230                 235                 240

Ala His Arg Arg Lys Val Phe Gln Arg Asp Gly Met Leu Leu Ala Val
                245                 250                 255

His Arg His Met Gln Pro Arg Ala Asp Glu Pro Val Phe Glu Ala Thr
            260                 265                 270

Val Arg Phe Arg Thr Val Gly Asp Val Thr Cys Thr Gly Cys Val Glu
        275                 280                 285

Ser Ser Ala Ser Thr Val Ala Glu Val Ile Ala Glu Thr Ala Val Ala
    290                 295                 300

Arg Leu Thr Glu Arg Gly Ala Thr Arg Ala Asp Asp Arg Ile Ser Glu
305                 310                 315                 320

Ala Gly Met Glu Asp Arg Lys Arg Gln Gly Tyr Phe
                325                 330

<210> SEQ ID NO 3
<211> LENGTH: 1845
<212> TYPE: DNA
<213> ORGANISM: Mycobacterium SPP

<400> SEQUENCE: 3

```
atgacgacgc tattgcggct ggcgacagcg ggttccgtcg acgatggcaa gtccacgctg      60
attgggcggc tactctacga ctccaaggct gtgatggaag accagtgggc gtcggtggag     120
caaacgtcca aggaccgggg ccacgactac accgacctgg ctctggtcac cgacggcctg     180
```

```
cgggccgagc gggaacaggg catcaccatc gacgttgcct accgctactt cgccactccc    240
aagcggaaat tcatcattgc cgacaccccg ggacacatcc aatacacccg caacatggtg    300
accggtgcgt ccaccgccca actggtgatc gtactggtgg atgcccggca cggcttgctg    360
gagcaatccc gccggcacgc cttcctggcg tcgctgctgg catccgcca cctggtgctc    420 gcggtcaaca agatggactt gcttggctgg gaccaagaga aattcgacgc gattcgagac    480
gaattccacg ccttcgcggc ccgcctcgac gtgcaggacg tcacctccat cccaatctcc    540
gcgctgcacg gcgacaacgt ggtgaccaaa tccgaccaga cgccctggta cgagggaccg    600
tcgctgctgt cgcatctcga agacgtctac atcgccggtg accgcaacat ggtcgacgtg    660
cgattcccgg tccagtacgt catccggccg cacaccctcg agcatcaaga ccaccgcagc    720
tacgcgggca ccgtggccag tggggtaatg cgttcaggcg acgaagttgt cgtgctgccg    780
atcggtaaga ccacccggat caccgcgatc gacggcccga acggcccggt ggcagaagcg    840
tttccgccga tggcggtttc ggtgcggctc gccgacgaca tcgatatctc gcgtggtgac    900
atgatcgctc gcacccacaa ccagcccagg atcacacaag aattcgacgc gaccgtgtgc    960
tggatggccg acaacgcggt gctagagccc ggccgcgact acgttgtcaa gcacaccacc   1020
cgaaccgtcc gcgcgaggat agccgggctg gattaccggc tcgatgtcaa caccctgcat   1080
cgcgacaaga ccgcaacggc gttgaaactc aacgaactgg ccgtgtttc gctgcgcacc   1140 caggtgccgt tgctgcttga cgagtacacc cgcaacgcta gcaccggctc gttcatcctc   1200
attgaccccg acaccaacgg aacggtggcg gcgggcatgg tgttacgcga cgtctcggcc   1260
cgcacgccta gcccgaacac ggtgcggcac agatcgctcg tcactgcgca agatcggccg   1320
cccaggggca agacggtgtg gtttaccgga ctgtccggct ccggcaagtc gtcggtggcc   1380
atgctggttg agcggaagct actcgaaaag gcatctccg cttacgttct ggacggcgac   1440
aacctacggc atggcctcaa cgccgacctg ggctttccca tggccgaccg cgcggagaac   1500
ctgcgccggc tgtcgcatgt ggccacactg ctcgccgatt gtggccacct ggtgctggtg   1560
cccgcgatca gccccttgc tgagcaccgt gccctggctc gtaaagtgca cgctgatgcg   1620
ggaatcgact ttttcgaggt gttctgtgac acccgctgc aggactgtga gaggcgtgat   1680
cccaaagggt tgtacgccaa agcgcgtgcg ggtgagatca cgcacttcac cgggatcgac   1740
agcccatatc agcggcccaa gaacccagac ctacggctta cgccggatcg cagcatagac   1800
gagcaggcgc aggaggttat cgacctgttg gagtcatcgt cttag                   1845
```

<210> SEQ ID NO 4
<211> LENGTH: 613
<212> TYPE: PRT
<213> ORGANISM: Mycobacterium SPP

<400> SEQUENCE: 4

```
Met Thr Thr Leu Leu Arg Leu Ala Thr Ala Gly Ser Val Asp Asp Gly
1               5                   10                  15

Lys Ser Thr Leu Ile Gly Arg Leu Leu Tyr Asp Ser Lys Ala Val Met
            20                  25                  30

Glu Asp Gln Trp Ala Ser Val Glu Gln Thr Ser Lys Asp Arg Gly His
        35                  40                  45

Asp Tyr Thr Asp Leu Ala Leu Val Thr Asp Gly Leu Arg Ala Arg Glu
    50                  55                  60

Gln Gly Ile Thr Ile Asp Val Ala Tyr Arg Tyr Phe Ala Thr Pro Lys
65                  70                  75                  80
```

-continued

```
Arg Lys Phe Ile Ile Ala Asp Thr Pro Gly His Ile Gln Tyr Thr Arg
                85                  90                  95

Asn Met Val Thr Gly Ala Ser Thr Ala Gln Leu Val Ile Val Leu Val
            100                 105                 110

Asp Ala Arg His Gly Leu Leu Glu Gln Ser Arg Arg His Ala Phe Leu
        115                 120                 125

Ala Ser Leu Leu Gly Ile Arg His Leu Val Leu Ala Val Asn Lys Met
130                 135                 140

Asp Leu Leu Gly Trp Asp Gln Glu Lys Phe Asp Ala Ile Arg Asp Glu
145                 150                 155                 160

Phe His Ala Phe Ala Ala Arg Leu Asp Val Gln Asp Val Thr Ser Ile
                165                 170                 175

Pro Ile Ser Ala Leu His Gly Asp Asn Val Val Thr Lys Ser Asp Gln
            180                 185                 190

Thr Pro Trp Tyr Glu Gly Pro Ser Leu Leu Ser His Leu Glu Asp Val
        195                 200                 205

Tyr Ile Ala Gly Asp Arg Asn Met Val Asp Val Arg Phe Pro Val Gln
210                 215                 220

Tyr Val Ile Arg Pro His Thr Leu Glu His Gln Asp His Arg Ser Tyr
225                 230                 235                 240

Ala Gly Thr Val Ala Ser Gly Val Met Arg Ser Gly Asp Glu Val Val
                245                 250                 255

Val Leu Pro Ile Gly Lys Thr Thr Arg Ile Thr Ala Ile Asp Gly Pro
            260                 265                 270

Asn Gly Pro Val Ala Glu Ala Phe Pro Met Ala Val Ser Val Arg
        275                 280                 285

Leu Ala Asp Asp Ile Asp Ile Ser Arg Gly Asp Met Ile Ala Arg Thr
290                 295                 300

His Asn Gln Pro Arg Ile Thr Gln Glu Phe Asp Ala Thr Val Cys Trp
305                 310                 315                 320

Met Ala Asp Asn Ala Val Leu Glu Pro Gly Arg Asp Tyr Val Val Lys
                325                 330                 335

His Thr Thr Arg Thr Val Arg Ala Arg Ile Ala Gly Leu Asp Tyr Arg
            340                 345                 350

Leu Asp Val Asn Thr Leu His Arg Asp Lys Thr Ala Thr Ala Leu Lys
        355                 360                 365

Leu Asn Glu Leu Gly Arg Val Ser Leu Arg Thr Gln Val Pro Leu Leu
370                 375                 380

Leu Asp Glu Tyr Thr Arg Asn Ala Ser Thr Gly Ser Phe Ile Leu Ile
385                 390                 395                 400

Asp Pro Asp Thr Asn Gly Thr Val Ala Ala Gly Met Val Leu Arg Asp
                405                 410                 415

Val Ser Ala Arg Thr Pro Ser Pro Asn Thr Val Arg His Arg Ser Leu
            420                 425                 430

Val Thr Ala Gln Asp Arg Pro Arg Gly Lys Thr Val Trp Phe Thr
        435                 440                 445

Gly Leu Ser Gly Ser Gly Lys Ser Ser Val Ala Met Leu Val Glu Arg
450                 455                 460

Lys Leu Leu Glu Lys Gly Ile Ser Ala Tyr Val Leu Asp Gly Asp Asn
465                 470                 475                 480

Leu Arg His Gly Leu Asn Ala Asp Leu Gly Phe Ser Met Ala Asp Arg
                485                 490                 495
```

```
Ala Glu Asn Leu Arg Arg Leu Ser His Val Ala Thr Leu Leu Ala Asp
            500                 505                 510

Cys Gly His Leu Val Leu Val Pro Ala Ile Ser Pro Leu Ala Glu His
        515                 520                 525

Arg Ala Leu Ala Arg Lys Val His Ala Asp Ala Gly Ile Asp Phe Phe
    530                 535                 540

Glu Val Phe Cys Asp Thr Pro Leu Gln Asp Cys Glu Arg Arg Asp Pro
545                 550                 555                 560

Lys Gly Leu Tyr Ala Lys Ala Arg Ala Gly Glu Ile Thr His Phe Thr
                565                 570                 575

Gly Ile Asp Ser Pro Tyr Gln Arg Pro Lys Asn Pro Asp Leu Arg Leu
            580                 585                 590

Thr Pro Asp Arg Ser Ile Asp Glu Gln Ala Gln Glu Val Ile Asp Leu
            595                 600                 605

Leu Glu Ser Ser Ser
        610
```

<210> SEQ ID NO 5
<211> LENGTH: 978
<212> TYPE: DNA
<213> ORGANISM: Mycobacterium SPP

<400> SEQUENCE: 5

```
atgacagacg tgagccgaaa gattcgagct tggggacgcc gattgatgat cggcacggca      60
gcggctgtag tccttccggg cctggtgggg cttgccggcg agcggcaac  cgcgggcgcg     120
ttctcccggc cggggctgcc ggtcgagtac ctgcaggtgc cgtcgccgtc gatgggccgc     180
gacatcaagg ttcagttcca gagcggtggg aacaactcac ctgcggttta tctgctcgac     240
ggcctgcgcg cccaagacga ctacaacggc tgggatatca acaccccggc gttcgagtgg     300
tactaccagt cgggactgtc gatagtcatg ccggtcggcg ggcagtccag cttctacagc     360
gactggtaca gccggcctg cggtaaggct ggctgccaga cttacaagtg gaaaccttc      420
ctgaccagcg agctgccgca atggttgtcc gccaacaggg ccgtgaagcc caccggcagc     480
gctgcaatcg gcttgtcgat ggccggctcg tcggcaatga tcttggccgc ctaccacccc     540
cagcagttca tctacgccgg ctcgctgtcg gccctgctgg acccctctca ggggatgggg     600
cctagcctga tcgcctcgc gatgggtgac gccggcggtt acaaggccgc agacatgtgg     660
ggtccctcga gtgacccggc atgggagcgc aacgacccta cgcagcagat ccccaagctg     720
gtcgcaaaca cacccggct atgggttat tgcgggaacg gcaccccgaa cgagttgggc      780
ggtgccaaca tacccgccga gttcttggag aacttcgttc gtagcagcaa cctgaagttc     840
caggatgcgt acaacgccgc gggcgggcac aacgccgtgt tcaacttccc gcccaacggc     900
acgcacagct gggagtactg gggcgctcag ctcaacgcca tgaagggtga cctgcagagt     960
tcgttaggcg ccggctga                                                   978
```

<210> SEQ ID NO 6
<211> LENGTH: 325
<212> TYPE: PRT
<213> ORGANISM: Mycobacterium SPP

<400> SEQUENCE: 6

```
Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30
```

-continued

```
Gly Gly Ala Ala Thr Ala Gly Ala Phe Ser Arg Pro Gly Leu Pro Val
            35                  40                  45
Glu Tyr Leu Gln Val Pro Ser Pro Ser Met Gly Arg Asp Ile Lys Val
 50                  55                  60
Gln Phe Gln Ser Gly Asn Asn Ser Pro Ala Val Tyr Leu Leu Asp
 65                  70                  75                  80
Gly Leu Arg Ala Gln Asp Asp Tyr Asn Gly Trp Asp Ile Asn Thr Pro
                 85                  90                  95
Ala Phe Glu Trp Tyr Tyr Gln Ser Gly Leu Ser Ile Val Met Pro Val
            100                 105                 110
Gly Gly Gln Ser Ser Phe Tyr Ser Asp Trp Tyr Ser Pro Ala Cys Gly
            115                 120                 125
Lys Ala Gly Cys Gln Thr Tyr Lys Trp Glu Thr Phe Leu Thr Ser Glu
130                 135                 140
Leu Pro Gln Trp Leu Ser Ala Asn Arg Ala Val Lys Pro Thr Gly Ser
145                 150                 155                 160
Ala Ala Ile Gly Leu Ser Met Ala Gly Ser Ser Ala Met Ile Leu Ala
                165                 170                 175
Ala Tyr His Pro Gln Gln Phe Ile Tyr Ala Gly Ser Leu Ser Ala Leu
            180                 185                 190
Leu Asp Pro Ser Gln Gly Met Gly Pro Ser Leu Ile Gly Leu Ala Met
            195                 200                 205
Gly Asp Ala Gly Gly Tyr Lys Ala Ala Asp Met Trp Gly Pro Ser Ser
210                 215                 220
Asp Pro Ala Trp Glu Arg Asn Asp Pro Thr Gln Gln Ile Pro Lys Leu
225                 230                 235                 240
Val Ala Asn Asn Thr Arg Leu Trp Val Tyr Cys Gly Asn Gly Thr Pro
                245                 250                 255
Asn Glu Leu Gly Gly Ala Asn Ile Pro Ala Glu Phe Leu Glu Asn Phe
            260                 265                 270
Val Arg Ser Ser Asn Leu Lys Phe Gln Asp Ala Tyr Asn Ala Ala Gly
            275                 280                 285
Gly His Asn Ala Val Phe Asn Phe Pro Pro Asn Gly Thr His Ser Trp
290                 295                 300
Glu Tyr Trp Gly Ala Gln Leu Asn Ala Met Lys Gly Asp Leu Gln Ser
305                 310                 315                 320
Ser Leu Gly Ala Gly
                325
```

```
<210> SEQ ID NO 7
<211> LENGTH: 238
<212> TYPE: DNA
<213> ORGANISM: Mycobacterium SPP

<400> SEQUENCE: 7
ctgcaccgcg ctcttgatga catcggtggt caccatggtg tccggcatga tcaacctccg    60
ctgttcgata tcaccccgat ctttctgaac ggcggttggc agacaacagg gtcaatggtc   120
cccaagtgga tcaccgacgg cgcggacaa atgcccgcg cttcggggac ttctgtccct     180
agccctggcc acgatgggct ggtcggatca aaggcatccg tttccatcga ttaggagg    238

<210> SEQ ID NO 8
<211> LENGTH: 659
<212> TYPE: PRT
<213> ORGANISM: Artificial Sequence
```

<220> FEATURE:
<223> OTHER INFORMATION: Ag85BCysD amino acid sequence

<400> SEQUENCE: 8

```
Met Thr Asp Val Ser Arg Lys Ile Arg Ala Trp Gly Arg Arg Leu Met
1               5                   10                  15

Ile Gly Thr Ala Ala Val Val Leu Pro Gly Leu Val Gly Leu Ala
                20                  25                  30

Gly Gly Ala Ala Thr Ala Gly Ala Phe Ser Arg Pro Gly Leu Pro Val
                35                  40                  45

Glu Tyr Leu Gln Val Pro Ser Pro Ser Met Gly Arg Asp Ile Lys Val
50                  55                  60

Gln Phe Gln Ser Gly Gly Asn Asn Ser Pro Ala Val Tyr Leu Leu Asp
65                  70                  75                  80

Gly Leu Arg Ala Gln Asp Asp Tyr Asn Gly Trp Asp Ile Asn Thr Pro
                85                  90                  95

Ala Phe Glu Trp Tyr Tyr Gln Ser Gly Leu Ser Ile Val Met Pro Val
                100                 105                 110

Gly Gly Gln Ser Ser Phe Tyr Ser Asp Trp Tyr Ser Pro Ala Cys Gly
                115                 120                 125

Lys Ala Gly Cys Gln Thr Tyr Lys Trp Glu Thr Phe Leu Thr Ser Glu
130                 135                 140

Leu Pro Gln Trp Leu Ser Ala Asn Arg Ala Val Lys Pro Thr Gly Ser
145                 150                 155                 160

Ala Ala Ile Gly Leu Ser Met Ala Gly Ser Ala Met Ile Leu Ala
                165                 170                 175

Ala Tyr His Pro Gln Gln Phe Ile Tyr Ala Gly Ser Leu Ser Ala Leu
                180                 185                 190

Leu Asp Pro Ser Gln Gly Met Gly Pro Ser Leu Ile Gly Leu Ala Met
                195                 200                 205

Gly Asp Ala Gly Gly Tyr Lys Ala Ala Asp Met Trp Gly Pro Ser Ser
                210                 215                 220

Asp Pro Ala Trp Glu Arg Asn Asp Pro Thr Gln Gln Ile Pro Lys Leu
225                 230                 235                 240

Val Ala Asn Asn Thr Arg Leu Trp Val Tyr Cys Gly Asn Gly Thr Pro
                245                 250                 255

Asn Glu Leu Gly Gly Ala Asn Ile Pro Ala Glu Phe Leu Glu Asn Phe
                260                 265                 270

Val Arg Ser Ser Asn Leu Lys Phe Gln Asp Ala Tyr Asn Ala Ala Gly
                275                 280                 285

Gly His Asn Ala Val Phe Asn Phe Pro Pro Asn Gly Thr His Ser Trp
                290                 295                 300

Glu Tyr Trp Gly Ala Gln Leu Asn Ala Met Lys Gly Asp Leu Gln Ser
305                 310                 315                 320

Ser Leu Gly Ala Gly Phe Met Ala Ile Thr Ile Asn Met Val Asn
                325                 330                 335

Pro Thr Gly Phe Ile Arg Tyr Glu Asp Val Glu Gln Glu Ala Met Thr
                340                 345                 350

Ser Asp Val Thr Val Gly Pro Ala Pro Gly Gln Tyr Gln Leu Ser His
                355                 360                 365

Leu Arg Leu Leu Glu Ala Glu Ala Ile His Val Ile Arg Glu Val Ala
                370                 375                 380

Ala Glu Phe Glu Arg Pro Val Leu Leu Phe Ser Gly Gly Lys Asp Ser
385                 390                 395                 400
```

Ile Val Met Leu His Leu Ala Leu Lys Ala Phe Arg Pro Gly Arg Leu
            405                 410                 415

Pro Phe Pro Val Met His Val Asp Thr Gly His Asn Phe Asp Glu Val
            420                 425                 430

Ile Ala Thr Arg Asp Glu Leu Val Ala Ala Gly Val Arg Leu Val
            435                 440                 445

Val Ala Ser Val Gln Asp Asp Ile Asp Ala Gly Arg Val Val Glu Thr
450                 455                 460

Ile Pro Ser Arg Asn Pro Ile Gln Thr Val Thr Leu Leu Arg Ala Ile
465                 470                 475                 480

Arg Glu Asn Gln Phe Asp Ala Ala Phe Gly Gly Ala Arg Arg Asp Glu
            485                 490                 495

Glu Lys Ala Arg Ala Lys Glu Arg Val Phe Ser Phe Arg Asp Glu Phe
            500                 505                 510

Gly Gln Trp Asp Pro Lys Ala Gln Arg Pro Glu Leu Trp Asn Leu Tyr
            515                 520                 525

Asn Gly Arg His His Lys Gly Glu His Ile Arg Val Phe Pro Leu Ser
            530                 535                 540

Asn Trp Thr Glu Phe Asp Ile Trp Ser Tyr Ile Gly Ala Glu Gln Val
545                 550                 555                 560

Arg Leu Pro Ser Ile Tyr Phe Ala His Arg Arg Lys Val Phe Gln Arg
            565                 570                 575

Asp Gly Met Leu Leu Ala Val His Arg His Met Gln Pro Arg Ala Asp
            580                 585                 590

Glu Pro Val Phe Glu Ala Thr Val Arg Phe Arg Thr Val Gly Asp Val
            595                 600                 605

Thr Cys Thr Gly Cys Val Glu Ser Ser Ala Ser Thr Val Ala Glu Val
            610                 615                 620

Ile Ala Glu Thr Ala Val Ala Arg Leu Thr Glu Arg Gly Ala Thr Arg
625                 630                 635                 640

Ala Asp Asp Arg Ile Ser Glu Ala Gly Met Glu Asp Arg Lys Arg Gln
                    645                 650                 655

Gly Tyr Phe

<210> SEQ ID NO 9
<211> LENGTH: 6512
<212> TYPE: DNA
<213> ORGANISM: Artificial Sequence
<220> FEATURE:
<223> OTHER INFORMATION: pHspX85BCysD nucleic acid sequence

<400> SEQUENCE: 9
ctagacgcca ccctccgggc cgttgcttcg caacgttcaa atccgctccc ggcggatttg      60
tcctactcag gagagcgttc accgacaaac aacagataaa acgaaaggcc cagcctttcg     120
actgagcctt tcgttttatt tgatgcctgg cagttcccta ctctcgcatg ggagaccccc     180
acactaccat cggcgctaga gccgactaga cctgcaccgc gctcttgatg acatcggtgg     240
tcaccatggt gtccggcatg atcaacctcc gctgttcgat atcaccccga tctttctgaa     300
cggcggttgg cagacaacag ggtcaatggt ccccaagtgg atcaccgacg ggcgcggaca     360
aatggcccgc gcttcgggga cttctgtccc tagccctggc cacgatgggc tggtcggatc     420
aaaggcatcc gtttccatcg attaggagga agcttatgac agacgtgagc cgaaagattc     480
gagcttgggg acgccgattg atgatcggca cggcagcggc tgtagtcctt ccgggcctgg     540

```
tggggcttgc cggcggagcg gcaaccgcgg gcgcgttctc ccggccgggg ctgccggtcg      600
agtacctgca ggtgccgtcg ccgtcgatgg gccgcgacat caaggttcag ttccagagcg      660
gtgggaacaa ctcacctgcg gtttatctgc tcgacggcct gcgcgcccaa gacgactaca      720
acggctggga tatcaacacc ccggcgttcg agtggtacta ccagtcggga ctgtcgatag      780
tcatgccggt cggcgggcag tccagcttct acagcgactg gtacagcccg gcctgcggta      840
aggctggctg ccagacttac aagtgggaaa ccttcctgac cagcgagctg ccgcaatggt      900
tgtccgccaa cagggccgtg aagcccaccg gcagcgctgc aatcggcttg tcgatggccg      960
gctcgtcggc aatgatcttg gccgcctacc accccccagca gttcatctac gccggctcgc     1020
tgtcggccct gctggacccc tctcagggga tggggcctag cctgatcggc ctcgcgatgg     1080
gtgacgccgg cggttacaag gccgcagaca tgtggggtcc ctcgagtgac ccggcatggg     1140
agcgcaacga ccctacgcag cagatccccca agctggtcgc aaacaacacc cggctatggg     1200
tttattgcgg gaacggcacc ccgaacgagt tgggcggtgc caacataccc gccgagttct     1260
tggagaactt cgttcgtagc agcaacctga gttccagga tgcgtacaac gccgcgggcg     1320
ggcacaacgc cgtgttcaac ttcccgccca acggcacgca cagctgggag tactggggcg     1380
ctcagctcaa cgccatgaag ggtgacctgc agagttcgtt aggcgccggc ggatccatgg     1440
caataaccat aaatatggtc aatcctaccg gatttatcag gtatgaggac gtggaacagg     1500
aagccatgac cagcgatgtg acggtgggcc ccgcacccgg ccagtaccaa ctgagccatc     1560
tgcgcttgct ggaggccgaa gccatccacg tcatccggga ggtggccgcc gagttcgagc     1620
ggccagtgct gttgttctcg gggggcaagg actccatcgt catgctgcac ctggcgctga     1680
aggcgtttcg gcccgggcga ctgccgttcc cggtcatgca cgtcgacacc ggtcacaact     1740
tcgacgaagt tatcgctacc cgagacgagt tggtcgccgc ggccggggtg cggctggtgg     1800
tggcgtcggt gcaggacgat atcgatgccg gtcgggtcgt cgagaccatc ccgtcgcgaa     1860
atccgataca gaccgtgacg ctgctgcggg ccatccggga gaaccaattc gacgcggcat     1920
tcggggagc ccggcgcgac gaggagaagg cccgcgccaa ggagcgggtg ttcagcttcc      1980
gcgacgagtt cggccagtgg gacccgaagg ctcagcggcc ggaactgtgg aacctctaca     2040
acggacggca ccacaagggc gagcacatcc gggtcttccc gctgtccaac tggaccgaat     2100
tcgacatctg gtcctacatc ggcgccgagc aggtcaggct gccgtccatc tatttcgccc     2160
accggcgcaa ggtgtttcag cgcgacggca tgttgctggc cgtgcaccgg cacatgcaac     2220
cgcgagccga cgaccggtg ttcgaggcca cggtgcgatt ccgcaccgtc ggggatgtta      2280
cctgcaccgg gtgcgtcgag tcgtcggcat cgacggtcgc ggaagtcatc gccgaaactg     2340
cggtggcccg cttgacggag cgcggggcga ccagggctga cgaccggatc tcggaggctg     2400
gaatggaaga ccgcaagcgg cagggatact tccagctgca ccaccaccac caccactgag     2460
ttaactagcg tacgatcgac tgccaggcat caaataaaac gaaaggctca gtcgaaagac     2520
tgggcctttc gttttatgcc atcatggccg cggtgatcag ctagccacct gacgtcgggg     2580
ggggggaaa gcgacgttgt gtctcaaaat ctctgatgtt acattgcaca agataaaata     2640
tatcatcatg aacaataaaa ctgtctgctt acataaacag taatacaagg ggtgttatga     2700
gccatattca acgggaaacg tcttgctcga ggccgcgatt aaattccaac atggatgctg     2760
atttatatgg gtataaatgg ctcgcgata atgtcgggca atcaggtgcg acaatctatc     2820
gcttgtatgg gaagcccat gcgccagagt tgttctgaa acatggcaaa ggtagcgttg     2880
ccaatgatgt tacagatgag atggtcagac taaactggct gacggaattt atgcctcttc     2940
```

```
cgaccatcaa gcattttatc cgtactcctg atgatgcatg gttactcacc actgcgatcc    3000
ccgggaaaac agcattccag gtattagaag aatatcctga ttcaggtgaa aatattgttg    3060
atgcgctggc agtgttcctg cgccggttgc attcgattcc tgtttgtaat tgtcctttta    3120
acagcgatcg cgtatttcgt ctcgctcagg cgcaatcacg aatgaataac ggtttggttg    3180
atgcgagtga ttttgatgac gagcgtaatg gctggcctgt tgaacaagtc tggaaagaaa    3240
tgcataatct tttgccattc tcaccggatt cagtcgtcac tcatggtgat ttctcacttg    3300
ataaccttat ttttgacgag gggaaattaa taggttgtat tgatgttgga cgagtcggaa    3360
tcgcagaccg ataccaggat cttgccatcc tatggaactg cctcggtgag ttttctcctt    3420
cattacagaa acggcttttt caaaaatatg gtattgataa tcctgatatg aataaattgc    3480
agtttcattt tgatgctcga tgagttttct aatcagaatt ggttaattgg ttgtaacact    3540
ggcagagcat tacgctgact tgacgggacg gcggctttgt tgaataaatc gaacttttgc    3600
tgagttgaag gatcagatca cgcatcttcc cgacaacgca gaccgttccg tggcaaagca    3660
aaagttcaaa atcaccaact ggtccaccta caacaaagct ctcatcaacc gtggctccct    3720
cactttctgg ctggatgatg gggcgattca ggcctggtat gagtcagcaa caccttcttc    3780
acgaggcaga cctcactagt tccactgagc gtcagacccc gtagaaaaga tcaaaggatc    3840
ttcttgagat cctttttttc tgcgcgtaat ctgctgcttg caaacaaaaa aaccaccgct    3900
accagcggtg gtttgtttgc cggatcaaga gctaccaact cttttccga aggtaactgg    3960 cttcagcaga gcgcagatac caaatactgt ccttctagtg tagccgtagt taggccacca    4020
cttcaagaac tctgtagcac cgcctacata cctcgctctg ctaatcctgt taccagtggc    4080
tgctgccagt ggcgataagt cgtgtcttac cgggttggac tcaagacgat agttaccgga    4140
taaggcgcag cggtcgggct gaacggggggg ttcgtgcaca cagcccagct tggagcgaac    4200
gacctacacc gaactgagat acctacagcg tgagcattga gaaagcgcca cgcttcccga    4260
agggagaaag gcggacaggt atccggtaag cggcagggtc ggaacaggag agcgcacgag    4320
ggagcttcca gggggaaacg cctggtatct ttatagtcct gtcgggtttc gccacctctg    4380
acttgagcgt cgatttttgt gatgctcgtc aggggggcgg agcctatgga aaaacgccag    4440
caacgcggcc ttttacggtt cctggccctt ttgctggcct tttgctcaca tgttctttcc    4500
tgcgttatcc cctgattctg tggataaccg tattaccgcc tttgagtgag ctgataccgc    4560
tcgccgcagc cgaacgaccg agcgcaacgc gtgagcccac cagctccgta agttcgggtg    4620
ctgtgtggct cgtacccgcg cattcaggcg cagggggtc taacgggtct aaggcggcgt    4680
gtacggccgc cacagcggct cttagcggcc cggaaacgtc ctcgaaacga cgcatgtgtt    4740
cctcctggtt ggtacaggtg gttggggtg ctcggctgtc gctggtgttt catcatcagg    4800
gctcgacggg agagcggggg agtgtgcagt tgtgggtgg cccctcagcg aaatatctga    4860
cttggagctc gtgtcggacc atacaccggt gattaatcgt ggtttattat caagcgtgag    4920
ccacgtcgcc gacgaatttg agcagctctg gctgccgtac tggtccctgg caagcgacga    4980
tctgctcgag gggatctacc gccaaagccg cgcgtcggcc ctaggccgcc ggtacatcga    5040
ggcgaaccca acagcgctgg caaacctgct ggtcgtggac gtagaccatc cagacgcagc    5100
gctccgagcg ctcagcgccc gggggtccca tccgctgccc aacgcgatcg tgggcaatcg    5160
cgccaacggc cacgcacacg cagtgtgggc actcaacgcc cctgttccac gcaccgaata    5220
cgcgcggcgt aagccgctcg catacatggc ggcgtgcgcc gaaggccttc ggcgcgccgt    5280
```

-continued

```
cgatggcgac cgcagttact caggcctcat gaccaaaaac cccggccaca tcgcctggga    5340
aacggaatgg ctccactcag atctctacac actcagccac atcgaggccg agctcggcgc    5400
gaacatgcca ccgccgcgct ggcgtcagca gaccacgtac aaagcggctc cgacgccgct    5460
agggcggaat tgcgcactgt tcgattccgt caggttgtgg gcctatcttc ccgccctcat    5520
gcggatctac ctgccgaccc ggaacgtgga cggactcggc cgcgcgatct atgccgagtg    5580
ccacgcgcga aacgccgaat tccgtgcaa cgacgtgtgt cccggaccgc taccggacag    5640
cgaggtccgc gccatcgcca acagcatttg gcgttggatc acaaccaagt cgcgcatttg    5700
ggcggacggg atcgtggtct acgaggccac actcagtgcg cgccatgcgg ccatctcgcg    5760
gaagggcgca gcagcgcgca cggcggcgag cacagttgcg cggcgcgcaa agtccgcgtc    5820
agccatggag gcattgctat gagcgacggc tacagcgacg gctacagcga cggctacaac    5880
tggcagccga ctgtccgcaa aaagcggcgc gtgaccgccg ccgaaggcgc tcgaatcacc    5940
ggactatccg aacgccacgt cgtccggctc gtggcgcagg aacgcagcga gtggttcgcc    6000
gagcaggctg cacgccgcga acgcatccgc gcctatcacg acgacgaggg ccactcttgg    6060
ccgcaaacgg ccaaacattt cgggctgcat ctggacaccg ttaagcgact cggctatcgg    6120
gcgaggaaag agcgtgcggc agaacaggaa gcggctcaaa aggcccacaa cgaagccgac    6180
aatccaccgc tgttctaacg caattgggga gcgggtgtcg cggggggttcc gtgggggggtt    6240 ccgttgcaac gggtcggaca ggtaaaagtc ctggtagacg ctagttttct ggtttgggcc    6300
atgcctgtct cgttgcgtgt ttcgttgcgt ccgttttgaa taccagccag acgagacggg    6360
gttctacgaa tcttggtcga taccaagcca tttccgctga atatcgtgga gctcaccgcc    6420
agaatcggtg gttgtggtga tgtacgtggc gaactccgtt gtagtgcttg tggtggcatc    6480
cgtggcgcgg ccgcggtacc agatctttaa at                                  6512
```

<210> SEQ ID NO 10
<211> LENGTH: 18
<212> TYPE: DNA
<213> ORGANISM: Artificial Sequence
<220> FEATURE:
<223> OTHER INFORMATION: cysDN Forward primer

<400> SEQUENCE: 10
agtcatcgcc gaaactgc                                                  18

<210> SEQ ID NO 11
<211> LENGTH: 18
<212> TYPE: DNA
<213> ORGANISM: Artificial Sequence
<220> FEATURE:
<223> OTHER INFORMATION: cysDN reverse primer

<400> SEQUENCE: 11
ttgccatcgt cgacggaa                                                  18

<210> SEQ ID NO 12
<211> LENGTH: 17
<212> TYPE: DNA
<213> ORGANISM: Artificial Sequence
<220> FEATURE:
<223> OTHER INFORMATION: cysH forward primer

<400> SEQUENCE: 12
gacatcgcgg gtggaca                                                   17

```
<210> SEQ ID NO 13
<211> LENGTH: 20
<212> TYPE: DNA
<213> ORGANISM: Artificial Sequence
<220> FEATURE:
<223> OTHER INFORMATION: cysH reverse primer

<400> SEQUENCE: 13
gacggactcg atcgcatctc                                              20

<210> SEQ ID NO 14
<211> LENGTH: 20
<212> TYPE: DNA
<213> ORGANISM: Artificial Sequence
<220> FEATURE:
<223> OTHER INFORMATION: sirA forward primer

<400> SEQUENCE: 14
gttcgagcac agcatttggt                                              20

<210> SEQ ID NO 15
<211> LENGTH: 20
<212> TYPE: DNA
<213> ORGANISM: Artificial Sequence
<220> FEATURE:
<223> OTHER INFORMATION: sirA reverse primer

<400> SEQUENCE: 15
gtccgtcgtc gatcatctgt                                              20

<210> SEQ ID NO 16
<211> LENGTH: 18
<212> TYPE: DNA
<213> ORGANISM: Artificial Sequence
<220> FEATURE:
<223> OTHER INFORMATION: cysK1 forward primer

<400> SEQUENCE: 16
ttctcgaacc cacgagcg                                                18

<210> SEQ ID NO 17
<211> LENGTH: 20
<212> TYPE: DNA
<213> ORGANISM: Artificial Sequence
<220> FEATURE:
<223> OTHER INFORMATION: cysK1 reverse primer

<400> SEQUENCE: 17
cccggagtga ggatgagttc                                              20

<210> SEQ ID NO 18
<211> LENGTH: 18
<212> TYPE: DNA
<213> ORGANISM: Artificial Sequence
<220> FEATURE:
<223> OTHER INFORMATION: cysE forward primer

<400> SEQUENCE: 18
ttcatcgacc acgcgacc                                                18

<210> SEQ ID NO 19
<211> LENGTH: 19
<212> TYPE: DNA
<213> ORGANISM: Artificial Sequence
<220> FEATURE:
<223> OTHER INFORMATION: cysE reverse primer
```

```
<400> SEQUENCE: 19
gatcggaccg aggaccttg                                                   19

<210> SEQ ID NO 20
<211> LENGTH: 18
<212> TYPE: DNA
<213> ORGANISM: Artificial Sequence
<220> FEATURE:
<223> OTHER INFORMATION: 16S RNA forward primer

<400> SEQUENCE: 20
aggcagcagt ggggaata                                                    18

<210> SEQ ID NO 21
<211> LENGTH: 20
<212> TYPE: DNA
<213> ORGANISM: Artificial Sequence
<220> FEATURE:
<223> OTHER INFORMATION: 16S RNA reverse primer

<400> SEQUENCE: 21
ctaccgtcaa tccgagagaa                                                  20

<210> SEQ ID NO 22
<211> LENGTH: 25
<212> TYPE: DNA
<213> ORGANISM: Artificial Sequence
<220> FEATURE:
<223> OTHER INFORMATION: DNA-cysH forward primer

<400> SEQUENCE: 22
acgaaagctt atgagcggcg agaca                                            25

<210> SEQ ID NO 23
<211> LENGTH: 25
<212> TYPE: DNA
<213> ORGANISM: Artificial Sequence
<220> FEATURE:
<223> OTHER INFORMATION: DNA-cysH reverse primer

<400> SEQUENCE: 23
ggcgggatcc cgaggcgtgc aaccc                                            25

<210> SEQ ID NO 24
<211> LENGTH: 25
<212> TYPE: DNA
<213> ORGANISM: Artificial Sequence
<220> FEATURE:
<223> OTHER INFORMATION: DNA-sirA forward primer

<400> SEQUENCE: 24
taggaagctt atgtccgcga aggag                                            25

<210> SEQ ID NO 25
<211> LENGTH: 25
<212> TYPE: DNA
<213> ORGANISM: Artificial Sequence
<220> FEATURE:
<223> OTHER INFORMATION: DNA-sirA reverse primer

<400> SEQUENCE: 25
tcgcggtacc tcgcaggtcg tcctc                                            25

<210> SEQ ID NO 26
<211> LENGTH: 24
```

```
<212> TYPE: DNA
<213> ORGANISM: Artificial Sequence
<220> FEATURE:
<223> OTHER INFORMATION: DNA-cysK1 forward primer

<400> SEQUENCE: 26
ggcgaagctt agagcatcgc cgag                                  24

<210> SEQ ID NO 27
<211> LENGTH: 25
<212> TYPE: DNA
<213> ORGANISM: Artificial Sequence
<220> FEATURE:
<223> OTHER INFORMATION: DNA-cysK1 reverse primer

<400> SEQUENCE: 27
gcatggatcc gtcagccacg tcggc                                 25

<210> SEQ ID NO 28
<211> LENGTH: 25
<212> TYPE: DNA
<213> ORGANISM: Artificial Sequence
<220> FEATURE:
<223> OTHER INFORMATION: DNA-cysE forward primer

<400> SEQUENCE: 28
tgacaagctt atgctgacgg ccatg                                 25

<210> SEQ ID NO 29
<211> LENGTH: 25
<212> TYPE: DNA
<213> ORGANISM: Artificial Sequence
<220> FEATURE:
<223> OTHER INFORMATION: DNA-cysE reverse primer

<400> SEQUENCE: 29
tattggtacc gatcgagaag tcctc                                 25
```

UNITED STATES PATENT AND TRADEMARK OFFICE
CERTIFICATE OF CORRECTION

PATENT NO. : 9,610,337 B2
APPLICATION NO. : 14/367854
DATED : April 4, 2017
INVENTOR(S) : James Anthony Triccas et al.

It is certified that error appears in the above-identified patent and that said Letters Patent is hereby corrected as shown below:

On the Title Page

Please correct the item (73) Assignee to read --The University of Sydney, Sydney, NSW (AU); Centenary Institute of Cancer Medicine and Cell Biology, Camperdown, NSW (AU)--.

Signed and Sealed this
Tenth Day of July, 2018

Andrei Iancu
*Director of the United States Patent and Trademark Office*